US008748361B2

(12) United States Patent
Wu et al.

(10) Patent No.: US 8,748,361 B2
(45) Date of Patent: Jun. 10, 2014

(54) POLYALPHA-OLEFIN COMPOSITIONS AND PROCESSES TO PRODUCE THE SAME

(75) Inventors: Margaret May-Som Wu, Skillman, NJ (US); Lisa Saunders Baugh, Ringoes, NJ (US); Jo Ann Marie Canich, Houston, TX (US); Chia Shian Chee, Houston, TX (US); Mark Paul Hagemeister, Houston, TX (US); Andrew Jackson, Pennington, NJ (US); Peijun Jiang, League City, TX (US); Gordon H. Lee, Newtown, PA (US); Frederick Yip-Kwai Lo, Middlesex, NJ (US); Steven P. Rucker, Warren, NJ (US); Shakeel Tirmizi, Matawan, NJ (US); John F. Walzer, Jr., Seabrook, TX (US); Norman Yang, Westfield, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 1369 days.

(21) Appl. No.: 11/995,118

(22) PCT Filed: Jun. 2, 2006

(86) PCT No.: PCT/US2006/021231
§ 371 (c)(1),
(2), (4) Date: May 28, 2008

(87) PCT Pub. No.: WO2007/011459
PCT Pub. Date: Jan. 25, 2007

(65) Prior Publication Data
US 2009/0005279 A1 Jan. 1, 2009

Related U.S. Application Data

(60) Provisional application No. 60/700,600, filed on Jul. 19, 2005.

(51) Int. Cl.
*C10L 1/16* (2006.01)
(52) U.S. Cl.
USPC .......................................................... 508/591
(58) Field of Classification Search
USPC .......................... 508/517, 521, 523, 524, 591
See application file for complete search history.

(56) References Cited

U.S. PATENT DOCUMENTS

| | | | |
|---|---|---|---|
| 2,978,442 A | 4/1961 | Brightbill et al. | |
| 3,149,178 A | 9/1964 | Hamilton et al. | |
| 3,164,578 A | 1/1965 | Baker et al. | |
| 3,382,291 A | 5/1968 | Brennan | |
| 3,742,082 A | 6/1973 | Brennan | |
| 3,769,363 A | 10/1973 | Brennan | |
| 3,780,128 A | 12/1973 | Shubkin | |
| 3,876,720 A | 4/1975 | Heilman et al. | |
| 3,883,417 A | 5/1975 | Woo et al. | |
| 4,016,349 A | 4/1977 | McKenna | |
| 4,132,663 A | 1/1979 | Heilman et al. | |
| 4,149,178 A | 4/1979 | Estes | |
| 4,172,855 A | 10/1979 | Shubkin et al. | |
| 4,180,575 A | 12/1979 | Rochling et al. | |
| 4,239,930 A | 12/1980 | Allphin et al. | |
| 4,263,465 A | 4/1981 | Sheng et al. | |
| 4,263,712 A | 4/1981 | Schroder | |
| 4,367,352 A | 1/1983 | Watts, Jr. et al. | |
| 4,413,156 A | 11/1983 | Watts, Jr. et al. | |
| 4,434,308 A | 2/1984 | Larkin et al. | |
| 4,451,684 A | 5/1984 | Pasky | |
| 4,469,912 A | 9/1984 | Blewett et al. | |
| 4,587,368 A | 5/1986 | Pratt | |

(Continued)

FOREIGN PATENT DOCUMENTS

| | | |
|---|---|---|
| EP | 0 277 004 | 8/1988 |
| EP | 0 277 007 | 8/1988 |

(Continued)

OTHER PUBLICATIONS

J. Brennan, "*Wide-Temperature Range Synthetic Hydrocarbon Fluids*", Ind. Eng. Chem. Prod. Res. Dev., 1980, vol. 19, pp. 2-6.

(Continued)

*Primary Examiner* — James Goloboy
*Assistant Examiner* — Latosha Hines
(74) *Attorney, Agent, or Firm* — Leandro Arechederra, III; Luke A. Parsons

(57) ABSTRACT

This invention relates to a polyalpha-olefin (and hydrogenated analogs thereof) comprising more than 50 mole % of one or more C5 to C24 alpha-olefin monomers where the polyalpha-olefin has: a) 40 mole % or more of mm triads, b) a Bromine number of Y or greater, where Y is equal to 89.92* $(V)^{-0.5863}$, where V is the Kinematic Viscosity of the polyalpha-olefin measured at 100° C. in cSt, and c) 1,2 disubstituted olefins present at 7 mole % or more, preferably having Z mole % or more of units represented by the formula: where j, k and m are each, independently, 3, 4, 5, 6, 7, 8, 9, 10, 11, 12, 13, 14, 15, 16, 17, 18, 19, 20, 21, or 22, n is an integer from 1 to 350, and where Z=8.420*Log(V)−4.048, where V is the kinematic viscosity of the polyalpha-olefin measured at 1000 C in cSt This invention also relates to process to produce such polyalpha-olefins.

(I)

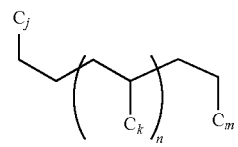

49 Claims, 10 Drawing Sheets

(56) References Cited

U.S. PATENT DOCUMENTS

| | | | |
|---|---|---|---|
| 4,701,489 A | 10/1987 | Hughes et al. | |
| 4,704,491 A | 11/1987 | Tsutsui et al. | |
| 4,827,064 A | 5/1989 | Wu | |
| 4,827,073 A | 5/1989 | Wu | |
| 4,892,851 A | 1/1990 | Ewen et al. | |
| 4,910,355 A | 3/1990 | Shubkin et al. | |
| 4,912,272 A | 3/1990 | Wu | |
| 4,914,254 A | 4/1990 | Pelrine | |
| 4,926,004 A | 5/1990 | Pelrine et al. | |
| 4,950,822 A | 8/1990 | Dileo et al. | |
| 4,956,122 A | 9/1990 | Watts et al. | |
| 4,962,262 A | 10/1990 | Winter et al. | |
| 4,967,032 A | 10/1990 | Ho et al. | |
| 4,990,709 A | 2/1991 | Wu | |
| 4,990,771 A | 2/1991 | Minoura et al. | |
| 5,012,020 A | 4/1991 | Jackson et al. | |
| 5,017,299 A | 5/1991 | Gutierrez et al. | |
| 5,017,714 A | 5/1991 | Welborn, Jr. | |
| 5,068,487 A | 11/1991 | Theriot | |
| 5,087,788 A | 2/1992 | Wu | |
| 5,177,276 A | 1/1993 | Beach et al. | |
| 5,186,851 A | 2/1993 | Gutierrez et al. | |
| 5,188,724 A | 2/1993 | Heilman et al. | |
| 5,220,100 A | 6/1993 | Massie et al. | |
| 5,264,642 A | 11/1993 | Wu | |
| 5,367,097 A * | 11/1994 | Shen et al. | 585/22 |
| 5,369,196 A | 11/1994 | Matsumoto et al. | |
| 5,382,739 A | 1/1995 | Atkins et al. | |
| 5,462,995 A | 10/1995 | Hosaka et al. | |
| 5,498,815 A | 3/1996 | Schaerfl, Jr. et al. | |
| 5,552,504 A | 9/1996 | Bennett et al. | |
| 5,637,400 A | 6/1997 | Brekner et al. | |
| 5,679,812 A | 10/1997 | Winter et al. | |
| 5,688,887 A | 11/1997 | Bagheri et al. | |
| 5,690,832 A | 11/1997 | Tavlarides et al. | |
| 5,731,254 A | 3/1998 | Winter et al. | |
| 5,811,379 A | 9/1998 | Rossi et al. | |
| 5,846,896 A | 12/1998 | Ewen | |
| 5,852,143 A | 12/1998 | Sishta et al. | |
| 5,859,159 A | 1/1999 | Rossi et al. | |
| 6,043,401 A | 3/2000 | Bagheri et al. | |
| 6,087,307 A | 7/2000 | Kaminski et al. | |
| 6,133,209 A | 10/2000 | Rath et al. | |
| 6,147,271 A | 11/2000 | Strebel et al. | |
| 6,180,575 B1 | 1/2001 | Nipe | |
| 6,388,032 B1 | 5/2002 | Yamaura et al. | |
| 6,414,090 B2 | 7/2002 | Minami et al. | |
| 6,414,091 B2 | 7/2002 | Moritomi et al. | |
| 6,479,722 B1 | 11/2002 | De Wet et al. | |
| 6,548,723 B2 | 4/2003 | Bagheri et al. | |
| 6,642,169 B2 | 11/2003 | Weatherhead | |
| 6,646,174 B2 | 11/2003 | Clarembeau | |
| 6,706,828 B2 | 3/2004 | DiMaio | |
| 6,713,438 B1 | 3/2004 | Baillargeon et al. | |
| 6,824,671 B2 | 11/2004 | Goze et al. | |
| 6,858,767 B1 | 2/2005 | DiMaio et al. | |
| 6,960,700 B1 | 11/2005 | Sethna et al. | |
| 7,060,768 B2 | 6/2006 | Brookhart et al. | |
| 7,129,197 B2 | 10/2006 | Song et al. | |
| 7,473,815 B2 | 1/2009 | Lambert et al. | |
| 7,544,850 B2 | 6/2009 | Goze et al. | |
| 7,547,811 B2 | 6/2009 | Kramer et al. | |
| 7,592,497 B2 | 9/2009 | Yang et al. | |
| 7,601,256 B2 | 10/2009 | Beall | |
| 2001/0041817 A1* | 11/2001 | Bagheri et al. | 585/517 |
| 2001/0041818 A1 | 11/2001 | Bagheri et al. | |
| 2003/0055184 A1* | 3/2003 | Song et al. | 526/160 |
| 2003/0236177 A1* | 12/2003 | Wu et al. | 508/465 |
| 2004/0022508 A1 | 2/2004 | Belardi et al. | |
| 2004/0033908 A1 | 2/2004 | Deckman et al. | |
| 2004/0054086 A1* | 3/2004 | Schauder et al. | 525/193 |
| 2004/0087746 A1 | 5/2004 | Razavi | |
| 2004/0097772 A1 | 5/2004 | Deckers et al. | |
| 2004/0147693 A1 | 7/2004 | DiMaio | |
| 2004/0220359 A1 | 11/2004 | Abhari et al. | |
| 2004/0230016 A1 | 11/2004 | Blackborow et al. | |
| 2005/0059563 A1 | 3/2005 | Sullivan et al. | |
| 2005/0101761 A1 | 5/2005 | Lambert et al. | |
| 2005/0183988 A1 | 8/2005 | Freerks et al. | |
| 2007/0000807 A1 | 1/2007 | Wu et al. | |
| 2007/0011832 A1 | 1/2007 | Keidel et al. | |
| 2007/0043248 A1 | 2/2007 | Wu et al. | |
| 2007/0208151 A1 | 9/2007 | Okada et al. | |
| 2009/0005279 A1 | 1/2009 | Wu et al. | |
| 2009/0156874 A1 | 6/2009 | Patil et al. | |
| 2009/0281360 A1 | 11/2009 | Knowles et al. | |
| 2010/0069687 A1 | 3/2010 | Kosover et al. | |

FOREIGN PATENT DOCUMENTS

| | | |
|---|---|---|
| EP | 0 284 708 | 10/1988 |
| EP | 0 321 852 | 6/1989 |
| EP | 0 349 276 | 1/1990 |
| EP | 0 377 306 | 7/1990 |
| EP | 0 403 866 | 12/1990 |
| EP | 0 513 380 | 11/1992 |
| EP | 0 613 873 | 9/1994 |
| EP | 0 680 942 | 11/1995 |
| EP | 0 930 320 | 7/1999 |
| EP | 0 992 517 | 4/2000 |
| EP | 1 028 128 | 8/2000 |
| EP | 1 309 633 | 5/2003 |
| EP | 1 342 707 | 9/2003 |
| EP | 1 607 415 | 12/2005 |
| GB | 938069 | 9/1963 |
| IN | 191553 | 12/2003 |
| JP | 63-057615 | 3/1988 |
| JP | 6336590 | 12/1994 |
| JP | 2005-200446 | 7/2005 |
| WO | 95/33781 | 12/1995 |
| WO | WO96/23751 | 8/1996 |
| WO | WO 99/67347 | 12/1999 |
| WO | 00/58423 | 10/2000 |
| WO | WO 02/14384 | 2/2002 |
| WO | 03/009136 | 1/2003 |
| WO | WO 03/020856 | 3/2003 |
| WO | 03/051943 | 6/2003 |
| WO | 03/071369 | 8/2003 |
| WO | 03/104292 | 12/2003 |
| WO | 2004/046214 | 6/2004 |
| WO | 2007/011459 | 1/2007 |
| WO | 2007/011462 | 1/2007 |
| WO | 2007/011832 | 1/2007 |
| WO | 2007/011973 | 1/2007 |
| WO | 2007/145924 | 12/2007 |
| WO | 2007/146081 | 12/2007 |
| WO | 2008/010862 | 1/2008 |
| WO | 2008/010865 | 1/2008 |
| WO | 2009/017953 | 2/2009 |
| WO | 2009/137264 | 11/2009 |

OTHER PUBLICATIONS

K. Denbigh, "*The Kinetics of Continuous Reaction Processes: Application to Polymerization*", J. Applied Chem, 1951, vol. 1, pp. 227-236.

K. Denbigh, "*Continuous Reactions: Part II. The Kinetics of Steady State Polymerisation*", Trans Faraday Soc., 1947, vol. 43, pp. 648-660.

A. Munoz-Escalona et al., "*Single-Site Supported Catalysts for Ethylene Polymerization*", Metallocene Tech., 1999, pp. 2242-2246.

Z. Fan et al., "*Effect of Ethoxy- and Methoxysilane Donors in Propene/1-Hexene Copolymerization With High-Yield Supported Ziegler-Natta Catalysts*", Macromolecular Chemistry and Physics, 1994, vol. 195, pp. 3889-3899.

G. Gokel ed, Dean's Handbook of Organic Chemistry, 2nd Edition, McGraw-Hill, 2004, available on-line at hhttp://knovel.com.

M. LeVan et al. "*Adsorption and Ion Exchange*" Perry's Chemical Engineer's Handbook, 7th ed. 1997 pp. 16-1-16-66.

O. Levenspiel, "*Ch. 7 Design for Multiple Reactions*", Chemical Reaction Engineering, 2nd ed., 1972, pp. 196-209.

(56) References Cited

OTHER PUBLICATIONS

N. Naga et al., "*Effect of Co-Catalyst System on a-Olefin Polymerization With Rac- and Meso-[Dimethylsilylenebis(2,3,5-Trimethyl-Cyclopentadienyl)]Zirconium Dichloride*", Macromol. Rapid Commun., 1997, vol. 18, pp. 581-589.

N. Naga et al, "*Polymerization Behavior of a-Olefins With Rac- and Meso-Type Ansa-Metallocene Catalysts: Effects of Cocatalyst and Metallocene Ligand*", Macromolecular Chemistry Physics, 1999, vol. 200, pp. 1587-1594.

F. Rodriguez, "*The Molecular Weight of Polymers*", Principles of Polymer Systems, 1970, Chapter 6, pp. 115-144.

M. Sacchi et al., "*Use of Different Alkoxysilanes as External Donors in $MgCl_2$-Supported Ziegler-Natta Catalysts to Obtain Propene/1-Butene Copolymers With Different Microstructure*", Macromolecular Chemistry and Physics, 1994, vol. 195, pp. 2805-2816.

T. Seraidaris et al., "*High-Molar-Mass Polypropene with Tunable Elastic Properties by Hafnocene/Borate Catalysts*", Journal of Polymer Science: Part A: Polymer Chemistry, 2006, vol. 44, pp. 4743-4751.

J. Wills, "*Synthetic Lubricants*", Lubrication Fundamentals, Marcel Dekker Inc., New York, 1980, pp. 75-80.

"*Mobil Releases SuperSyn PAOs*", Lubrication Engineers, 1999, vol. 55, Part 8, pp. 45.

TIBA data, "*TIBA datasheet*" available on-line at www.albermarle.com on Aug. 26, 2010.

Kim et al., Higher α-Olefin Polymerizations Catalyzed by rac-$Me_2Si(1-C_5H_2-2-CH_3-4-{}^tBu)_2Zr(NMe_2)_2/Al(iBu)_3/[Ph_3C][B(C_6F_5)_4]$, Journal of Polymer Science: Part A, 2000, vol. 38, pp. 1687-1697.

* cited by examiner

POLYALPHA-OLEFIN COMPOSITIONS AND PROCESSES TO PRODUCE THE SAME

CROSS-REFERENCE TO RELATED APPLICATIONS

This applciation is a national stage filing of International Patent Cooperation Treaty Application No. PCT/US2006/021231 filed Jun. 2, 2006, which claims priority from U.S. Provisional Application 60/700,600 filed Jul. 19, 2005, the disclosure of which is fully incorporated herein by reference.

FIELD OF THE INVENTION

This invention relates to a process to produce a new class of poly-alpha-olefins (PAOs) with unique chemical compositions. More specifically, this invention relates to novel PAOs prepared in the presence of a metallocene catalyst with an activator and a process for making PAOs in the presence of a metallocene catalyst with an activator.

DESCRIPTION OF RELATED ART

Efforts to improve upon the performance of natural mineral oil-based lubricants by the synthesis of oligomeric hydrocarbon fluids have been the subject of important research and development in the petroleum industry for at least fifty years. These efforts have led to the relatively recent market introduction of a number of synthetic lubricants. In terms of lubricant property improvement, the thrust of the industrial research efforts involving synthetic lubricants have been towards fluids exhibiting useful viscosities over a wide temperature range, i.e., improved viscosity index (VI), while also showing lubricities, thermal and oxidative stabilities and pour points equal to or better than those for mineral oil.

The viscosity-temperature relationship of a lubricating oil is one of the critical criteria which must be considered when selecting a lubricant for a particular application. The mineral oils commonly used as a base for single and multigraded lubricants exhibit a relatively large change in viscosity with a change in temperature. Fluids exhibiting such a relatively large change in viscosity with temperature are said to have a low viscosity index. Viscosity index is an empirical number which indicates the rate of change in the viscosity of an oil within a given temperature range. A high VI oil, for example, will thin out at elevated temperatures more slowly than a low VI oil. Usually, A high VI oil is more desirable because it has higher viscosity at higher temperature, which translates into better lubrication and better protection of the contacting machine elements, preferably at high temperatures and or at temperatures over a wide range. VI is calculated according to ASTM method D 2270.

PAOs comprise a class of hydrocarbons manufactured by the catalytic oligomerization (polymerization to low-molecular-weight products) of linear α-olefin (LAO) monomers. These typically range from 1-octene to 1-dodecene, with 1-decene being a preferred material, although oligomeric copolymers of lower olefins such as ethylene and propylene may also be used, including copolymers of ethylene with higher olefins as described in U.S. Pat. No. 4,956,122 and the patents referred to therein. PAO products have achieved importance in the lubricating oil market. Typically there are two classes of synthetic hydrocarbon fluids (SHF) produced from linear alpha-olefins, the two classes of SHF being denoted as PAO and HVI-PAO (high viscosity index PAO's). PAO's and HVI-PAO's of different viscosity grades are typically produced using promoted $BF_3$ or $AlCl_3$ catalysts.

Specifically, PAOs may be produced by the polymerization of olefin feed in the presence of a catalyst such as $AlCl_3$, $BF_3$, or $BF_3$ complexes. Processes for the production of PAOs are disclosed, for example, in the following U.S. Pat. Nos. 3,149,178; 3,382,291; 3,742,082; 3,769,363; 3,780,128; 4,172,855 and 4,956,122, which are fully incorporated by reference. PAOs are also discussed in: Will, J. G. *Lubrication Fundamentals*, Marcel Dekker: New York, 1980. Subsequent to polymerization, the PAO lubricant range products are typically hydrogenated in order to reduce the residual unsaturation, generally to a level of greater than 90%. HVI-PAO's may also be conveniently made by the polymerization of an alpha-olefin in the presence of a polymerization catalyst such as Friedel-Crafts catalysts. These include, for example, aluminum trichloride, boron trifluoride, aluminum trichloride or boron trifluoride promoted with water, with alcohols such as ethanol, propanol, or butanol, with carboxylic acids, or with esters such as ethyl acetate or ethyl propionate or ether such as diethyl ether, diisopropyl ether, etc. For example, the methods disclosed by U.S. Pat. Nos. 3,149,178 or 3,382,291 may be conveniently used herein. Other descriptions of PAO synthesis are found in the following U.S. Pat. No. 3,742,082 (Brennan); U.S. Pat. No. 3,769,363 (Brennan); U.S. Pat. No.3,876,720 (Heilman); U.S. Pat. No. 4,239,930 (Allphin); U.S. Pat. No.4,367,352 (Watts); U.S. Pat. No. 4,413,156 (Watts); U.S. Pat. No. 4,434,308 (Larkin); U. S. Pat. No. 4,910,355 (Shubkin); U.S. Pat. No. 4,956,122 (Watts); and U.S. Pat. No. 5,068,487 (Theriot).

Another class of HVI-PAOs may be prepared by the action of a supported, reduced chromium catalyst with an alpha-olefin monomer. Such PAOs are described in U.S. Pat. No. 4,827,073 (Wu); U.S. Pat. No. 4,827,064 (Wu); U.S. Pat. No. 4,967,032 (Ho et al.); U.S. Pat. No. 4,926,004 (Pelrine et al.); and U.S. Pat. No. 4,914,254 (Pelrine). Commercially available PAOs include SpectraSyn™ 2, 4, 5, 6, 8, 10, 40, 100 and SpectraSyn Ultra™ 150, SpectraSyn Ultra™ 300, SpectraSyn Ultra™ 1000, etc. (ExxonMobil Chemical Company, Houston Tex.).

Synthetic PAOs have found wide acceptability and commercial success in the lubricant field for their superiority to mineral based lubricants. In terms of lubricant property improvement, industrial research efforts on synthetic lubricants have led to PAO fluids exhibiting useful viscosities over a wide range of temperature, i.e., improved viscosity index, while also showing lubricity, thermal and oxidative stability and pour point equal to or better than mineral oil. These relatively new synthetic lubricants lower mechanical friction, enhancing mechanical efficiency over the full spectrum of mechanical loads and do so over a wider range of operating conditions than mineral oil lubricants.

Performance requirements of lubricants are becoming increasingly stringent. New PAOs with improved properties, such as high viscosity index (VI), low pour point, high shear stability, improved wear performance, increased thermal and oxidative stability, and or wider viscosity range, are needed to meet new performance requirements for lubricants. New methods to provide such new PAOs with improved properties are also needed.

Efforts have been made to prepare various PAOs using metallocene catalyst systems. Examples include U.S. Pat. No. 6,706,828 (equivalent to US 2004/0147693), where PAOs are produced from meso-forms of certain metallocene catalysts under high hydrogen pressure. Comparative example D of U.S. Pat. No. 6,706,828, however, uses rac-dimethylsilylbis (2-methyl-indenyl)zirconium dichloride in combination with methylalumoxane (MAO) at 100° C. in the presence of hydrogen to produce polydecene having a reported Kinematic Viscosity at 100° C. ($KV_{100}$) of 116 cSt, a Kinematic Viscosity at 40° C. ($KV_{40}$) of 1039 cSt, a VI of 214, an iodine number of 2.8, an Mw of 7084, an Mn of 2906, an Mw/Mn of 2.4, and a Tg of −72.4° C. Likewise, WO 02/14384 discloses, among other things, in examples J and K the use of rac-ethyl-bis (indenyl)zirconium dichloride or rac-dimethylsilyl-bis (2-methyl-indenyl)zirconium dichloride in combination with MAO at 40° C. (at 200 psi hydrogen or 1 mole of hydrogen) to produce isotactic polydecene reportedly having a Tg of −73.8° C., a $KV_{100}$ of 702 cSt, and a VI of 296; or to produce polydecene reportedly having a Tg of −66° C., a $KV_{100}$ of 1624, and a VI of 341, respectively. Further WO 99/67347 discloses in example 1 the use of ethylidene bis (tetrahydroindenyl)zirconium dichloride in combination with MAO at 50° C. to produce a polydecene having an Mn of 11,400 and 94% vinylidene double bond content.

Others have made various PAOs, such as polydecene, using various metallocene catalysts not typically known to produce polymers or oligomers with any specific tacticity. Examples include WO 96/23751, EP 0 613 873, U.S. Pat. No. 5,688,887, U.S. Pat. No. 6,043,401, WO 03/020856 (equivalent to US 2003/0055184), U.S. Pat. No. 6,548,724 (equivalent to US 2001/0041817 and U.S. Pat. No. 6,548,723), U.S. Pat. Nos. 5,087,788, 6,414,090, 6,414,091, 4,704,491, 6,133,209, and 6,713,438.

To date however, PAO's made with metallocenes have not found wide applicability in the marketplace, particularly the lubricant marketplace, due to inefficient process, cost and property deficits. The instant invention address such and other needs by providing new PAO's and or HVI-PAO's having excellent property combinations and an improved process to produce them.

SUMMARY OF INVENTION

This invention relates to a polyalpha-olefin comprising more than 50 mole % of one or more $C_5$ to $C_{24}$ alpha-olefin monomers where the polyalpha-olefin has:
a) 40 mole % or more of mm triads,
b) a Bromine number of Y or greater, where Y is equal to $89.92*(V)^{-0.5863}$, where V is the kinematic viscosity of the polyalpha-olefin in cSt measured at 100° C., and
c) 1,2 disubstituted olefins present at 7 mole % or more, preferably present at Z mole % or more, where $Z=8.420*Log(V)-4.048$ where V is the kinematic viscosity of the polyalpha-olefin measured at 100° C.

Alternately, this invention relates to a polyalpha-olefin comprising more than 50 mole % of one or more C5 to C24 alpha-olefin monomers where the polyalpha-olefin has:
a) 40 mole % or more of mm triads,
b) a Bromine number of 1.8 or less, and
c) Z mole % or more of units represented by the formula:

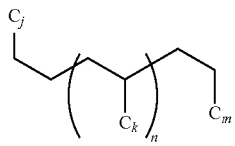

where j, k and m are each, independently, 3, 4, 5, 6, 7, 8, 9, 10, 11, 12, 13, 14, 15, 16, 17, 18, 19, 20, 21, or 22; n is an integer from 1 to 350; and
where $Z=8.420*Log(V)-4.048$, where V is the kinematic viscosity of the polyalpha-olefin measured at 100° C. in cSt Alternately, this invention relates to a polyalpha-olefin comprising more than 50 mole % of one or more C5 to C24 alpha-olefin monomers where the polyalpha-olefin has:
a) 40 mole % or more of mm triads,
b) a Bromine number of Y or greater, where Y is equal to $89.92*(V)^{-5863}$, where V is the kinematic viscosity of the polyalpha-olefin in cSt measured at 100° C., and
c) 1,2 disubstituted olefins, preferably present at Z mole % or more of units represented by the formula:

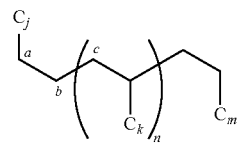

where the olefinic 1,2-disubstituted carbons will be positioned between Ca and Cb or occasionally between Cb and Cc, and where j, k and m are each, independently, 3, 4, 5, 6, 7, 8, 9, 10, 11, 12, 13, 14, 15, 16, 17, 18, 19, 20, 21, or 22; n is an integer from 1 to 350; and
where $Z=8.420*Log(V)-4.048$, where V is the kinematic viscosity of the polyalpha-olefin measured at 100° C. in cSt.

Alternately, this invention relates to a polyalpha-olefin comprising more than 50 mole % of one or more C5 to C24 alpha-olefin monomers where the polyalpha-olefin has:
a) less than 40 mole % of mm triads,
b) a Bromine number of 1.8 or less, and
c) Z mole % or more of units represented by the formula:

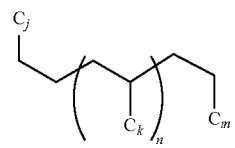

where j, k and m are each, independently, 3, 4, 5, 6, 7, 8, 9, 10, 11, 12, 13, 14, 15, or 16, n is an integer from 1 to 350, and
where $Z=8.420*Log(V)-4.048$, where V is the kinematic viscosity of the polyalpha-olefin measured at 100° C. in cSt Alternately, this invention relates to a polyalpha-olefin comprising more than 50 mole % of one or more C5 to C24 alpha-olefin monomers where the polyalpha-olefin has Z mole % or more of units represented by the formula:

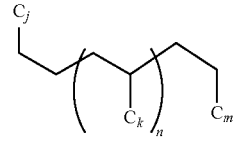

where j, k and m are each, independently, 3, 4, 5, 6, 7, 8, 9, 10, 11, 12, 13, 14, 15, 16, 17, 18, 19, 20, 21, or 22, n is an integer from 1 to 350, and where $Z=8.420*Log(V)-4.048$, where V is the kinematic viscosity of the polyalpha-olefin measured at 100° C. in cSt Alternatively, this invention relates to a polyalpha-olefin comprising more than 50 mole % of one or more C5 to C24 alpha-olefin monomers where the polyalpha-olefin has:

a) 40 mole % or less of mm triads, b) a Bromine number of Y or greater, where Y is equal to $89.92*(V)^{-0.5863}$, where V is the kinematic viscosity in cSt measured at 100° C., and c) 1,2 disubstituted olefins present at Z mole % or more where $Z=8.420*Log(V)-4.048$ where V is the kinematic viscosity of the polyalphaolefin in cSt measured at 100° C.

Alternately, this invention relates to a polyalpha-olefin comprising more than 50 mole % of one or more C5 to C24 alpha-olefin monomers where the polyalpha-olefin has 40 mole % or more of mm triads and less than 300 ppm of a Group 4 metal.

Alternately, this invention relates to a polyalpha-olefin comprising more than 50 mole % of one or more C5 to C24 alpha-olefin monomers where the polyalpha-olefin has 40 mole % or more of mm triads and less than 1000 ppm of a Group 13 metal, preferably less than 1000 pm of aluminum and/or boron.

Alternately, this invention relates to a polyalpha-olefin comprising more than 50 mole % of one or more C5 to C24 alpha-olefin monomers where the polyalpha-olefin has 40 mole % or more of mm triads and less than 1000 ppm of aluminum and boron.

Alternately, this invention relates to a polyalpha-olefin comprising more than 50 mole % of one or more C5 to C24 alpha-olefin monomers, where the polyalpha-olefin has 40 mole % or more of mm triads and less than 100 ppm of a Group 13 metal.

Alternately, this invention relates to a polyalpha-olefin comprising more than 50 mole % of one or more C5 to C24 alpha-olefin monomers, where the polyalpha-olefin has 40 mole % or more of mm triads and less than 1000 ppm of aluminum.

Alternately, this invention relates to a polyalpha-olefin comprising more than 50 mole % of one or more C5 to C24 alpha-olefin monomers, where the polyalpha-olefin has 40 mole % or more of mm triads and less than 600 ppm of aluminum.

Alternatively, this invention relates to a hydrogenated polyalpha-olefin comprising more than 50 mole % of one or more C5 to C24 alpha-olefin monomers, where the polyalpha-olefin has mm triads ranging from 95% to 20% mm triads and less than 1000 ppm of group 13 metals, preferably less than 1000 ppm of aluminum and/or boron.

Alternatively, this invention relates to a hydrogenated polyalpha-olefin comprising more than 50 mole % of one or more C5 to C24 alpha-olefin monomers, where the polyalpha-olefin has mm triads ranging from 95% to 20% mm triads and less than 1000 ppm of group 13 metals, preferably less than 1000 ppm of aluminum and/or boron.

Alternatively, this invention relates to a polyalpha-olefin comprising more than 50 mole % C5 to C24 alpha-olefin monomers and having an Mw of 100,000 or less and an Mw/Mn of greater than 1 and less than 2.5.

This invention also relates to process to produce such polyalpha-olefins comprising contacting the C5 to C20 monomers with a metallocene catalyst (preferably a racemic metallocene catalyst), an activator (preferably an alumoxane and or a non-coordinating anion) and, optionally an alkylaluminum compound.

This invention also relates to process to produce such polyalpha-olefins comprising contacting C5 to C20 monomers with a metallocene catalyst and an activator, preferably a racemic metallocene catalyst with an alumoxane or NCA as activator, or a substituted metallocene catalyst with an NCA activator, or a meso metallocene with an NCA activator. In all cases, optionally a co-activator such as an alkylaluminum compound mat be used.

Further, these polyalpha-olefins (and any polyalpha-olefins described herein) may be hydrogenated by contacting the polyalpha-olefin with hydrogen and a hydrogenation catalyst. This hydrogenation step is often used to reduce the bromine number and/or to modify the amount of mm triads in the final poly-alpha-olefins.

DETAILED DESCRIPTION OF THE INVENTION

Figure 1:
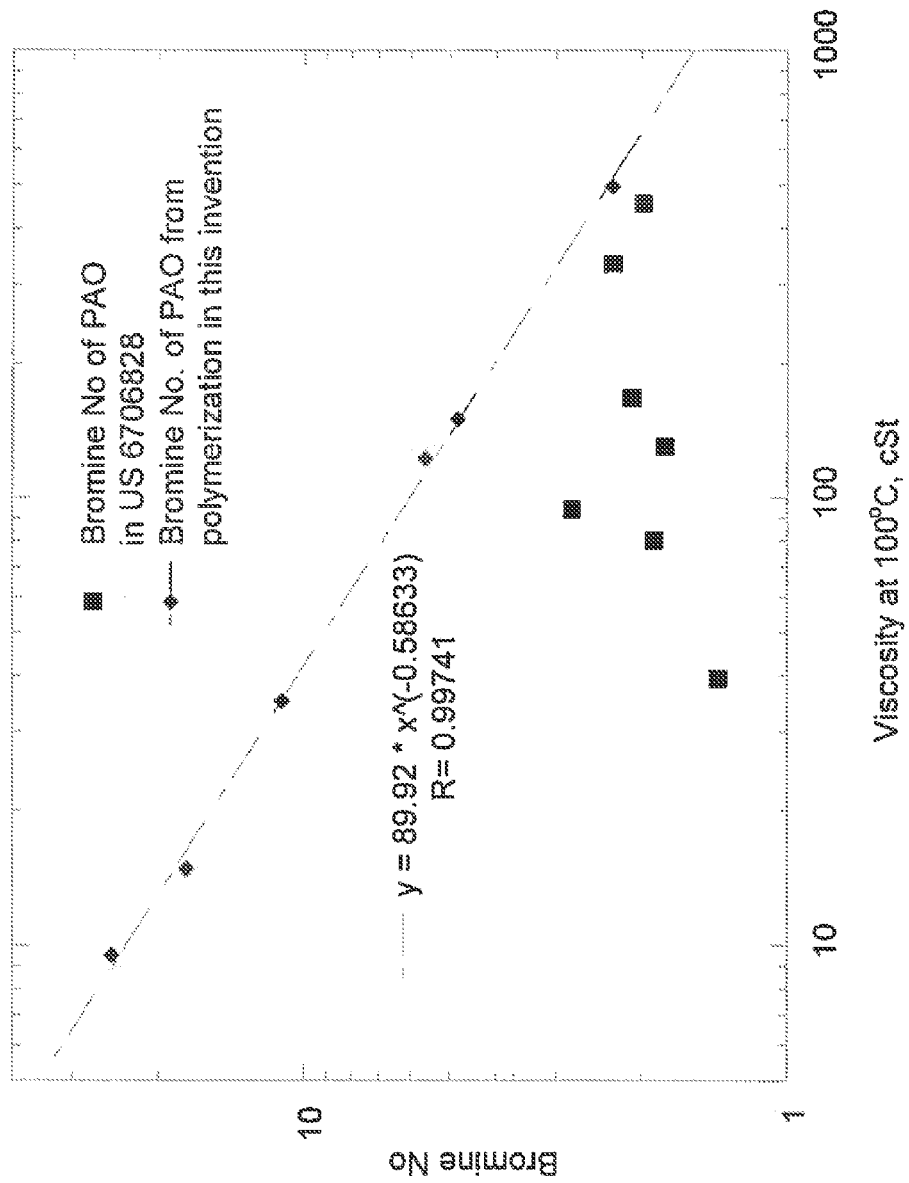
FIG. 1 is a graph of bromine number versus KV100 for certain PAO's from the examples and U.S. Pat. No. 6,706,828.

As used herein, the new numbering scheme for the Periodic Table of the Elements is used as set out in CHEMICAL AND ENGINEERING NEWS, 63(5), 27 (1985).

For purposes of this invention and the claims thereto, when a polymer or oligomer is referred to as comprising an olefin, the olefin present in the polymer or oligomer is the polymerized or oligomerized form of the olefin, respectively. Likewise the use of the term polymer is meant to encompass homopolymers and copolymers, where copolymers include any polymer having two or more chemically distinct monomers. Likewise the use of the term oligomer is meant to encompass homooligomers and cooligomers, where cooligomers include any oligomer or having two or more chemically distinct monomers.

For the purposes of this invention and the claims thereto the term "Polyalpha-olefin," "polyalphaolefin," or "PAO" includes homooligomers, cooligomers, homopolymers and copolymers of alpha-olefin monomers.

For the purposes of this invention and the claims thereto the active species in a catalytic cycle may comprise the neutral or ionic forms of the catalyst.

The term "catalyst system" is defined to mean a catalyst precursor/activator pair, such as a metallocene/activator pair. When "catalyst system" is used to describe such a pair before activation, it means the unactivated catalyst (precatalyst) together with an activator and, optionally, a co-activator (such as a trialkylaluminum compound). When it is used to describe such a pair after activation, it means the activated catalyst and the activator or other charge-balancing moiety. Additionally, the catalyst system may optionally comprise a co-activator and/or other charge-balancing moiety.

"Catalyst precursor" is also often referred to as precatalyst, catalyst, precursor, metallocene, transition metal compound, unactivated catalyst, or transition metal complex. These words are used interchangeably. Activator and cocatalyst are also used interchangeably. A scavenger is a compound that is typically added to facilitate oligomerization or polymerization by scavenging impurities. Some scavengers may also act as activators and may be referred to as co-activators. A co-activator which is not a scavenger may also be used in conjunction with an activator in order to form an active catalyst with a transition metal compound. In some embodiments, a co-activator can be pre-mixed with the transition metal compound to form an alkylated transition metal compound, also referred to as an alkylated catalyst compound or alkylated metallocene.

For purposes of this invention and the claims thereto non-coordinating anion (NCA) is defined to mean an anion which either does not coordinate to the catalyst metal cation or that coordinates only weakly to the metal cation. An NCA coordinates weakly enough that a neutral Lewis base, such as an olefinically or acetylenically unsaturated monomer, can displace it from the catalyst center. Any metal or metalloid that can form a compatible, weakly coordinating complex with the catalyst metal cation may be used or contained in the noncoordinating anion. Suitable metals include, but are not limited to, aluminum, gold, and platinum. Suitable metalloids include, but are not limited to, boron, aluminum, phosphorus, and silicon. A subclass of non-coordinating anions comprises stoichiometric activators, which can be either neutral or ionic. The terms ionic activator, and stoichiometric ionic activator can be used interchangeably. Likewise, the terms neutral stoichiometric activator and Lewis acid activator can be used interchangeably.

In addition, a reactor is any container(s) in which a chemical reaction occurs.

Polyalpha-Olefins

In a preferred embodiment, this invention relates to poly-alpha-olefins (PAO's) comprising more than 50 mole % of one or more C5 to C24 alpha-olefin monomers, preferably 55 mole % or more, preferably 60 mole % or more, preferably 65 mole % or more, preferably 70 mole % or more, preferably 75 mole % or more, preferably 80 mole % or more, preferably 85 mole % or more, preferably 90 mole % or more, preferably 95 mole % or more, preferably 100 mole % based on the total moles of monomers present in the polyalpha-olefin, as measured by Carbon-13 NMR.

In another embodiment this invention further relates to PAO's having 40 mole % or more of mm triads, preferably 45% or more, preferably 50% or more, preferably 55% or more, preferably 60% or more, preferably 65% or more, preferably 70% or more, preferably 75% or more, preferably 80% or more, preferably 85% or more, preferably 90% or more, preferably 95% or more, as determined by Carbon-13 Nuclear Magnetic Resonance (NMR) spectroscopy according to the procedure below.

In another embodiment, the polyalphaolefins according to the present invention have at least about 84 mole % mm triads. In yet other embodiments, the PAO's have at least about 98 mole % mm triads. In one embodiment, the polyalphaolefins according to the present invention have a ratio of mm to mr triads ranging from about 49 to about 1.0. In one embodiment, the preferred range is from 1.0 to 10.0, or from 2 to 49, or from 2 to 18, with more preferred ranges of from 1.0 to 8 or from 8 to 49, as measured by Carbon 13 NMR.

In another embodiment, this invention further related to hydrogenated PAO's having 90% or less mm triads, preferably 70% mm triads or less, preferably 50% mm triads or less, preferably 30% or less mm triads, or preferably 10% mm triads or less.

In another embodiment, the hydrogenated polyalphaolefins according to the present invention have a ratio of mm to mr triads of less than 1, with preferred range from 0.01 to 0.9.

NMR spectroscopy provides key structural information about the synthesized polymers. Proton NMR analysis of the unhydrogenated PAO gives a quantitative breakdown of the olefinic structure types (viz. vinyl, 1,2-disubstituted, trisubstituted, and vinylidene). As noted above, Carbon-13 NMR is used to determine tacticity of the polyalphaolefins of the present invention—quantitatively in some cases, and qualitatively in others. Carbon-13 NMR can be used to determine the concentration of the triads, denoted mm (meso, meso), mr (meso, racemic) and rr (racemic, racemic), as well as molar composition of the sample. The concentrations of these triads defines whether the polymer is isotactic, atactic or syndiotactic. Spectra for a PAO sample are acquired in the following manner. Approximately 100-1000 mg of the PAO sample is dissolved in 2-3 ml of chloroform-d for Carbon 13 analysis. Approximately ~10 mg/ml (solvent basis) of chromium acetylacetonate relaxation agent, $Cr(acac)_3$, is added to the sample to enhance the data acquisition rate. Analysis of the spectra is performed according to the paper by Kim, I.; Zhou, J.-M.; and Chung, H. *Journal of Polymer Science: Part A: Polymer Chemistry* 2000, 38 1687-1697, augmented by the identification and integration of end group resonances, and removal of their contributions to the peaks used in the analysis. The deconvolutions are executed with Acorn NMR Inc.'s NutsPro NMR data analysis software, using an 85/15 Lorentzian/Gaussian lineshape. The component peaks are lumped together into clusters according to the mm, mr, and rr triad assignments, and fit with a Bernoullian distribution. The adjustable parameter for these fits is $P_r$, the fraction of monomer added with racemic stereochemistry. For details of going from a set of triad measurements (such as described by Kim above) to a statistical model (such as the Bernoullian) see "Polymer Sequence Determination, James C. Randall, Academic Press, New York, 1977"

In another embodiment, any of the polyalpha-olefins produced herein preferably have a Bromine number of Y or greater, where Y is equal to $89.92 \times (V)^{-0.5863}$, where V is the Kinematic Viscosity at 100° C. ($KV_{100}$) of the polyalpha-olefin and where $KV_{100}$ is measured according to ASTM D 445, preferably a bromine number of Y+1 or greater, preferably Y+2 or greater, preferably Y+3 or greater, preferably Y+4 or greater, where Bromine number is measured by ASTM D 1159.

In another embodiment, any of the polyalpha-olefins produced herein preferably have 1,2 disubstituted olefins present at 7 mole % or more, based upon the total moles of all monomers present in the poly-alpha-olefin as measured by Proton NMR, preferably 8 mole % or more, preferably 9 mole % or more, preferably 10 mole % or more, preferably 15 mole % or more.

In another embodiment, any of the polyalpha-olefins produced herein preferably have 1,2-disubstituted olefins present at Z mole % or more as measured by Proton-NMR, where $Z=8.420*Log(V)-4.048$, where V is the kinematic viscosity of the polyalpha-olefin measured at 100° C. in cSt In another embodiment, any of the polyalpha-olefins produced herein preferably have a Bromine number of 1.8 or less as measured by ASTM D 1159, preferably 1.7 or less, preferably 1.6 or less, preferably 1.5 or less, preferably 1.4 or less, preferably 1.3 or less, preferably 1.2 or less, preferably 1.1 or less, preferably 1.0 or less, preferably 0.5 or less, preferably 0.1 or less.

In another embodiment, any of the polyalpha-olefins produced herein are hydrogenated and have a Bromine number of 1.8 or less as measured by ASTM D 1159, preferably 1.7 or less, preferably 1.6 or less, preferably 1.5 or less, preferably 1.4 or less, preferably 1.3 or less, preferably 1.2 or less, preferably 1.1 or less, preferably 1.0 or less, preferably 0.5 or less, preferably 0.1 or less.

In another embodiment, any of the polyalpha-olefins described herein preferably have Z mole % or more of units represented by the formula:

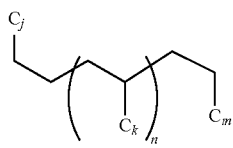

where j, k and m are each, independently, 3, 4, 5, 6, 7, 8, 9, 10, 11, 12, 13, 14, 15, 16, 17, 18, 19, 20, 21, or 22, n is an integer from 1 to 350 (preferably 1 to 300, preferably 5 to 50), as measured by proton NMR and where $Z = 8.420 * \text{Log}(V) - 4.048$, where V is the kinematic viscosity of the polyalpha-olefin measured at 100° C. in cSt, preferably Z is $= 0.990 * V^{(0.627)}$.

The proton NMR analysis (used to measure 1,2-disubstitutions and the units represented by the formula above) is performed by dissolving the sample in appropriate deuterated solvent (e.g. chloroform-d), and acquiring a pulse-acquire experiment of sufficient signal-to-noise ratio to allow integration of the olefin region (approximately 6 ppm-4.6 ppm). The spectra are acquired at a temperature of 50° C., with the temperature chosen to ensure complete sample dissolution (if the sample is not completely dissolved at 50° C., then the temperature is raised slowly until the sample is completely dissolved). The aliphatic region of the proton spectrum comprises the signal from the saturated components, and the olefinic region from the unsaturated end of the polymer. In cases where multiple alphaolefins are copolymerized, it may be possible to determine the composition of the polymer from the branch methyl resonances of the differing alphaolefin branches. This composition determination can be executed if the methyl peaks (resonating between 1.0 and 0.6 ppm) are sufficiently resolved to allow direct integration, or spectral deconvolution.

The olefinic region can be integrated piecewise according to the chemical shift assignments tabulated below:

| Olefin type | Chemical shift range (ppm) | Number of protons |
| --- | --- | --- |
| Vinyl | 5.7-5.9 | 1 |
|  | 4.8-5.3 | 2 |
| 1,2-disubstituted | 5.3-5.6 | 2 |
| Trisubstituted | 4.8-5.3 | 1 |
| Vinylidene (1,1-disubstituted) | 4.6-4.8 | 2 |

The olefin subintegrals are corrected for the proton multiplicity of the contributing species, and for overlapping contributions (e.g. both vinyl and trisubstituted olefins in the 5.3-4.8 ppm region). The integral values resulting from this correction can then be normalized to give the mole-percentage of each olefin class. Comparison of the corrected integral values with the aliphatic integral intensity (also multiplicity-corrected) can be used to determine the olefin concentrations on an absolute basis (e.g. olefins per 1000 carbons).

In another embodiment, any of the polyalpha-olefins described herein preferably have less than 300 ppm of Group 4 metals (preferably Ti, Hf or Zr), preferably less than 200 ppm, preferably less than 100 ppm, preferably less than 50 ppm, preferably less than 10 ppm, as measured by ASTM 5185.

In another embodiment, any of the polyalpha-olefins described herein preferably have less than 300 ppm of Ti, preferably less than 200 ppm, preferably less than 100 ppm, preferably less than 50 ppm, preferably less than 10 ppm, as measured by ASTM 5185.

In another embodiment, any of the polyalpha-olefins described herein preferably have less than 300 ppm of Hf, preferably less than 200 ppm, preferably less than 100 ppm, preferably less than 50 ppm, preferably less than 10 ppm, as measured by ASTM 5185.

In another embodiment, any of the polyalpha-olefins described herein preferably have less than 300 ppm of Zr, preferably less than 200 ppm, preferably less than 100 ppm, preferably less than 50 ppm, preferably less than 10 ppm, as measured by ASTM 5185.

In another embodiment, any of the polyalpha-olefins described herein preferably have less than 100 ppm of Group 13 metals (preferably B or Al), preferably less than 50 ppm, preferably less than 10 ppm, as measured by ASTM 5185.

In another embodiment, any of the polyalpha-olefins described herein preferably have less than 100 ppm of boron, preferably less than 50 ppm, preferably less than 10 ppm, as measured by ASTM 5185.

In another embodiment, any of the polyalpha-olefins described herein preferably have less than 600 ppm of aluminum, preferably less than 500 ppm, preferably less than 600 ppm, preferably less than 300 ppm, preferably less than 300 ppm, preferably less than 10 ppm, preferably less than 50 ppm, preferably less than 10 ppm, as measured by ASTM 5185.

In another embodiment, any of the polyalpha-olefins described herein preferably have an Mw (weight average molecular weight) of 100,000 or less, preferably between 100 and 80,000, preferably between 250 and 60,000, preferably between 280 and 50,000, preferably between 336 and 40,000 g/mol. (Preferred Mw's include those from 224 to 55,100, preferably from 392 to 30,000, preferably 800 to 24,000, preferably 2,000 to 37,5000 g/mol. Alternately preferred Mw's include 224 to about 6790 and 224 to about 2720).

In another embodiment, any of the polyalpha-olefins described herein preferably have an Mn (number average molecular weight) of 50,000 or less, preferably between 200 and 40,000, preferably between 250 and 30,000, preferably between 500 and 20,000 g/mol. (Preferred Mn's include those from 280 to 10,000, preferably form 280 to 4000. Alternately preferred Mn's include those from 200 to 20,900, preferably 280, to 10,000, preferably 200 to 7000, preferably 200 to 2000, preferably 280 to 2900, preferably 280 to 1700, preferably 200 to 500.)

In another embodiment, any of the polyalpha-olefins described herein preferably have an Mw/Mn of greater than 1 and less than 5, preferably less than 4, preferably less than 3, preferably less than 2.5, preferably less than 2. Alternately any of the polyalpha-olefins described herein preferably have an Mw/Mn of between 1 and 2.5, alternately between 1 and 3.5.

The Mw, Mn and Mz are measured by GPC method using a column for medium to low molecular weight polymers, tetrahydrofuran as solvent and polystyrene as calibration standard, correlated with the fluid viscosity according to a power equation.

This relationship of Mw vs. 100° C. viscosity in cSt for fluids prepared in this invention using 1-decene as feed is as following: Mw=352.41×(100° C. vis in cSt)$^{0.5997}$. Similarly, the relationship of Mw vs. 100° C. viscosity in cSt for fluids prepared in this invention using 1-hexene as feed is as following: Mw=234.85*(V)$^{0.6165}$ where V is the kinematic viscosity measured at 100° C. in cSt When other alpha-olefins are used as feed, this Mw vs. 100° C. viscosity relationship may change slightly. It is expected similar type of relationship will hold.

Unless otherwise indicated Mw values reported herein are GPC values and not calculated from KV100.

In a preferred embodiment of this invention, any PAO described herein may have a pour point of less than 0° C. (as measured by ASTM D 97), preferably less than −10° C., preferably less than −20° C., preferably less than −25° C., preferably less than −30° C., preferably less than −35° C., preferably less than −50° C., preferably between −10 and −80° C., preferably between −15° C. and −70° C.

In a preferred embodiment of this invention, any PAO described herein may have a kinematic viscosity (at 40° C. as measured by ASTM D 445) from about 4 to about 50,000 cSt, preferably from about 5 cSt to about 30,000 cSt at 40° C., alternately from about 4 to about 100,000 cSt, preferably from about 6 cSt to about 50,000 cSt, preferably from about 10 cSt to about 30,000 cSt at 40° C.

In another embodiment according to the present invention, any polyalpha olefin described herein may have a kinematic viscosity at 100° C. from about 1.5 to about 5,000 cSt, preferably from about 2 to about 3,000 cSt, preferably from about 3 cSt to about 1,000 cSt, more preferably from about 4 cSt to about 1,000 cSt, and yet more preferably from about 8 cSt to about 500 cSt as measured by ASTM D445. The PAOs preferably have viscosities in the range of 2 to 500 cSt at 100° C. in one embodiment, and from 2 to 3000 cSt at 100° C. in another embodiment, and from 3.2 to 300 cSt in another embodiment. Alternately, the polyalpha-olefin has a $KV_{100}$ of less than 200 cSt.

In another embodiment according to the present invention any polyalpha olefin described herein may have a kinematic viscosity at 100° C. from 3 to 10 cSt and a flash point of 150° C. or more, preferably 200° C. or more (as measured by ASTM D 56).

In another embodiment according to the present invention any polyalpha olefin described herein may have a dielectric constant of 2.5 or less (1 kHz at 23° C. as determined by ASTM D 924).

In another embodiment according to the present invention any polyalpha olefin described herein may have a specific gravity of 0.75 to 0.96 g/cm$^3$, preferably 0.80 to 0.94 g/cm$^3$.

The PAO's prepared herein, particularly those of low viscosity (such as those with a $KV_{100}$ of 10 cSt or less), are especially suitable for high performance automotive engine oil formulations either by themselves or by blending with other fluids, such as Group II, Group II+, Group III, Group III+ or lube base stocks derived from hydroisomerization of wax fractions from Fisher-Tropsch hydrocarbon synthesis from CO/H2 syn gas, or other Group IV or Group V base stocks. PAOs having $KV_{100}$'s from 3 cSt to 8 cSt are also preferred grades for high performance automotive engine oil or industrial oil formulations. The PAO's of 40 to 1000 cSt made in this invention are desirable for use as blend stock with Gr I, II, III, III+ or GTL derived lube base stocks for use in industrial and automotive engine or gear oil, especially certain high $KV_{100}$ grades of 3 to 1000 cSt which are especially desirable for use as blend stock with Gr I, II, III, III+ or GTL derived lube base stocks for use in industrial and automotive engine or gear oil. They are also suitable for use in personal care applications, such as blends with soaps, detergents, other emollients, for use in personal care creams, lotions, sticks, shampoos, detergents, etc.

In another embodiment the PAO's have $KV_{100}$'s ranging from about 42 to about 3045 cSt In another embodiment the PAO's have $KV_{100}$'s ranging from about 32 to about 102 cSt In another embodiment according to the present invention, any polyalpha olefin described herein may have a viscosity index (VI) of 100 or more, preferably 120 or more, preferably 130 or more, alternately, form 120 to 450, alternately from 100 to 400, alternately from 120 to 380, alternately from 100 to 300, alternately from 140 to 380, alternately from 180 to 306, alternately from 252 to 306, alternately the viscosity index is at least about 165, alternately at least about 187, alternately at least about 200, alternately at least about 252. For many lower viscosity fluids made from 1-decene or 1-decene equivalent feeds ($KV_{100}$ of 3 to 10 cSt), the preferred VI range is from 100 to 180. Viscosity index is determined according to ASTM Method D 2270-93 [1998].

All kinematic viscosity values reported for fluids herein are measured at 100° C. unless otherwise noted. Dynamic viscosity can then be obtained by multiplying the measured kinematic viscosity by the density of the liquid. The units for kinematic viscosity are in m$^2$/s, commonly converted to cSt or centistokes (1 cSt=10$^{-6}$ m$^2$/s or 1 cSt=1 mm$^2$/sec).

One embodiment according to the present invention is a new class of poly-alpha-olefins, which have a unique chemical composition characterized by a high percentage of unique head-to-head connections at the end position of the polymer chain and a high degree of stereo-regularity. The new poly-alpha-olefins when used by themselves or blended with other fluids have unique lubrication properties. The term "head-to-head connection" refers to a connection formed on at least one end of the PAO oligomer or polymer in which the penultimate olefin inserted 1,2 and the last olefin inserted 2,1 into the oligomer or polymer chain, as illustrated in the lower scheme in FIG. 3.

Another embodiment according to the present invention is a new class of hydrogenated poly-alpha-olefins having a unique chemical composition which is characterized by a high percentage of unique head-to-head connection at the end position of the polymer and by a reduced degree tacticity compared to the product before hydrogenation. The new poly-alpha-olefins when used by itself or blended with another fluid have unique lubrication properties.

The PAO's produced according to this invention are typically dimers, trimers, tetramers, or higher oligomers of one or more C5 to C24 olefin monomers, preferably one or more C5 to C24 alpha-olefin monomers, preferably one or more C5 to C24 linear alpha-olefin monomers. Alternatively, an alpha-olefin with alkyl substitutent at least 2 carbons away from the olefinic double bond can also be used. Typically, the PAO's produced herein are usually a mixture of many different oligomers. The smallest oligomers from these alpha-olefins have carbon number ranging from C10 to C20. These small oligmers are usually too light for most high performance fluids application. They are usually separated from the higher oligomers with carbon number of greater than C20, for example C24 and higher which are more preferred as high performance fluids. These separated C10 to C20 oligomer olefins or the corresponding paraffins after hydrogenation can be used in specialty applications, such as drilling fluids, solvents, paint thinner, etc with excellent biodegradability, toxicity, viscosities, etc. The high performance fluid fraction in the C20, or C30 and higher fractions typically have lower viscosities making them beneficial for some applications, such as better fuel economy, better biodegradability, better low temperature flow properties, or lower volatility. The higher viscosity product, usually have much higher average degree of polymerization have very low amount of C20 or C30 component. These high viscosity fluids are excellent blend stocks for lube application to improve the viscosity. Because of their usually narrow molecular weight distribution, they have superior shear stability. Because of their unique chemical composition, they have excellent viscometrics and unexpected low traction properties. These higher viscosity PAO can be used as superior blend stocks. They can be blend stocks with any of the Gr I, II, III, III+, GTL and Gr V fluids to give the optimum viscometrics, solvency, high and low temperature lubricity, etc. When further blended with proper additives, including antioxidants, antiwear additives, friction modifiers, dispersants, detergents, corrosion inhibitors, defoamants, extreme pressure additives, seal swell additives, and optionally viscosity modifiers, etc. Description of typical additives can be found in the book "Lubricant Additives" Chemistry and Applications, ed. L. R. Rudnick, Marcel Dekker, Inc., New York, 2003.

Process

One embodiment of the present invention discloses an improved process to produce a new class of poly-alpha-olefins having unique chemical compositions. This improved process employs metallocene catalysts together with one or more activators (such as an alumoxane or a non-coordinating anion). The metallocene catalyst can be a bridged or unbridged, substituted or unsubstituted cyclopentadienyl, indenyl or fluorenyl compound. One preferred class of catalysts are highly substituted metallocenes that give high catalyst productivity and higher product viscosity. Another preferred class of metallocenes are bridged and substituted cyclopentadienes. Another preferred class of metallocenes are bridged and substituted indenes or fluorenes. One aspect of the processes described herein also includes treatment of the feed olefins to remove catalyst poisons, such as peroxides, oxygen, sulfur, nitrogen-containing organic compounds, and or acetylenic compounds. This treatment is believed to increase catalyst productivity, typically more than 5 fold, preferably more than 10 fold.

In a preferred embodiment, this invention relates to a process to produce a polyalpha-olefin comprising:

1) contacting at least one alpha-olefin monomer having 5 to 24 carbon atoms with a racemic metallocene compound (preferably a highly substituted compound) and an activator under polymerization conditions wherein hydrogen, if present, is present at a partial pressure of 200 psi (1379 kPa) or less, based upon the total pressure of the reactor (preferably 150 psi (1034 kPa) or less, preferably 100 psi (690 kPa) or less, preferably 50 psi (345 kPa) or less, preferably 25 psi (173 kPa) or less, preferably 10 psi (69 kPa) or less (alternately the hydrogen, if present is present in the reactor at 1000 ppm or less by weight, preferably 750 ppm or less, preferably 500 ppm or less, preferably 250 ppm or less, preferably 100 ppm or less, preferably 50 ppm or less, preferably 25 ppm or less, preferably 10 ppm or less, preferably 5 ppm or less), and wherein the alpha-olefin monomer having 5 to 24 carbon atoms is present at 10 volume % or more based upon the total volume of the catalyst/activator/co-activator solutions, monomers, and any diluents or solvents present in the reaction; and 2) obtaining a polyalpha-olefin, optionally hydrogenating the PAO, and obtaining a PAO, comprising at least 50 mole % of a C5 to C24 alpha-olefin monomer, wherein the polyalpha-olefin has a kinematic viscosity at 100° C. of 5000 cSt or less, and the polyalpha-olefin comprises Z mole % or more of units represented by the formula:

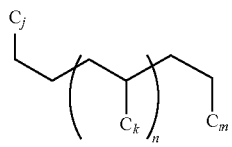

where j, k and m are each, independently, 3, 4, 5, 6, 7, 8, 9, 10, 11, 12, 13, 14, 15, 16, 17, 18, 19, 20, 21, or 22, n is an integer from 1 to 350, and where $Z=8.420*Log(V)-4.048$, where V is the Kinematic viscosity of the polyalpha-olefin measured at 100° C. in cSt.

In an alternate embodiment, this invention relates to a process to produce a polyalpha-olefin comprising:

1) contacting a feed stream comprising at least one alpha-olefin monomer having 5 to 24 carbon atoms with a metallocene catalyst compound and a non-coordinating anion activator or alkylalumoxane activator, and optionally an alkylaluminum compound, under polymerization conditions wherein the alpha-olefin monomer having 5 to 24 carbon atoms is present at 10 volume % or more based upon the total volume of the catalyst/activator/co-activator solution, monomers, and any diluents or solvents present in the reactor and where the feed alpha-olefin, diluent or solvent stream comprises less than 300 ppm of heteroatom containing compounds; and obtaining a polyalpha-olefin comprising at least 50 mole % of a C5 to C24 alpha-olefin monomer where the polyalpha-olefin has a kinematic viscosity at 100° C. of 5000 cSt or less. Preferably, hydrogen, if present is present in the reactor at 1000 ppm or less by weight, preferably 750 ppm or less, preferably 500 ppm or less, preferably 250 ppm or less, preferably 100 ppm or less, preferably 50 ppm or less, preferably 25 ppm or less, preferably 10 ppm or less, preferably 5 ppm or less.

In an alternate embodiment, this invention relates to a process to produce a polyalpha-olefin comprising:

1) contacting a feed stream comprising at least one alpha-olefin monomer having 5 to 24 carbon atoms with a metallocene catalyst compound and a non-coordinating anion activator or alkylalumoxane activator, and optionally an alkylaluminum compound, under polymerization conditions wherein the alpha-olefin monomer having 5 to 24 carbon atoms is present at 10 volume % or more based upon the total volume of the catalyst/activator/co-activator solution, monomers, and any diluents or solvents present in the reactor and where the feed alpha-olefin, diluent or solvent stream comprises less than 300 ppm of heteroatom containing compounds which; and obtaining a polyalpha-olefin comprising at least 50 mole % of a C5 to C24 alpha-olefin monomer where the polyalpha-olefin has a kinematic viscosity at 100° C. of 5000 cSt or less;

2) isolating the lube fraction polymers and then contacting this lube fraction with hydrogen under typical hydrogenation conditions with hydrogenation catalyst to give fluid with bromine number below 1.8, or alternatively, isolating the lube fraction polymers and then contacting this lube fraction with hydrogen under more severe conditions with hydrogenation catalyst to give fluid with bromine number below 1.8 and with reduce mole % of mm components than the unhydrogenated polymers.

Alternately, in any process described herein hydrogen, if present, is present in the reactor at 1000 ppm or less by weight, preferably 750 ppm or less, preferably 500 ppm or less, preferably 250 ppm or less, preferably 100 ppm or less, preferably 50 ppm or less, preferably 25 ppm or less, preferably 10 ppm or less, preferably 5 ppm or less.

Alternately, in any process described herein hydrogen, if present, is present in the feed at 1000 ppm or less by weight, preferably 750 ppm or less, preferably 500 ppm or less, preferably 250 ppm or less, preferably 100 ppm or less, preferably 50 ppm or less, preferably 25 ppm or less, preferably 10 ppm or less, preferably 5 ppm or less.

Unless otherwise stated all pressures in psi are psig.

Metallocene Catalyst Compounds

For purposes of this invention and the claims thereto, the terms "hydrocarbyl radical," "hydrocarbyl," and hydrocarbyl group" are used interchangeably throughout this document. Likewise the terms "group," "radical," and "substituent" are also used interchangeably throughout this document. For purposes of this disclosure, "hydrocarbyl radical" is defined to be a $C_1$-$C_{100}$ radical and may be linear, branched, or cyclic. When cyclic, the hydrocarbon radical may be aromatic or non-aromatic. "Hydrocarbon radical" is defined to include substituted hydrocarbyl radicals, halocarbyl radicals, substituted halocarbyl radicals, silylcarbyl radicals, and germylcarbyl radicals as these terms are defined below. Substituted hydrocarbyl radicals are radicals in which at least one hydrogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-hydrocarbon atom or group has been inserted within the hydrocarbyl radical, such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical, and two or more R* may join together to form a substituted or unsubstituted saturated, partially unsaturated or aromatic cyclic or polycyclic ring structure.

Halocarbyl radicals are radicals in which one or more hydrocarbyl hydrogen atoms have been substituted with at least one halogen (e.g. F, Cl, Br, I) or halogen-containing group (e.g. $CF_3$).

Substituted halocarbyl radicals are radicals in which at least one halocarbyl hydrogen or halogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-carbon atom or group has been inserted within the halocarbyl radical such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical provided that at least one halogen atom remains on the original halocarbyl radical. Additionally, two or more R* may join together to form a substituted or unsubstituted saturated, partially unsaturated or aromatic cyclic or polycyclic ring structure.

Silylcarbyl radicals (also called silylcarbyls) are groups in which the silyl functionality is bonded directly to the indicated atom or atoms. Examples include $SiH_3$, $SiH_2R^*$, $SiHR^*_2$, $SiR^*_3$, $SiH_2(OR^*)$, $SiH(OR^*)_2$, $Si(OR^*)_3$, $SiH_2(NR^*_2)$, $SiH(NR^*_2)_2$, $Si(NR^*_2)_3$, and the like where R* is independently a hydrocarbyl or halocarbyl radical and two or more R* may join together to form a substituted or unsubstituted saturated, partially unsaturated or aromatic cyclic or polycyclic ring structure.

Germylcarbyl radicals (also called germylcarbyls) are groups in which the germyl functionality is bonded directly to the indicated atom or atoms. Examples include $GeH_3$, $GeH_2R^*$, $GeHR^*_2$, $GeR^5_3$, $GeH_2(OR^*)$, $GeH(OR^*)_2$, $Ge(OR^*)_3$, $GeH_2(NR^*_2)$, $GeH(NR^*_2)_2$, $Ge(NR^*_2)_3$, and the like where R* is independently a hydrocarbyl or halocarbyl radical and two or more R* may join together to form a substituted or unsubstituted saturated, partially unsaturated or aromatic cyclic or polycyclic ring structure.

Polar radicals or polar groups are groups in which a heteroatom functionality is bonded directly to the indicated atom or atoms. They include heteroatoms of groups 1-17 of the periodic table (except carbon and hydrogen) either alone or connected to other elements by covalent bonds or other interactions such as ionic bonds, van der Waals forces, or hydrogen bonding. Examples of functional heteroatom containing groups include carboxylic acids, acid halides, carboxylic esters, carboxylic salts, carboxylic anhydrides, aldehydes and their chalcogen (Group 14) analogues, alcohols and phenols, ethers, peroxides and hydroperoxides, carboxylic amides, hydrazides and imides, amidines and other nitrogen analogues of amides, nitriles, amines and imines, azos, nitros, other nitrogen compounds, sulfur acids, selenium acids, thiols, sulfides, sulfoxides, sulfones, phosphines, phosphates, other phosphorus compounds, silanes, boranes, borates, alanes, aluminates. Functional groups may also be taken broadly to include organic polymer supports or inorganic support material such as alumina, and silica. Preferred examples of polar groups include $NR^*_2$, $OR^*$, $SeR^*$, $TeR^*$, $PR^*_2$, $AsR^*_2$, $SbR^*_2$, $SR^*$, $BR^*_2$, $SnR^*_3$, $PbR^*_3$ and the like where R* is independently a hydrocarbyl, substituted hydrocarbyl, halocarbyl or substituted halocarbyl radical as defined above and two R* may join together to form a substituted or unsubstituted saturated, partially unsaturated or aromatic cyclic or polycyclic ring structure.

In using the terms "substituted or unsubstituted cyclopentadienyl ligand", "substituted or unsubstituted indenyl ligand", and "substituted or unsubstituted tetrahydroindenyl ligand", the substitution to the aforementioned ligand may be hydrocarbyl, substituted hydrocarbyl, halocarbyl, substituted halocarbyl, silylcarbyl, or germylcarbyl. The substitution may also be within the ring giving heterocyclopentadienyl ligands, heteroindenyl ligands or heterotetrahydroindenyl ligands, each of which can additionally be substituted or unsubstituted.

In some embodiments, the hydrocarbyl radical is independently selected from methyl, ethyl, ethenyl, and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, triacontynyl, butadienyl, pentadienyl, hexadienyl, heptadienyl, octadienyl, nonadienyl, and decadienyl. Also included are isomers of saturated, partially unsaturated and aromatic cyclic and polycyclic structures wherein the radical may additionally be subjected to the types of substitutions described above. Examples include phenyl, methylphenyl, dimethylphenyl, ethylphenyl, diethylphenyl, propylphenyl, dipropylphenyl, benzyl, methylbenzyl, naphthyl, anthracenyl, cyclopentyl, cyclopentenyl, cyclohexyl, cyclohexenyl, methylcyclohexyl, cycloheptyl, cycloheptenyl, norbornyl, norbornenyl, adamantyl and the like. For this disclosure, when a radical is listed, it indicates that radical type and all other radicals formed when that radical type is subjected to the substitutions defined above. Alkyl, alkenyl and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl. Examples of cyclopentadienyl and indenyl ligands are illustrated below as anionic ligands. The ring numbering scheme is also illustrated.

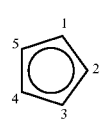
Cyclopentadienyl

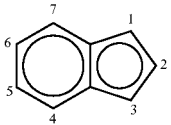
Indenyl

A similar numbering and nomenclature scheme is used for heteroindenyl as illustrated below where Z and Q independently represent the heteroatoms O, S, Se, or Te, or heteroatom groups, NR', PR', AsR', or SbR' where R' is hydrogen, or a hydrocarbyl, substituted hydrocarbyl, halocarbyl, substituted halocarbyl, silylcarbyl, or germylcarbyl substituent. The number scheme shown below is for heteroindenyl ligands that are bridged to another ligand via a bridging group.

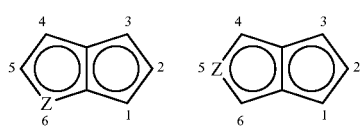

Examples include:
Cyclopenta[b]thienyl (Z=S)
Cyclopenta[b]furanyl (Z=O)
Cyclopenta[b]selenophenyl (Z=Se)
Cyclopenta[b]tellurophenyl (Z=Te)
6-Methyl-cyclopenta[b]pyrrolyl (Z=N—Me)
6-Methyl-cyclopenta[b]phospholyl (Z=P—Me)
6-Methyl-cyclopenta[b]arsolyl (Z=As—Me)
6-Methyl-cyclopenta[b]stibolyl (Z=Sb—Me)
Examples include:
Cyclopenta[c]thienyl (Z=C)
Cyclopenta[c]furanyl (Z=O)
Cyhclopenta[c]selenophenyl (Z=Se)
Cyclopenta[c]tellurophenyl (Z=Te)
5-Methyl-cyclopenta[c]pyrrolyl (Z=N—Me)
5-Methyl-cyclopenta[c]phospholyl (Z=P—Me)
5-Methyl-cyclopenta[c]arsolyl (Z=As—Me)
5-Methyl-cyclopenta[c]stibolyl (Z=Sb—Me)

A similar numbering and nomenclature scheme is used for heterocyclopentadienyl rings as illustrated below where G and J independently represent the heteroatoms N, P, As, Sb or B. For these ligands when bridged to another ligand via a bridging group, the one position is usually chosen to be the ring carbon position where the ligand is bonded to the bridging group, hence a numbering scheme is not illustrated below.

Examples include:
Azacyclopentadiene (G=N)
Phosphacyclopentadiene (G=P)
Stibacyclopentadiene (G=Sb)
Arsacyclopentadiene (G=As)
Boracyclopentadiene (G=B)

Depending on the position of the bridging ligand, the numbering for the following ligands will change; 1,3 and 1,2 are only used in this case to illustrate the position of the heteroatoms relative to one another.

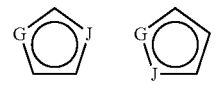

Examples include:
1,3-Diazacyclopentadiene (G=J=N)
1,3-Diphosphacyclopentadiene (G=J=P)
1,3-Distibacyclopentadiene (G=J=Sb)
1,3-Diarsacyclopentadiene (G=J=As)
1,3-Diboracyclopentadiene (G=J=B)
1,3-Azaphosphacyclopentadiene (G=N; J=P)
1,3-Azastibacyclopentadiene (G=N; J=Sb)
1,3-Azarsacyclopentadiene (G=N; J=As)
1,3-Azaboracyclopentadiene (G=N; J=B)
1,3-Arsaphosphacyclopentadiene (G=As; J=P)
1,3-Arsastibacyclopentadiene (G=As; J=Sb)
1,3-Arsaboracyclopentadiene (G=As; J=B)
1,3-Boraphosphacyclopentadiene (G=B; J=P)
1,3-Borastibacyclopentadiene (G=B; J=Sb)
1,3-Phosphastibacyclopentadiene (G=P; J=Sb)
Examples include:
1,2-Diazacyclopentadiene (G=J=N)
1,2-Diphosphacyclopentadiene (G=J=P)
1,2-Distibacyclopentadiene (G=J=Sb)
1,2-Diarsacyclopentadiene (G=J=As)
1,2-Diboracyclopentadiene (G=J=B)
1,2-Azaphosphacyclopentadiene (G=N; J=P)
1,2-Azastibacyclopentadiene (G=N; J=Sb)

1,2-Azarsacyclopentadiene (G=N; J=As)
1,2-Azaboracyclopentadiene (G=N; J=B)
1,2-Arsaphosphacyclopentadiene (G=As; J=P)
1,2-Arsastibacyclopentadiene (G=As; J=Sb)
1,2-Arsaboracyclopentadiene (G=As; J=B)
1,2-Boraphosphacyclopentadiene (G=B; J=P)
1,2-Borastibacyclopentadiene (G=B: J=Sb)
1,2-Phosphastibacyclopentadiene (G=P; J=Sb)

A "ring heteroatom" is a heteroatom that is within a cyclic ring structure. A "heteroatom substituent" is heteroatom containing group that is directly bonded to a ring structure through the heteroatom. A "bridging heteroatom substituent" is a heteroatom or heteroatom group that is directly bonded to two different ring structures through the heteroatom. The terms "ring heteroatom", "heteroatom substituent", and "bridging heteroatom substituent" are illustrated below where Z and R' are as defined above. It should be noted that a "heteroatom substituent" can be a "bridging heteroatom substituent" when R' is additionally defined as the ligand "A".

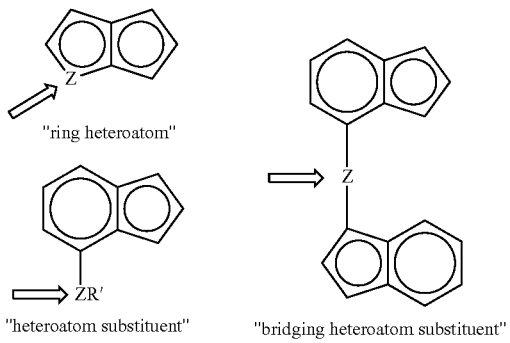

A "ring carbon atom" is a carbon atom that is part of a cyclic ring structure. By this definition, an indenyl ligand has nine ring carbon atoms; a cyclopentadienyl ligand has five ring carbon atoms.

Transition metal compounds have symmetry elements and belong to symmetry groups. These elements and groups are well established and can be referenced from Chemical Appellations of Group Theory (2nd Edition) by F. Albert Cotton, Wiley-Interscience, 1971. Pseudo-symmetry, such as a pseudo $C_2$-axis of symmetry refers to the same symmetry operation, however, the substituents on the ligand frame do not need to be identical, but of similar size and steric bulk. Substituents of similar size are typically within 4 atoms of each other, and of similar shape. For example, methyl, ethyl, n-propyl, n-butyl and iso-butyl substituents (e.g. C1-C4 primary bonded substituents) would be considered of similar size and steric bulk. Likewise, iso-propyl, sec-butyl, 1-methylbutyl, 1-ethylbutyl and 1-methylpentyl substituents (e.g. C3-C6 secondary bonded substituents) would be considered of similar size and steric bulk. Tert-butyl, 1,1-dimethylpropyl, 1,1-dimethylbutyl, 1,1-dimethylpentyl and 1-ethyl-1-methylpropyl (e.g. C4-C7 tertiary bonded substituents) would be considered of similar size and steric bulk. Phenyl, tolyl, xylyl, and mesityl substituents (C6-C9 aryl substituents) would be considered of similar size and steric bulk. Additionally, the bridging substituents of a compound with a pseudo $C_2$-axis of symmetry do not have to be similar at all since they are far removed from the active site of the catalyst. Therefore, a compound with a pseudo $C_2$-axis of symmetry could have for example, a Me$_2$Si, MeEtSi or MePhSi bridging ligand, and still be considered to have a pseudo $C_2$-axis of symmetry given the appropriate remaining ligand structure. In some embodiments, metallocenes with a $C_1$-axis of symmetry may also be useful herein.

For purposes of this disclosure, the term oligomer refers to compositions having 2-75 mer units and the term polymer refers to compositions having 76 or more mer units. A mer is defined as a unit of an oligomer or polymer that originally corresponded to the olefin(s) used in the oligomerization or polymerization reaction. For example, the mer of polydecene would be decene.

The metallocene compounds (pre-catalysts), useful herein are preferably cyclopentadienyl derivatives of titanium, zirconium and hafnium. In general, useful titanocenes, zirconocenes and hafnocenes may be represented by the following formulae:

$$(Cp\text{-}A'\text{-}Cp^*)MX_1X_2 \qquad (1)$$

$$(CpCp^*)MX_1X_2 \qquad (2)$$

wherein:
M is the metal center, and is a Group 4 metal preferably titanium, zirconium or hafnium, preferably zirconium or hafnium;
Cp and Cp* are the same or different cyclopentadienyl rings that are each bonded to M, and substituted with from zero to four substituent groups S" for formula (1) and zero to five substituents for formula (2), each substituent group S" being, independently, a radical group which is a hydrocarbyl, substituted hydrocarbyl, halocarbyl, substituted halocarbyl, silylcarbyl or germylcarbyl, or Cp and Cp* are the same or different cyclopentadienyl rings in which any two adjacent S" groups are optionally joined to form a substituted or unsubstituted, saturated, partially unsaturated, or aromatic cyclic or polycyclic substituent; A' is a bridging group; $X_1$ and $X_2$ are, independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; or when Lewis-acid activators, such as methylalumoxane, which are capable of donating an X ligand as described above to the transition metal component are used, both X may, independently, be a halogen, alkoxide, aryloxide, amide, phosphide or other univalent anionic ligand or both X can also be joined to form a anionic chelating ligand.

In a preferred embodiment the metallocene is racemic which means in a preferred embodiment, that the compounds represented by formula (1) [(Cp-A'-Cp*)MX$_1$X$_2$] have no plane of symmetry containing the metal center, M; and have a $C_2$-axis of symmetry or pseudo $C_2$-axis of symmetry through the metal center. Preferably in the racemic metallocenes represented by formula (1) A' is selected from R'$_2$C, R'$_2$Si, R'$_2$Ge, R'$_2$CCR'$_2$, R'$_2$CCR'$_2$CR'$_2$, R'$_2$CCR'$_2$CR'$_2$CR'$_2$, R'C=CR', R'C=CR'CR'$_2$, R'$_2$CCR'=CR'CR'$_2$, R'C=CR'CR'=CR', R'C=CR'CR'$_2$CR'$_2$, R'$_2$CSiR'$_2$, R'$_2$SiSR'$_2$, R'$_2$CSiR'$_2$CR'$_2$, R'$_2$SiCR'$_2$SiR'$_2$, R'C=CR'SiR'$_2$, R'$_2$CGeR'$_2$, R'$_2$GeGeR'$_2$, R'$_2$CGeR'$_2$CR'$_2$, R'$_2$GeCR'$_2$GeR'$_2$, R'$_2$SiGeR'$_2$, R'C=CR'GeR'$_2$, R'B, R'$_2$C—BR', R'$_2$C—BR'—CR'$_2$, R'N, R'P, O, S, Se, R'$_2$C—O—CR'$_2$, R'$_2$CR'$_2$C—O—CR'$_2$CR'$_2$, R'$_2$C—O—CR'$_2$CR'$_2$, R'$_2$C—O—CR'=CR', R'$_2$C—S—CR'$_2$, R'$_2$CR'$_2$C—S—CR'$_2$CR'$_2$, R'$_2$C—S—CR'$_2$CR'$_2$, R'$_2$C—S—CR'=CR', R'$_2$C—Se—CR'$_2$, R'$_2$CR'$_2$C—Se—CR'$_2$CR'$_2$, R'$_2$C—Se—CR'$_2$CR'$_2$, R'$_2$C—Se—CR'$_2$, Se—CR'=CR', R'$_2$C—N=CR', R'$_2$C—NR'—CR'$_2$, R'$_2$C—NR'—CR'$_2$CR'$_2$, R'$_2$C—NR'—CR'=CR', R'$_2$CR'$_2$C—

NR'—CR'$_2$CR'$_2$, R'$_2$C—P=CR', and R'$_2$C—PR'—CR'$_2$ where when Cp is different than Cp* then R' is a C1-C5 containing hydrocarbyl, substituted hydrocarbyl, halocarbyl, substituted halocarbyl, silylcarbyl or germylcarbyl substituent, and when Cp is the same as Cp* then R' is selected from hydrogen, C1-C20 containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated, cyclic or polycyclic substituent.

Table A depicts representative constituent moieties for the metallocene components of formula 1 and 2. The list is for illustrative purposes only and should not be construed to be limiting in any way. A number of final components may be formed by permuting all possible combinations of the constituent moieties with each other. When hydrocarbyl radicals including alkyl, alkenyl, alkynyl, cycloalkyl, cycloalkenyl, cycloalkynyl and aromatic radicals are disclosed in this application the term includes all isomers. For example, butyl includes n-butyl, 2-methylpropyl, 1-methylpropyl, tert-butyl, and cyclobutyl; pentyl includes n-pentyl, 1-methylbutyl, 2-methylbutyl, 3-methylbutyl, 1-ethylpropyl, neopentyl, cyclopentyl and methylcyclobutyl; butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl. This includes when a radical is bonded to another group, for example, propylcyclopentadienyl include n-propylcyclopentadienyl, isopropylcyclopentadienyl and cyclopropylcyclopentadienyl. In general, the ligands or groups illustrated in Table A include all isomeric forms. For example, dimethylcyclopentadienyl includes 1,2-dimethylcyclopentadienyl and 1,3-dimethylcyclopentadienyl; methylindenyl includes 1-methylindenyl, 2-methylindenyl, 3-methylindenyl, 4-methylindenyl, 5-methylindenyl, 6-methylindenyl and 7-methylindenyl; methylethylphenyl includes ortho-methylethylphenyl, meta-methylethylphenyl and para-methylethylphenyl. Examples of specific invention catalyst precursors take the following formula where some components are listed in Table A. To illustrate members of the transition metal component, select any combination of the species listed in Tables A. For nomenclature purposes, for the bridging group, A', the words "silyl" and "silylene" are used interchangeably, and represent a diradical species. For the bridging group A', "ethylene" refers to a 1,2-ethylene linkage and is distinguished from ethene-1,1-diyl. Thus, for the bridging group A', "ethylene" and "1,2-ethylene" are used interchangeably. For compounds having a bridging group, A', the bridge position on the cyclopentadienyl-type ring is always considered the 1-position. The numbering scheme previous defined for the indenyl ring is used to indicate the bridge position; if a number is not specified, it is assumed that the bridge to the indenyl ligand is in the one position.

TABLE A

A' dimethylsilylene
diethylsilylene
dipropylsilylene
dibutylsilylene
dipentylsilylene
dihexylsilylene
diheptylsilylene
dioctylsilylene
dinonylsilylene
didecylsilylene
diundecylsilylene
didodecylsilylene TABLE A-continued ditridecylsilylene
ditetradecylsilylene
dipentadecylsilylene
dihexadecylsilylene
diheptadecylsilylene
dioctadecylsilylene
dinonadecylsilylene
dieicosylsilylene
diheneicosylsilylene
didocosylsilylene
ditricosylsilylene
ditetracosylsilylene
dipentacosylsilylene
dihexacosylsilylene
diheptacosylsilylene
dioctacosylsilylene
dinonacosylsilylene
ditriacontylsilylene
dicyclohexylsilylene
dicyclopentylsilylene
dicycloheptylsilylene
dicyclooctylsilylene
dicyclodecylsilylene
dicyclododecylsilylene
dinapthylsilylene
diphenylsilylene
ditolylsilylene
dibenzylsilylene
diphenethylsilylene
di(butylphenethyl)silylene
methylethylsilylene
methylpropylsilylene
methylbutylsilylene
methylhexylsilylene
methylphenylsilylene
ethylphenylsilylene
ethylpropylsilylene
ethylbutylsilylene
propylphenylsilylene
dimethylgermylene
diethylgermylene
diphenylgermylene
methylphenylgermylene
cyclotetramethylenesilylene
cyclopentamethylenesilylene
cyclotrimethylenesilylene
cyclohexylazanediyl
butylazanediyl
methylazanediyl
phenylazanediyl
perfluorophenylazanediyl
methylphosphanediyl
ethylphosphanediyl
propylphosphanediyl
butylphosphanediyl
cyclohexylphosphanediyl
phenylphosphanediyl
methylboranediyl
phenylboranediyl
methylene
dimethylmethylene
diethylmethylene
dibutylmethylene
dipropylmethylene
diphenylmethylene
ditolylmethylene
di(butylphenyl)methylene
di(trimethylsilylphenyl)methylene
di(triethylsilylphenyl)methylene
dibenzylmethylene
cyclotetramethylenemethylene
cyclopentamethylenemethylene
ethylene
methylethylene
dimethylethylene
trimethylethylene
tetramethylethylene
cyclopentylene
cyclohexylene
cycloheptylene

TABLE A-continued cyclooctylene
propanediyl
methylpropanediyl
dimethylpropanediyl
trimethylpropanediyl
tetramethylpropanediyl
pentamethylpropanediyl
hexamethylpropanediyl
tetramethyldisiloxylene
vinylene
ethene-1,1-diyl
divinylsilylene
dipropenylsilylene
dibutenylsilylene
methylvinylsilylene
methylpropenylsilylene
methylbutenylsilylene
dimethylsilylmethylene
diphenylsilylmethylene
dimethylsilylethylene
diphenylsilylethylene
dimethylsilylpropylene
diphenylsilylpropylene
dimethylstannylene
diphenylstannylene $X_1$ or $X_2$ chloride
bromide
iodide
fluoride
hydride
methyl
ethyl
propyl
butyl
pentyl
hexyl
heptyl
octyl
nonyl
decyl
undecyl
dodecyl
tridecyl
tetradecyl
pentadecyl
hexadecyl
heptadecyl
octadecyl
nonadecyl
eicosyl
heneicosyl
docosyl
tricosyl
tetracosyl
pentacosyl
hexacosyl
heptacosyl
octacosyl
nonacosyl
triacontyl
phenyl
benzyl
phenethyl
tolyl
methoxy
ethoxy
propoxy
butoxy
dimethylamido
diethylamido
methylethylamido
phenoxy
benzoxy
allyl $X_1$ and $X_2$ together methylidene
ethylidene
propylidene
tetramethylene
pentamethylene
hexamethylene
ethylenedihydroxy
butadiene
methylbutadiene
dimethylbutadiene
pentadiene
methylpentadiene
dimethylpentadiene
hexadiene
methylhexadiene
dimethylhexadiene

M titanium
zirconium
hafnium

Cp, Cp* cyclopentadienyl
methylcyclopentadienyl
dimethylcyclopentadienyl
trimethylcyclopentadienyl
tetramethylcyclopentadienyl
ethylcyclopentadienyl
diethylcyclopentadienyl
propylcyclopentadienyl
dipropylcyclopentadienyl
butylcyclopentadienyl
dibutylcyclopentadienyl
pentylcyclopentadienyl
dipentylcyclopentadienyl
hexylcyclopentadienyl
dihexylcyclopentadienyl
heptylcyclopentadienyl
diheptylcyclopentadienyl
octylcyclopentadienyl
dioctylcyclopentadienyl
nonylcyclopentadienyl
dinonylcyclopentadienyl
decylcyclopentadienyl
didecylcyclopentadienyl
undecylcyclopentadienyl
dodecylcyclopentadienyl
tridecylcyclopentadienyl
tetradecylcyclopentadienyl
pentadecylcyclopentadienyl
hexadecylcyclopentadienyl
heptadecylcyclopentadienyl
octadecylcyclopentadienyl
nonadecylcyclopentadienyl
eicosylcyclopentadienyl
heneicosylcyclopentadienyl
docosylcyclopentadienyl
tricosylcyclopentadienyl
tetracosylcyclopentadienyl
pentacosylcyclopentadienyl
hexacosylcyclopentadienyl
heptacosylcyclopentadienyl
octacosylcyclopentadienyl
nonacosylcyclopentadienyl
triacontylcyclopentadienyl
cyclohexylcyclopentadienyl
phenylcyclopentadienyl
diphenylcyclopentadienyl
triphenylcyclopentadienyl
tetraphenylcyclopentadienyl
tolylcyclopentadineyl
benzylcyclopentadienyl
phenethylcyclopentadienyl
cyclohexylmethylcyclopentadienyl
napthylcyclopentadienyl
methylphenylcyclopentadienyl
methyltolylcyclopentadienyl
methylethylcyclopentadienyl
methylpropylcyclopentadienyl
methylbutylcyclopentadienyl
methylpentylcyclopentadienyl

TABLE A-continued methylhexylcyclopentadienyl
methylheptylcyclpentadienyl
methyloctylcyclopentadienyl
methylnonylcyclopentadienyl
methyldecylcyclopentadienyl
vinylcyclopentadienyl
propenylcyclopentadienyl
butenylcyclopentadienyl
indenyl
methylindenyl
dimethylindenyl
trimethylindenyl
tetramethylindenyl
pentamethylindenyl
methylpropylindenyl
dimethylpropylindenyl
methyldipropylindenyl
methylethylindenyl
methylbutylindenyl
ethylindenyl
propylindenyl
butylindenyl
pentylindenyl
hexylindenyl
heptylindenyl
octylindenyl
nonylindenyl
decylindenyl
phenylindenyl
(fluorophenyl)indenyl
(methylphenyl)indenyl
biphenylindenyl
(bis(trifluoromethyl)phenyl)indenyl
napthylindenyl
phenanthrylindenyl
benzylindenyl
benzindenyl
cyclohexylindenyl
methylphenylindenyl
ethylphenylindenyl
propylphenylindenyl
methylnapthylindenyl
ethylnapthylindenyl
propylnapthylindenyl
(methylphenyl)indenyl
(dimethylphenyl)indenyl
(ethylphenyl)indenyl
(diethylphenyl)indenyl
(propylphenyl)indenyl
(dipropylphenyl)indenyl
methyltetrahydroindenyl
ethyltetrahydroindenyl
propyltetrahydroindenyl
butyltetrahydroindenyl
phenyltetrahydroindenyl
(diphenylmethyl)cyclopentadienyl
trimethylsilylcyclopentadienyl
triethylsilylcyclopentadienyl
trimethylgermylcyclopentadienyl
trifluromethylcyclopentadienyl
cyclopenta[b]thienyl
cyclopenta[b]furanyl
cyclopenta[b]selenophenyl
cyclopenta[b]tellurophenyl
cyclopenta[b]pyrrolyl
cyclopenta[b]phospholyl
cyclopenta[b]arsolyl
cyclopenta[b]stibolyl
methylcyclopenta[b]thienyl
methylcyclopenta[b]furanyl
methylcyclopenta[b]selenophenyl
methylcyclopenta[b]tellurophenyl
methylcyclopenta[b]pyrrolyl
methylcyclopenta[b]phospholyl
methylcyclopenta[b]arsolyl
methylcyclopenta[b]stibolyl
dimethylcyclopenta[b]thienyl
dimethylcyclopenta[b]furanyl
dimethylcyclopenta[b]pyrrolyl
dimethylcyclopenta[b]phospholyl
trimethylcyclopenta[b]thienyl
trimethylcyclopenta[b]furanyl
trimethylcyclopenta[b]pyrrolyl
trimethylcyclopenta[b]phospholyl
ethylcyclopenta[b]thienyl
ethylcyclopenta[b]furanyl
ethylcyclopenta[b]pyrrolyl
ethylcyclopenta[b]phospholyl
diethylcyclopenta[b]thienyl
diethylcyclopenta[b]furanyl
diethylcyclopenta[b]pyrrolyl
diethylcyclopenta[b]phospholyl
triethylcyclopenta[b]thienyl
triethylcyclopenta[b]furanyl
triethylcyclopenta[b]pyrrolyl
triethylcyclopenta[b]phospholyl
propylcyclopenta[b]thienyl
propylcyclopenta[b]furanyl
propylcyclopenta[b]pyrrolyl
propylcyclopenta[b]phospholyl
dipropylcyclopenta[b]thienyl
dipropylcyclopenta[b]furanyl
dipropylcyclopenta[b]pyrrolyl
dipropylcyclopenta[b]phospholyl
tripropylcyclopenta[b]thienyl
tripropylcyclopenta[b]furanyl
tripropylcyclopenta[b]pyrrolyl
tripropylcyclopenta[b]phospholyl
butylcyclopenta[b]thienyl
butylcyclopenta[b]furanyl
butylcyclopenta[b]pyrrolyl
butylcyclopenta[b]phospholyl
dibutylcyclopenta[b]thienyl
dibutylcyclopenta[b]furanyl
dibutylcyclopenta[b]pyrrolyl
dibutylcyclopenta[b]phospholyl
tributylcyclopenta[b]thienyl
tributylcyclopenta[b]furanyl
tributylcyclopenta[b]pyrrolyl
tributylcyclopenta[b]phospholyl
ethylmethylcyclopenta[b]thienyl
ethylmethylcyclopenta[b]furanyl
ethylmethylcyclopenta[b]pyrrolyl
ethylmethylcyclopenta[b]phospholyl
methylpropylcyclopenta[b]thienyl
methylpropylcyclopenta[b]furanyl
methylpropylcyclopenta[b]pyrrolyl
methylpropylcyclopenta[b]phospholyl
butylmethylcyclopenta[b]thienyl
butylmethylcyclopenta[b]furanyl
butylmethylcyclopenta[b]pyrrolyl
butylmethylcyclopenta[b]phospholyl
cyclopenta[c]thienyl
cyclopenta[c]furanyl
cyclopenta[c]selenophenyl
cyclopenta[c]tellurophenyl
cyclopenta[c]pyrrolyl
cyclopenta[c]phospholyl
cyclopenta[c]arsolyl
cyclopenta[c]stibolyl
methylcyclopenta[c]thienyl
methylcyclopenta[c]furanyl
methylcyclopenta[c]selenophenyl
methylcyclopenta[c]tellurophenyl
methylcyclopenta[c]pyrrolyl
methylcyclopenta[c]phospholyl
methylcyclopenta[c]arsolyl
methylcyclopenta[c]stibolyl
dimethylcyclopenta[c]thienyl
dimethylcyclopenta[c]furanyl
dimethylcyclopenta[c]pyrrolyl
dimethylcyclopenta[c]phospholyl
trimethylcyclopenta[c]thienyl
trimethylcyclopenta[c]furanyl
trimethylcyclopenta[c]pyrrolyl
trimethylcyclopenta[c]phospholyl
ethylcyclopenta[c]thienyl
ethylcyclopenta[c]furanyl
ethylcyclopenta[c]pyrrolyl
ethylcyclopenta[c]phospholyl

TABLE A-continued diethylcyclopenta[c]thienyl
diethylcyclopenta[c]furanyl
diethylcyclopenta[c]pyrrolyl
diethylcyclopenta[c]phospholyl
triethylcyclopenta[c]thienyl
triethylcyclopenta[c]furanyl
triethylcyclopenta[c]pyrrolyl
triethylcyclopenta[c]phospholyl
propylcyclopenta[c]thienyl
propylcyclopenta[c]furanyl
propylcyclopenta[c]pyrrolyl
propylcyclopenta[c]phospholyl
dipropylcyclopenta[c]thienyl
dipropylcyclopenta[c]furanyl
dipropylcyclopenta[c]pyrrolyl
dipropylcyclopenta[c]phospholyl
tripropylcyclopenta[c]thienyl
tripropylcyclopenta[c]furanyl
tripropylcyclopenta[c]pyrrolyl
tripropylcyclopenta[c]phospholyl
butylcyclopenta[c]thienyl
butylcyclopenta[c]furanyl
butylcyclopenta[c]pyrrolyl
butylcyclopenta[c]phospholyl
dibutylcyclopenta[c]thienyl
dibutylcyclopenta[c]furanyl
dibutylcyclopenta[c]pyrrolyl
dibutylcyclopenta[c]phospholyl
tributylcyclopenta[c]thienyl
tributylcyclopenta[c]furanyl
tributylcyclopenta[c]pyrrolyl
tributylcyclopenta[c]phospholyl
ethylmethylcyclopenta[c]thienyl
ethylmethylcyclopenta[c]furanyl
ethylmethylcyclopenta[c]pyrrolyl
ethylmethylcyclopenta[c]phospholyl
methylpropylcyclopenta[c]thienyl
methylpropylcyclopenta[c]furanyl
methylpropylcyclopenta[c]pyrrolyl
methylpropylcyclopenta[c]phospholyl
butylmethylcyclopenta[c]thienyl
butylmethylcyclopenta[c]furanyl
butylmethylcyclopenta[c]pyrrolyl
butylmethylcyclopenta[c]phospholyl
pentamethylcyclopentadienyl
tetrahydroindenyl
mehtyltetrahydroindenyl
dimethyltetrahydroindenyl In a preferred embodiment of the invention, Cp is the same as Cp* and is a substituted or unsubstituted indenyl or tetrahydroindenyl ligand. Most preferred substituted indenyl or tetrahydroindenyl ligands do not have a substituent in the 2-position of the indenyl or tetrahydroindenyl ring. Most preferred substituted and unsubstituted indenyl or tetrahydroindenyl ligands include indenyl, tetrahydroindenyl, 4,7-dimethylindenyl and 5,6-dimethylindenyl.

In another embodiment, the metallocene catalyst compound used herein is not rac-$CH_2CH_2(Ind)_2ZrCl_2$ and or rac-$Me_2Si(2\text{-Me-Ind})_2ZrCl_2$. In another embodiment, the metallocene catalyst compound used herein is not rac-$CH_2CH_2(Ind)_2ZrCl_2$ and or rac-$Me_2Si(2\text{-Me-Ind})_2ZrCl_2$ and the activator is not methylalumoxane, where Me is methyl and Ind is indenyl.

In a preferred embodiment of the invention, when the metallocene is used with an alumoxane, Cp is the same as Cp* and is a substituted or unsubstituted indenyl or tetrahydroindenyl ligand. Most preferred substituted indenyl or tetrahydroindenyl ligands do not have a substituent in the 2-position of the indenyl or tetrahydroindenyl ring. Most preferred substituted and unsubstituted indenyl or tetrahydroindenyl ligands include indenyl, tetrahydroindenyl, 4,7-dimethylindenyl and 5,6-dimethylindenyl.

In another embodiment, when the metallocene is used with an alumoxane, then the metallocene catalyst compound used herein is not rac-$CH_2CH_2(Ind)_2ZrCl_2$ and or rac-$Me_2Si(2\text{-Me-Ind})_2ZrCl_2$. In another embodiment, the metallocene catalyst compound used herein is not rac-$CH_2CH_2(Ind)_2ZrCl_2$ and or rac-$Me_2Si(2\text{-Me-Ind})_2ZrCl_2$ and the activator is not methylalumoxane, where Me is methyl and Ind is indenyl.

In a preferred embodiment of the invention, when used with an NCA, Cp is the same as Cp* and is a substituted or unsubstituted indenyl or tetrahydroindenyl ligand. Most preferred substituted and unsubstituted indenyl or tetrahydroindenyl ligands include having a substituent in the 2-position of the indenyl or tetrahydroindenyl ring, indenyl, tetrahydroindenyl, 4,7-dimethylindenyl and 5,6-dimethylindenyl.

In another embodiment, when used with NCA, the metallocene catalyst compound used herein is bridged, substituted or unsubstituted metallocenes of general structure as shown in formula (1) or (2)

In another embodiment, the catalyst used herein is $Y_2$methylidene$(R_nCp)(R_mFlu)ZrX_2$ or $Y_2$silyl$(R_nCp)(R_m\text{-}Flu)ZrX_2$ where Y is independently a C1 to C20 alkyl or a substituted or unsubstituted phenyl group, X is a halogen, a substituted or unsubstituted phenyl group, or a C1 to C20 alkyl, Cp is a cyclopentadienyl ring, R is a C1 to C20 alkyl group, n is a number denoting the degree of substitution of Cp and is a number from 0 to 5, Flu is a fluorenyl ring, m is a number denoting the degree of substitution of Flu and is a number from 0 to 9.

Preferred metallocene compounds (pre-catalysts) which, according to the present invention, provide catalyst systems which are specific to the production of poly-α-olefins having mm triads over 40% include the racemic versions of: dimethylsilylbis(indenyl)zirconium dichloride, dimethylsilylbis(indenyl)zirconium dimethyl, diphenylsilylbis(indenyl)zirconium dichloride, diphenylsilylbis(indenyl)zirconium dimethyl, methylphenylsilylbis(indenyl)zirconium dichloride, methylphenylsilylbis(indenyl)zirconium dimethyl, ethylenebis(indenyl)zirconium dichloride, ethylenebis(indenyl)zirconium dimethyl, methylenebis(indenyl)zirconium dichloride, methylenebis(indenyl)zirconium dimethyl, dimethylsilylbis(indenyl)hafnium dichloride, dimethylsilylbis(indenyl)hafnium dimethyl, diphenylsilylbis(indenyl)hafnium dichloride, diphenylsilylbis(indenyl)hafnium dimethyl, methylphenylsilylbis(indenyl)hafnium dichloride, methylphenylsilylbis(indenyl)hafnium dimethyl, ethylenebis(indenyl)hafnium dichloride, ethylenebis(indenyl)hafnium dimethyl, methylenebis(indenyl)hafnium dichloride, methylenebis(indenyl)hafnium dimethyl, dimethylsilylbis(tetrahydroindenyl)zirconium dichloride, dimethylsilylbis(tetrahydroindenyl)zirconium dimethyl, diphenylsilylbis(tetrahydroindenyl)zirconium dichloride, diphenylsilylbis(tetrahydroindenyl)zirconium dimethyl, methylphenylsilylbis(tetrahydroindenyl)zirconium dichloride, methylphenylsilylbis(tetrahydroindenyl)zirconium dimethyl, ethylenebis(tetrahydroindenyl)zirconium dichloride, ethylenebis(tetrahydroindenyl)zirconium dimethyl, methylenebis(tetrahydroindenyl)zirconium dichloride, methylenebis(tetrahydroindenyl)zirconium dimethyl, dimethylsilylbis(tetrahydroindenyl)hafnium dichloride, dimethylsilylbis(tetrahydroindenyl)hafnium dimethyl, diphenylsilylbis(tetrahydroindenyl)hafnium dichloride, diphenylsilylbis(tetrahydroindenyl)hafnium dimethyl, methylphenylsilylbis(tetrahydroindenyl)hafnium dichloride, methylphenylsilylbis(tetrahydroindenyl)hafnium dimethyl, ethylenebis(tetrahydroindenyl)hafnium dichloride, ethylenebis(tetrahydroindenyl)hafnium dimethyl, methylenebis(tetrahydroindenyl)hafnium dichloride, methylenebis(tetrahydroindenyl)hafnium dimethyl, dimethylsilylbis(4,7-dimethylindenyl)zirconium dichloride, dimethylsilylbis(4,7- dimethylindenyl)zirconium dimethyl, diphenylsilylbis(4,7-dimethylindenyl)zirconium dichloride, diphenylsilylbis(4,7-dimethylindenyl)zirconium dimethyl, methylphenylsilylbis(4,7-dimethylindenyl)zirconium dichloride, methylphenylsilylbis(4,7-dimethylindenyl)zirconium dimethyl, ethylenebis(4,7-dimethylindenyl)zirconium dichloride, ethylenebis(4,7-dimethylindenyl)zirconium dimethyl, methylenebis(4,7-dimethylindenyl)zirconium dichloride, methylenebis(4,7-dimethylindenyl)zirconium dimethyl, dimethylsilylbis(4,7-dimethylindenyl)hafnium dichloride, dimethylsilylbis(4,7-dimethylindenyl)hafnium dimethyl, diphenylsilylbis(4,7-dimethylindenyl)hafnium dichloride, diphenylsilylbis(4,7-dimethylindenyl)hafnium dimethyl, methylphenylsilylbis(4,7-dimethylindenyl)hafnium dichloride, methylphenylsilylbis(4,7-dimethylindenyl)hafnium dimethyl, ethylenebis(4,7-dimethylindenyl)hafnium dichloride, ethylenebis(4,7-dimethylindenyl)hafnium dimethyl, methylenebis(4,7-dimethylindenyl)hafnium dichloride, methylenebis(4,7-dimethylindenyl)hafnium dimethyl, dimethylsilylbis(2-methyl-4-napthylindenyl)zirconium dichloride, dimethylsilylbis(2-methyl-4-napthylindenyl)zirconium dimethyl, diphenylsilylbis(2-methyl-4-napthylindenyl)zirconium dichloride, dimethylsilylbis(2,3-dimethylcyclopentadienyl)zirconium dichloride, dimethylsilylbis(2,3-dimethylcyclopentadienyl)zirconium dimethyl, diphenylsilylbis(2,3-dimethylcyclopentadienyl)zirconium dichloride, diphenylsilylbis(2,3-dimethylcyclopentadienyl)zirconium dimethyl, methylphenylsilylbis(2,3-dimethylcyclopentadienyl)zirconium dichloride, methylphenylsilylbis(2,3-dimethylcyclopentadienyl)zirconium dimethyl, ethylenebis(2,3-dimethylcyclopentadienyl)zirconium dichloride, ethylenebis(2,3-dimethylcyclopentadienyl)zirconium dimethyl, methylenebis(2,3-dimethylcyclopentadienyl)zirconium dichloride, methylenebis(2,3-dimethylcyclopentadienyl)zirconium dimethyl, dimethylsilylbis(2,3-dimethylcyclopentadienyl)hafnium dichloride, dimethylsilylbis(2,3-dimethylcyclopentadienyl)hafnium dimethyl, diphenylsilylbis(2,3-dimethylcyclopentadienyl)hafnium dichloride, diphenylsilylbis(2,3-dimethylcyclopentadienyl)hafnium dimethyl, methylphenylsilylbis(2,3-dimethylcyclopentadienyl)hafnium dichloride, methylphenylsilylbis(2,3-dimethylcyclopentadienyl)hafnium dimethyl, ethylenebis(2,3-dimethylcyclopentadienyl)hafnium dichloride, ethylenebis(2,3-dimethylcyclopentadienyl)hafnium dimethyl, methylenebis(2,3-dimethylcyclopentadienyl)hafnium dichloride, methylenebis(2,3-dimethylcyclopentadienyl)hafnium dimethyl, dimethylsilylbis(3-trimethylsilylcyclopentadienyl)zirconium dichloride, dimethylsilylbis(3-trimethylsilylcyclopentadienyl)zirconium dimethyl, diphenylsilylbis(3-trimethylsilylcyclopentadienyl)zirconium dichloride, diphenylsilylbis(3-trimethylsilylcyclopentadienyl)zirconium dimethyl, methylphenylsilylbis(3-trimethylsilylcyclopentadienyl)zirconium dichloride, methylphenylsilylbis(3-trimethylsilylcyclopentadienyl)zirconium dimethyl, ethylenebis(3-trimethylsilylcyclopentadienyl)zirconium dichloride, ethylenebis(3-trimethylsilylcyclopentadienyl)zirconium dimethyl, methylenebis(3-trimethylsilylcyclopentadienyl)zirconium dichloride, methylenebis(3-trimethylsilylcyclopentadienyl)zirconium dimethyl, dimethylsilylbis(3-trimethylsilylcyclopentadienyl)hafnium dichloride, dimethylsilylbis(3-trimethylsilylcyclopentadienyl)hafnium dimethyl, diphenylsilylbis(3-trimethylsilylcyclopentadienyl)hafnium dichloride, diphenylsilylbis(3-trimethylsilylcyclopentadienyl)hafnium dimethyl, methylphenylsilylbis(3-trimethylsilylcyclopentadienyl)hafnium dichloride, methylphenylsilylbis(3-trimethylsilylcyclopentadienyl)hafnium dimethyl, ethylenebis(3-trimethylsilylcyclopentadienyl)hafnium dichloride, ethylenebis(3-trimethylsilylcyclopentadienyl)hafnium dimethyl, methylenebis(3-trimethylsilylcyclopentadienyl)hafnium dichloride, methylenebis(3-trimethylsilylcyclopentadienyl)hafnium dimethyl, Particularly preferred species are the racemic versions of: dimethylsilylbis(indenyl)zirconium dichloride, dimethylsilylbis(indenyl)zirconium dimethyl, ethylenebis(indenyl)zirconium dichloride, ethylenebis(indenyl)zirconium dimethyl, dimethylsilylbis(tetrahydroindenyl)zirconium dichloride, dimethylsilylbis(tetrahydroindenyl)zirconium dimethyl, ethylenebis(tetrahydroindenyl)zirconium dichloride, ethylenebis(tetrahydroindenyl)zirconium dimethyl, dimethylsilylbis(4,7-dimethylindenyl)zirconium dichloride, dimethylsilylbis(4,7-dimethylindenyl)zirconium dimethyl, ethylenebis(4,7-dimethylindenyl)zirconium dichloride, ethylenebis(4,7-dimethylindenyl)zirconium dimethyl, dimethylsilylbis(indenyl)hafnium dichloride, dimethylsilylbis(indenyl)hafnium dimethyl, ethylenebis(indenyl)hafnium dichloride, ethylenebis(indenyl)hafnium dimethyl, dimethylsilylbis(tetrahydroindenyl)hafnium dichloride, dimethylsilylbis(tetrahydroindenyl)hafnium dimethyl, ethylenebis(tetrahydroindenyl)hafnium dichloride, ethylenebis(tetrahydroindenyl)hafnium dimethyl, dimethylsilylbis(4,7-dimethylindenyl)hafnium dichloride, dimethylsilylbis(4,7-dimethylindenyl)hafnium dimethyl, ethylenebis(4,7-dimethylindenyl)hafnium dichloride, and ethylenebis(4,7-dimethylindenyl)hafnium dimethyl.

Preferred catalyst compounds also include bis(1,3-dimethylcyclopentadienyl)zirconium dichloride and bis(tetramethylcyclopentadienyl)zirconium dichloride Activators and Catalyst Activation The catalyst precursors, when activated by a commonly known activator such as methylalumoxane, form active catalysts for the polymerization or oligomerization of olefins. Activators that may be used include alumoxanes such as methylalumoxane, modified methylalumoxane, ethylalumoxane, iso-butylalumoxane and the like; Lewis acid activators include triphenylboron, tris-perfluorophenylboron, tris-perfluorophenylaluminum and the like; ionic activators include dimethylanilinium tetrakisperfluorophenylborate, triphenylcarboniumtetrakis perfluorophenylborate, dimethylaniliniumtetrakisperfluorophenylaluminate, and the like.

A co-activator is a compound capable of alkylating the transition metal complex, such that when used in combination with an activator, an active catalyst is formed. Co-activators include alumoxanes such as methylalumoxane, modified alumoxanes such as modified methylalumoxane, and aluminum alkyls such trimethylaluminum, tri-isobutylaluminum, tri-ethylaluminum, and tri-isopropylaluminum, tri-n-hexylaluminum, tri-n-octylaluminum, tri-n-decylaluminum or tri-n-dodecylaluminum. Co-activators are typically used in combination with Lewis acid activators and ionic activators when the pre-catalyst is not a dihydrocarbyl or dihydride complex. Sometimes co-activators are also used as scavengers to deactivate impurities in feed or reactors.

Particularly preferred co-activators include alkylaluminum compound is represented by the formula: $R_3Al$, where each R is, independently, a C1 to C18 alkyl group, preferably each R is, independently, selected from the group consisting of methyl, ethyle, n-propyl, iso-propyl, iso-butyl, n-butyl, t-butyl, n-pentyl, iso-pentyl, neopentyl, n-hexyl, iso-hexyl, n-heptyl, iso-heptyl, n-octyl, iso-octyl, n-nonyl, n-decyl, n-undecyl, n-dodecyl, n-tridecyl, n-tetradecyl, n-pentadecy, n-hexadecyl, n-heptadecyl, n-octadecyl, and their iso-analogs.

The alumoxane component useful as an activator typically is preferably an oligomeric aluminum compound represented by the general formula $(R^x—Al—O)_n$, which is a cyclic compound, or $R^x(R^x—Al—O)_nAlR^x_2$, which is a linear compound. It is believed that the most common alumoxanes are a mixture of the cyclic and linear compounds. In the general alumoxane formula, $R^x$ is independently a $C_1$-$C_{20}$ alkyl radical, for example, methyl, ethyl, propyl, butyl, pentyl, isomers thereof, and the like, and "n" is an integer from 1-50. Most preferably, $R^x$ is methyl and "n" is at least 4. Methylalumoxane and modified methylalumoxanes are most preferred. For further descriptions see, EP 0 279 586, EP 0 594 218, EP 0 561 476, WO94/10180 and U.S. Pat. Nos. 4,665,208, 4,874,734, 4,908,463, 4,924,018, 4,952,540, 4,968,827, 5,041,584, 5,091,352, 5,103,031, 5,157,137, 5,204,419, 5,206,199, 5,235,081, 5,248,801, 5,329,032, 5,391,793, and 5,416,229.

When an alumoxane or modified alumoxane is used, the catalyst-precursor-to-activator molar ratio is from about 1:3000 to 10:1; alternatively, 1:2000 to 10:1; alternatively 1:1000 to 10:1; alternatively, 1:500 to 1:1; alternatively 1:300 to 1:1; alternatively 1:250 to 1:1, alternatively 1:200 to 1:1; alternatively 1:100 to 1:1; alternatively 1:50 to 1:1; alternatively 1:10 to 1:1. When the activator is an alumoxane (modified or unmodified), some embodiments select the maximum amount of activator at a 5000-fold molar excess over the catalyst precursor (per metal catalytic site). The preferred minimum activator-to-catalyst-precursor ratio is 1:1 molar ratio.

Ionic activators (at times used in combination with a co-activator) may be used in the practice of this invention. Preferably, discrete ionic activators such as [Me$_2$PhNH][B(C$_6$F$_5$)$_4$], [Ph$_3$C][B(C$_6$F$_5$)$_4$], [Me$_2$PhNH] [B((C$_6$H$_3$-3,5-(CF$_3$)$_2$))$_4$], [Ph$_3$C][B((C$_6$H$_3$-3,5-(CF$_3$)$_2$))$_4$], [NH$_4$][B(C$_6$H$_5$)$_4$] or Lewis acidic activators such as B(C$_6$F$_5$)$_3$ or B(C$_6$H$_5$)$_3$ can be used, where Ph is phenyl and Me is methyl. Preferred co-activators, when used, are alumoxanes such as methylalumoxane, modified alumoxanes such as modified methylalumoxane, and aluminum alkyls such as tri-isobutylaluminum, and trimethylaluminum, triethylaluminum, and tri-isopropylaluminum, tri-n-hexylaluminum, tri-n-octylaluminum, tri-n-decylaluminum or tri-n-dodecylaluminum.

It is within the scope of this invention to use an ionizing or stoichiometric activator, neutral or ionic, such as tri(n-butyl) ammoniumtetrakis(pentafluorophenyl)borate, a trisperfluorophenyl boron metalloid precursor or a trisperfluoronaphthyl boron metalloid precursor, polyhalogenated heteroborane anions (WO 98/43983), boric acid (U.S. Pat. No. 5,942,459) or combination thereof.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl or mixtures thereof. Even more preferably, the three groups are halogenated, preferably fluorinated, aryl groups. Most preferably, the neutral stoichiometric activator is trisperfluorophenyl boron or trisperfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Ionic catalysts can be prepared by reacting a transition metal compound with an activator, such as B(C$_6$F$_6$)$_3$, which upon reaction with the hydrolyzable ligand (X') of the transition metal compound forms an anion, such as ([B(C$_6$F$_5$)$_3$(X')]$^-$), which stabilizes the cationic transition metal species generated by the reaction. The catalysts can be, and preferably are, prepared with activator components which are ionic compounds or compositions. However preparation of activators utilizing neutral compounds is also contemplated by this invention.

Compounds useful as an activator component in the preparation of the ionic catalyst systems used in the process of this invention comprise a cation, which is preferably a Bronsted acid capable of donating a proton, and a compatible non-coordinating anion which anion is relatively large (bulky), capable of stabilizing the active catalyst species which is formed when the two compounds are combined and said anion will be sufficiently labile to be displaced by olefinic diolefinic and acetylenically unsaturated substrates or other neutral Lewis bases such as ethers, nitriles and the like. Two classes of compatible non-coordinating anions have been disclosed in EPA 277,003 and EPA 277,004 published 1988: 1) anionic coordination complexes comprising a plurality of lipophilic radicals covalently coordinated to and shielding a central charge-bearing metal or metalloid core, and 2) anions comprising a plurality of boron atoms such as carboranes, metallacarboranes and boranes. In a preferred embodiment, the stoichiometric activators include a cation and an anion component, and may be represented by the following formula: $(L^{}\text{-H})_d^+(A^{d-})$ wherein $L^{}$ is an neutral Lewis base; H is hydrogen; $(L^{**}\text{-H})^+$ is a Bronsted acid $A^{d-}$ is a non-coordinating anion having the charge d-d is an integer from 1 to 3.

The cation component, $(L^{**}\text{-H})_d^+$ may include Bronsted acids such as protons or protonated Lewis bases or reducible Lewis acids capable of protonating or abstracting a moiety, such as an alkyl or aryl, from the precatalyst after alkylation.

The activating cation $(L^{}\text{-H})_d^+$ may be a Bronsted acid, capable of donating a proton to the alkylated transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether, diethyl ether, tetrahydrofuran and dioxane, sulfoniums from thioethers, such as diethyl thioethers and tetrahydrothiophene, and mixtures thereof. The activating cation $(L^{}\text{-H})_d^+$ may also be a moiety such as silver, tropylium, carbeniums, ferroceniums and mixtures, preferably carboniums and ferroceniums; most preferably triphenyl carbonium. The anion component $A^{d-}$ include those having the formula $[M^{k+}Q_n]^{d-}$ wherein k is an integer from 1 to 3; n is an integer from 2-6; n-k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide. Preferably, each Q is a fluorinated hydrocarbyl group having, 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting examples of boron compounds which may be used as an activating cocatalyst in combination with a co-activator in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(tert-butyl) ammonium tetraphenylborate, N,N-dimethylanilinium tetraphenylborate, N,N-diethylanilinium tetraphenylborate, N,N-dimethyl-(2,4,6-trimethylanilinium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis (pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl (tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl) borate, trimethylammonium tetrakis(perfluoronaphthyl) borate, triethylammonium tetrakis(perfluoronaphthyl) borate, tripropylammonium tetrakis(perfluoronaphthyl) borate, tri(n-butyl)ammonium tetrakis(perfluoronaphthyl) borate, tri(tert-butyl)ammonium tetrakis(perfluoronaphthyl) borate, N,N-dimethylanilinium tetrakis(perfluoronaphthyl) borate, N,N-diethylanilinium tetrakis(perfluoronaphthyl) borate, N,N-dimethyl-(2,4,6-trimethylanilinium)tetrakis (perfluoronaphthyl)borate, trimethylammonium tetrakis (perfluorobiphenyl)borate, triethylammonium tetrakis (perfluorobiphenyl)borate, tripropylammonium tetrakis (perfluorobiphenyl)borate, tri(n-butyl)ammonium tetrakis (perfluorobiphenyl)borate, tri(tert-butyl)ammonium tetrakis (perfluorobiphenyl)borate, N,N-dimethylanilinium tetrakis (perfluorobiphenyl)borate, N,N-diethylanilinium tetrakis (perfluorobiphenyl)borate, N,N-dimethyl-(2,4,6-trimethylanilinium)tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis (trifluoromethyl)phenyl)borate, tri(n-butyl)ammonium tetrakis(3,5-bis(trifluoromethyl)phenyl)borate, tri(tert-butyl) ammonium tetrakis(3,5-bis(trifluoromethyl)phenyl)borate, N,N-dimethylanilinium tetrakis(3,5-bis(trifluoromethyl) phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl)phenyl)borate, and dialkyl ammonium salts such as: di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis (pentafluorophenyl)borate, triethylsilylium tetrakis (pentafluorophenyl)borate, benzene(diazonium)tetrakis (pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis (perfluoronaphthyl)borate, triphenylcarbenium tetrakis (perfluoronaphthyl)borate, triphenylphosphonium tetrakis (perfluoronaphthyl)borate, triethylsilylium tetrakis (perfluoronaphthyl)borate, benzene(diazonium)tetrakis (perfluoronaphthyl)borate, tropillium tetrakis (perfluorobiphenyl)borate, triphenylcarbenium tetrakis (perfluorobiphenyl)borate, triphenylphosphonium tetrakis (perfluorobiphenyl)borate, triethylsilylium tetrakis (perfluorobiphenyl)borate, benzene(diazonium)tetrakis (perfluorobiphenyl)borate, tropillium tetrakis(3,5-bis (trifluoromethyl)phenyl)borate, triphenylcarbenium tetrakis (3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl) phenyl)borate, and benzene(diazonium)tetrakis(3,5-bis(trifluoromethyl)phenyl)borate.

Most preferably, the ionic stoichiometric activator ($L^{**}$-H)$_d^+$($A^{d-}$) is N,N-dimethylanilinium tetrakis(perfluorophenyl)borate, N,N-dimethylanilinium tetrakis(perfluoronaphthyl)borate, N,N-dimethylanilinium tetrakis (perfluorobiphenyl)borate, N,N-dimethylanilinium tetrakis (3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis (3,5-bis(trifluoromethyl)phenyl)borate, or triphenylcarbenium tetra(perfluorophenyl)borate.

The catalyst precursors can also be activated with cocatalysts or activators that comprise non-coordinating anions containing metalloid-free cyclopentadienide ions. These are described in U.S. Patent Publication 2002/0058765 A1, published on 16 May 2002, and for the instant invention, require the addition of a co-activator to the catalyst pre-cursor. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Preferred non-coordinating anions useful in accordance with this invention are those that are compatible, stabilize the transition metal complex cation in the sense of balancing its ionic charge at +1, yet retain sufficient lability to permit displacement by an ethylenically or acetylenically unsaturated monomer during polymerization. These types of cocatalysts are sometimes used with scavengers such as but not limited to tri-iso-butylaluminum, tri-n-octylaluminum, tri-n-hexylaluminum, triethylaluminum or trimethylaluminum.

Invention processes also can employ cocatalyst compounds or activator compounds that are initially neutral Lewis acids but form a cationic metal complex and a noncoordinating anion, or a zwitterionic complex upon reaction with the alkylated transition metal compounds. The alkylated metallocene compound is formed from the reaction of the catalyst pre-cursor and the co-activator. For example, tris(pentafluorophenyl)boron or aluminum act to abstract a hydrocarbyl ligand to yield an invention cationic transition metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of zwitterionic complexes using analogous Group 4 compounds, see U.S. Pat. Nos. 5,624,878; 5,486,632; and 5,527,929.

Additional neutral Lewis-acids are known in the art and are suitable for abstracting formal anionic ligands. See in particular the review article by E. Y.-X. Chen and T. J. Marks, "Cocatalysts for Metal-Catalyzed Olefin Polymerization: Activators, Activation Processes, and Structure-Activity Relationships", Chem. Rev., 100, 1391-1434 (2000).

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the catalyst-precursor-to-activator molar ratio may be any ratio. Combinations of the described activator compounds may also be used for activation.

When an ionic or neutral stoichiometric activator (such as an NCA) is used, the catalyst-precursor-to-activator molar ratio is from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; 1:1 to 1:1.2. The catalyst-precursor-to-co-activator molar ratio is from 1:500 to 1:1, 1:100 to 100:1; 1:75 to 75:1; 1:50 to 50:1; 1:25 to 25:1; 1:15 to 15:1; 1:10 to 10:1; 1:5 to 5:1, 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1. Preferred activators and activator/co-activator combinations include methylalumoxane, modified methylalumoxane, mixtures of methylalumoxane with dimethylanilinium tetrakis(pentafluorophenyl)borate or tris(pentafluorophenyl)boron, and mixtures of trimethyl aluminum with dimethylanilinium tetrakis(pentafluorophenyl)borate or tris(pentafluorophenyl)boron. In some embodiments, scavenging compounds are used with stoichiometric activators. Typical aluminum or boron alkyl components useful as scavengers are represented by the general formula $R^xJZ_2$ where J is aluminum or boron, Rx is as previously defined above, and each Z is independently Rx or a different univalent anionic ligand such as halogen (Cl, Br, I), alkoxide ($OR^x$) and the like. Most preferred aluminum alkyls include triethylaluminum, diethylaluminum chloride, tri-iso-butylaluminum, tri-n-octylaluminum. tri-n-hexylaluminum, trimethylaluminum and the like. Preferred boron alkyls include triethylboron. Scavenging compounds may also be alumoxanes and modified alumoxanes including methylalumoxane and modified methylalumoxane.

Supported Catalysts

Supported catalysts and or supported catalyst systems may be used to prepare PAO's. To prepare uniform supported catalysts, the catalyst precursor preferably dissolves in the chosen solvent. The term "uniform supported catalyst" means that the catalyst precursor, the activator, and or the activated catalyst approach uniform distribution upon the support's accessible surface area, including the interior pore surfaces of porous supports. Some embodiments of supported catalysts prefer uniform supported catalysts; other embodiments show no such preference.

Useful supported catalyst systems may be prepared by any method effective to support other coordination catalyst systems, effective meaning that the catalyst so prepared can be used for oligomerizing or polymerizing olefins in a heterogenous process. The catalyst precursor, activator, co-activator (if needed), suitable solvent, and support may be added in any order or simultaneously.

By one method, the activator, dissolved in an appropriate solvent such as toluene, may be stirred with the support material for 1 minute to 10 hours to prepare the supported catalyst. The total solution volume (of the catalyst solution, the activator solution or both) may be greater than the pore volume of the support, but some embodiments limit the total solution volume below that needed to form a gel or slurry (about 90% to 400%, preferably about 100-200%, of the pore volume). The mixture is optionally heated from 30-200° C. during this time. The catalyst precursor may be added to this mixture as a solid, if a suitable solvent is employed in the previous step, or as a solution. Alternatively, the mixture can be filtered, and the resulting solid mixed with a catalyst precursor solution. Similarly, the mixture may be vacuum dried and mixed with a catalyst precursor solution. The resulting catalyst mixture is then stirred for 1 minute to 10 hours, and the supported catalyst is either filtered from the solution and vacuum dried or subjected to evaporation to remove the solvent.

Alternatively, the catalyst precursor and activator may be combined in solvent to form a solution. The support is then added to the solution, and the resulting mixture is stirred for 1 minute to 10 hours. The total activator/catalyst-precursor solution volume may be greater than the pore volume of the support, but some embodiments limit the total solution volume below that needed to form a gel or slurry (about 90% to 400%, preferably about 100-200% of the pore volume). After stirring, the residual solvent is removed under vacuum, typically at ambient temperature and over 10-16 hours; however, greater or lesser times and temperatures may be used.

The catalyst precursor may also be supported absent the activator; in this case, the activator (and co-activator if needed) is added to a the liquid phase of a slurry process. For example, a solution of catalyst precursor may be mixed with a support material for a period of about 1 minute to 10 hours. The resulting precatalyst mixture may be filtered from the solution and dried under vacuum or treated with evaporation to remove the solvent. The total catalyst-precursor-solution volume may be greater than the support's pore volume, but some embodiments limit the total solution volume below that needed to form a gel or slurry (about 90% to 400%, preferably about 100-200% of the pore volume).

Additionally, two or more different catalyst precursors may be placed on the same support using any of the support methods disclosed above. Likewise, two or more activators or an activator and a co-activator, may be placed on the same support. Suitable solid particle supports are typically comprised of polymeric or refractory oxide materials, each being preferably porous. Any support material that has an average particle size greater than 10 μm is suitable for use in this invention. Various embodiments select a porous support material, such as for example, talc, inorganic oxides, inorganic chlorides, for example magnesium chloride and resinous support materials such as polystyrene polyolefin or polymeric compounds or any other organic support material and the like. Some embodiments select inorganic oxide materials as the support material including Group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as an activator component. But additional activator may also be used. In some cases, a special family of solid support commonly known as MCM-41 can also be used. MCM-41 is a new class of unique crystalline support and can be prepared with tunable pore size and tunable acidity when modified with a second component. A detailed description of this class of materials and their modification can be found in U.S. Pat. No. 5,264,203.

The support material may be pretreated by any number of methods. For example, inorganic oxides may be calcined, chemically treated with dehydroxylating agents such as aluminum alkyls and the like, or both.

As stated above, polymeric carriers will also be suitable in accordance with the invention, see for example the descriptions in WO 95/15815 and U.S. Pat. No. 5,427,991. The methods disclosed may be used with the catalyst compounds, activators or catalyst systems of this invention to adsorb or absorb them on the polymeric supports, particularly if made up of porous particles, or may be chemically bound through functional groups bound to or in the polymer chains.

Useful catalyst carriers may have a surface area of from 10-700 m$^2$/g, and or a pore volume of 0.1-4.0 cc/g and or an average particle size of 10-500 μm. Some embodiments select a surface area of 50-500 m$^2$/g, and or a pore volume of 0.5-3.5 cc/g, and or an average particle size of 20-200 μm. Other embodiments select a surface area of 100-400 m$^2$/g, and or a pore volume of 0.8-3.0 cc/g, and or an average particle size of 30-100 μm. Invention carriers typically have a pore size of 10-1000 Angstroms, alternatively 50-500 Angstroms, or 75-350 Angstroms. The metallocenes and or the metallocene/activator combinations are generally deposited on the support at a loading level of 10-100 micromoles of catalyst precursor per gram of solid support; alternately 20-80 micromoles of catalyst precursor per gram of solid support; or 40-60 micromoles of catalyst precursor per gram of support. But greater or lesser values may be used provided that the total amount of solid catalyst precursor does not exceed the support's pore volume.

The metallocenes and or the metallocene/activator combinations can be supported for gas-phase, bulk, or slurry polymerization, or otherwise as needed. Numerous support methods are known for catalysts in the olefin polymerization art, particularly alumoxane-activated catalysts; all are suitable for use herein. See, for example, U.S. Pat. Nos. 5,057,475 and 5,227,440. An example of supported ionic catalysts appears in WO 94/03056. U.S. Pat. No. 5,643,847 and WO 96/04319A which describe a particularly effective method. Both polymers and inorganic oxides may serve as supports, see U.S. Pat. Nos. 5,422,325, 5,427,991, 5,498,582 and 5,466,649, and international publications WO 93/11172 and WO 94/07928.

In another preferred embodiment, the metallocene and or activator (with or without a support) are combined with an alkylaluminum compound, preferably a trialkylaluminum compound, prior to entering the reactor. Preferably the alkylaluminum compound is represented by the formula: $R_3Al$, where each R is independently a C1 to C20 alkyl group; preferably the R groups are independently selected from the group consisting of methyl, ethyl, propyl, isopropyl, butyl, isobutyl, n-butyl, pentyl, isopentyl, n-pentyl, hexyl, isohexyl, n-hexyl, heptyl, octyl, isooctyl, n-octyl, nonyl, isononyl, n-nonyl, decyl, isodecyl, n-decyl, undecyl, isoundecyl, n-undecyl, dodecyl, isododecyl, and n-dodecyl, preferably isobutyl, n-octyl, n-hexyl, and n-dodecyl. Preferably the alkylaluminum compound is selected from tri-isobutyl aluminum, tri n-octyl aluminum, tri-n-hexyl aluminum, and tri-n-dodecyl aluminum.

Monomers

In a preferred embodiment the catalyst compounds described herein are used to polymerize or oligomerize any unsaturated monomer or monomers. Preferred monomers include $C_5$ to $C_{24}$ olefins, preferably $C_6$ to $C_{14}$ olefins, more preferably $C_8$ to $C_{12}$ olefins. In some embodiments preferred monomers include linear, branched or cyclic alpha-olefins, preferably $C_6$ to $C_{20}$ alpha-olefins, preferably $C_6$ to $C_{14}$ alpha-olefins, and more preferably $C_8$ to $C_{12}$ alpha-olefins. Preferred olefin monomers may be one or more of hexene, heptene, octene, nonene, decene, dodecene, 3-methyl-1-butene, and tetradecene.

In a preferred embodiment, the process described herein may be used to produce homo-oligomers or co-oligomers (for the purposes of this invention and the claims thereto, a co-oligmer may comprise two, three, four, or more different monomer units). Preferred oligomers produced herein include homo-oligomers or co-oligomers of any of the above monomers. In a preferred embodiment the oligomer is a homo-oligomer of any $C_8$ to $C_{12}$ alpha-olefin. Preferably the oligomer is a homo-oligomer of -hexene, 1-heptene, 1-octene, 1-nonene, 1-decene, 1-undecene, or 1-dodecene. Preferably the oligomer is a homo-oligomer of decene. In another embodiment the oligomer is a co-oligomer comprising decene and one or more of any of the monomers listed above.

The alpha-olefins used to make PAOs include, but are not limited to, $C_5$ to $C_{24}$ alpha-olefins, with the $C_6$ to $C_{14}$ alpha-olefins, such as 1-hexene, 1-heptene, 1-octene, 1-nonene, 1-decene, 1-undecene, 1-dodecene, 1-tridecene and 1-tetradecene being preferred. A preferred group of polyalphaolefins are poly-1-hexene, poly1-heptene, poly-1-octene, poly-1-nonene, poly-1-decene, poly1-undencen, poly-1-dodecene, poly-1-tridecene, and poly-1-tetradecene, although the dimers of higher olefins in the range of $C_{12}$ to $C_{18}$ can be present in the final products. Useful PAO's are preferably dimers, trimers, tetramers, pentamers, and higher oligomers or polymers with carbon numbers starting from $C_{20}$ and higher made from $C_4$ to $C_{18}$ alpha-olefins in one embodiment, and oligomers or polymers with carbon number starting from $C_{20}$ and higher made from $C_6$ to $C_{14}$ alpha-olefins in another embodiment. Suitable olefins include 1-butene, 1-pentene, 1-hexene, 1-heptene, 1-octene, 1-nonene, 1-decene, 1-undodecene and 1-dodecene, 1-tridecene, 1-tetradecene. In one embodiment, the olefin is 1-decene, and the PAO is a mixture of dimers, trimers, tetramers and pentamers (and higher) of 1-decene. In another embodiment, the olefin is 1-decene, and the PAO is a mixture of trimers, tetramers and pentamers (and higher) of 1-decene. In another embodiment, the olefin is 1-octene, and the PAO is a mixture of trimers, tetramers and pentamers (and higher) of 1-octene. In another embodiment, the olefin is 1-hexene, and the PAO is a mixture of tetramers and pentamers (and higher) of 1-hexene.

In a preferred embodiment, the PAO comprises two or more monomers, preferably three or more monomers, preferably four or more monomers, preferably five or more monomers. For example, a C8, C10, C12-linear alpha-olefin mixture, or a C6, C7, C8, C9, C10, C11, C12, C13, C14-linear alpha-olefin mixture, or a C4, C6, C8, C10, C12, C14, C16, C18-linear alpha-olefin mixture can be used as a feed.

In an alternate embodiment, the PAO comprises less than 50 mole % of C2, C3 and C4 monomers, preferably less than 40 mole %, preferably less than 30 mole %, preferably less than 20 mole %, preferably less than 10 mole %, preferably less than 5 mole %, preferably less than 3 mole %, preferably 0%. Specifically, in an alternate embodiment, the PAO comprises less than 50 mole % of ethylene, propylene and butene, preferably less than 40 mole %, preferably less than 30 mole %, preferably less than 20 mole %, preferably less than 10 mole %, preferably less than 5 mole %, preferably less than 3 mole %, preferably 0%. In another embodiment, the PAO comprises less than 40 mole % of ethylene. In another embodiment, the PAO comprises less than 40 mole % of propylene. In another embodiment, the PAO comprises less than 40 mole % of butene. In another embodiment, the PAO comprises less than 10 mole % of ethylene. In another embodiment, the PAO comprises less than 10 mole % of propylene. In another embodiment, the PAO comprises less than 10 mole % of butene. In another embodiment, the PAO comprises less than 1 mole % of ethylene. In another embodiment, the PAO comprises less than 1 mole % of propylene. In another embodiment, the PAO comprises less than 1 mole % of butene.

The alpha-olefins used herein can be produced directly from ethylene growth process as practiced by several commercial production processes, or they can be produced from Fischer-Tropsch hydrocarbon synthesis from $CO/H_2$ syngas, or from metathesis of internal olefins with ethylene, or from cracking of petroleum or Fischer-Tropsch synthetic wax at high temperature, or any other alpha-olefin synthesis routes. A preferred feed for this invention is preferably at least 80 weight % alpha-olefin (preferably linear alpha olefin), preferably at least 90 weight % alpha-olefin (preferably linear alpha olefin), more preferably 100% alpha-olefin (preferably linear alpha olefin). However, alpha-olefin mixtures can also be used as feeds in this invention, especially if the other components are internal-olefins, branched olefins, paraffins, cyclic paraffins, aromatics (such as toluene and or xylenes). These components have diluent effects and are believed to not have a substantial detrimental effect on the polymerization of alpha-olefins. In other words, the process described herein can selectively convert alpha-olefins in a mixture and leave the other components unreacted. This is particularly useful when ethylene is not present in the mixture. This technology can be used to separate out alpha-olefins from a mixture by selectively reacting them with polymerization or oligomerization catalyst systems completely eliminating the need to separate alpha-olefins from the remainder of the components in a mixed feedstream. This is economically advantageous, for example, in a process utilizing Fisher-Tropsch synthesis olefin product streams containing alpha-olefins, internal-olefins and branched olefins. Such a mixture can be fed to the oligomerization technology as described herein and to selectively react away the alpha-olefin. No separate step to isolate the alpha-olefin is needed. Another example of the utility of this process involves-alpha-olefins produced by the metathesis of internal olefins with ethylene, which may contain some internal olefins. This mixed olefin base stock feed can be reacted as is in the polymerization/oligomerization process of the present invention, which selectively converts the alpha-olefins into lube products. Thus one can use the alpha-olefin for the base stock synthesis without having to separate the alpha-olefin from internal olefin. This can bring a significant improvement in process economics.

In a preferred embodiment, the PAO's produced herein may contain monomers having branches at least 2, preferably at least 3 carbons away from the alpha-unsaturation, such 4-methyl-1-decene, 4-ethyl-1-decene, or 4-methyl-1-hexene, 4-methyl-1-pentene, etc. These olefins may be present in the linear alpha-olefins from the manufacturing process or they can be added deliberately. The copolymers of slightly branched alpha-olefins with completely linear alpha-olefins have improved low temperature properties.

In a preferred embodiment, any of the PAO's described herein may comprise at least 50 mole % 5 to 24 carbon atoms and from 0.5 to 20 mole % ethylene, where at least 80% of the ethylene present in the polyalpha-olefin is present in runs of 1 to 35 carbons or less as measured by Carbon 13 NMR. Preferably any of the PAO's described herein may comprise at least 60 mole % 5 to 24 carbon atoms (preferably at least 70 mole %, preferably at least 80 mole %, preferably at least 85 mole %, preferably at least 90 mole %, preferably at least 95 mole %) and from 0.5 to 20 mole % ethylene (preferably from 1 to 15 mole %, preferably from 2 to 10 mole %, preferably form 2 to 5 mole %), where at least 80% (preferably at least 85%, preferably at least 90%, preferably at least 95%, preferably at least 98%, preferably 100%) of the ethylene present in the polyalpha-olefin is present in runs of 1 to 35 carbons (preferably 1 to 30, preferably 1 to 25, preferably 1 to 20, preferably 1 to 15, preferably 1 to 10, preferably 1 to 5) as measured by Carbon 13 NMR.

Polymerization/Oligomerization Process

Many polymerization/oligomerization processes and reactor types used for metallocene-catalyzed polymerizations or oligomerizations such as solution, slurry, and bulk polymerization or oligomerization processed can be used in this invention. In some embodiments, if a solid or supported catalyst is used, a slurry or continuous fixed bed or plug flow process is suitable. In a preferred embodiment, the monomers are contacted with the metallocene compound and the activator in the solution phase, bulk phase, or slurry phase, preferably in a continuous stirred tank reactor, continuous tubular reactor, or a batch reactor. In a preferred embodiment, the temperature in any reactor used herein is from $-10°$ C. to $250°$ C., preferably from $30°$ C. to $220°$ C., preferably from $50°$ C. to $180°$ C., preferably from $60°$ C. to $170°$ C. In a preferred embodiment, the pressure in any reactor used herein is from 0.1 to 100 atmospheres, preferably from 0.5 to 75 atmospheres, preferably from 1 to 50 atmospheres. In another embodiment, the pressure is any reactor used herein is from 1 to 50,000 atmospheres, preferably 1 to 25,000 atmospheres. In another embodiment, the monomer(s), metallocene and activator are contacted for a residence time of 1 second to 100 hours, preferably 30 seconds to 50 hours, preferably 2 minutes to 6 hours, preferably 1 minute to 4 hours. In another embodiment solvent or diluent is present in the reactor and is preferably selected from the group consisting of butanes, pentanes, hexanes, heptanes, octanes, nonanes, decanes, undecanes, dodecanes, tridecanes, tetradecanes, pentadecanes, hexadecanes, toluene, o-xylene, m-xylene, p-xylene, ethylbenzene, isopropylbenzene, and n-butylbenzene; preferably toluene and or xylenes and or ethylbenzene, normal paraffins (such as Norpar solvents available for ExxonMobil Chemical Company in Houston, Tex.), or isoparaffin solvents (such as Isopar solvents available for ExxonMobil Chemical Company in Houston, Tex.). These solvents or diluents are usually pre-treated in same manners as the feed olefins.

Typically, in the processes of this invention, one or more transition metal compounds, one or more activators, and one or more monomers are contacted to produce polymer or oligomer. These catalysts may be supported and as such will be particularly useful in the known slurry, solution, or bulk operating modes conducted in single, series, or parallel reactors. If the catalyst, activator or co-activator is a soluble compound, the reaction can be carried out in a solution mode. Even if one of the components is not completely soluble in the reaction medium or in the feed solution, either at the beginning of the reaction or during or at the later stages of the reaction, a solution or slurry type operation is still applicable. In any instance, the catalyst components, dissolved or suspended insolvents, such as toluene or other conveniently available aromatic solvents, or in aliphatic solvent, or in the feed alpha-olefin stream, are fed into the reactor under inert atmosphere (usually nitrogen or argon blanketed atmosphere) to allow the polymerization or oligomerization to take place. The polymerization or oligomerization can be run in a batch mode, where all the components are added into a reactor and allowed to react to a pre-designed degree of conversion, either to partial conversion or full conversion. Subsequently, the catalyst is deactivated by any possible means, such as exposure to air or water, or by addition of alcohols or solvents containing deactivating agents. The polymerization or oligomerization can also be carried out in a semi-continuous operation, where feeds and catalyst system components are continuously and simultaneously added to the reactor so as to maintain a constant ratio of catalyst system components to feed olefin(s). When all feeds and catalyst components are added, the reaction is allowed to proceed to a pre-determined stage. The reaction is then discontinued by catalyst deactivation in the same manner as described for batch operation. The polymerization or oligomerization can also be carried out in a continuous operation, where feeds and catalyst system components are continuously and simultaneously added to the reactor so to maintain a constant ratio of catalyst system and feed olefins. The reaction product is continuously withdrawn from the reactor, as in a typical continuous stirred tank reactor (CSTR) operation. The residence times of the reactants are controlled by a pre-determined degree of conversion. The withdrawn product is then typically quenched in the separate reactor in a similar manner as other operation. In a preferred embodiment, any of the processes to prepare PAO's described herein are continuous processes. Preferably the continuos process comprises the steps of a) continuously introducing a feed stream comprising at least 10 mole % of the one or more C5 to C24 alpha-olefins into a reactor, b) continuously introducing the metallocene compound and the activator into the reactor, and c) continuously withdrawing the polyalpha-olefin from the reactor. In another embodiment, the continuous process comprises the step of maintaining a partial pressure of hydrogen in the reactor of 200 psi (1379 kPa) or less, based upon the total pressure of the reactor, preferably 150 psi (1034 kPa) or less, preferably 100 psi (690 kPa) or less, preferably 50 psi (345 kPa) or less, preferably 25 psi (173 kPa) or less, preferably 10 psi (69 kPa) or less. Alternately the hydrogen, if present is present in the reactor at 1000 ppm or less by weight, preferably 750 ppm or less, preferably 500 ppm or less, preferably 250 ppm or less, preferably 100 ppm or less, preferably 50 ppm or less, preferably 25 ppm or less, preferably 10 ppm or less, preferably 5 ppm or less. Alternately the hydrogen, if present, is present in the feed at 1000 ppm or less by weight, preferably 750 ppm or less, preferably 500 ppm or less, preferably 250 ppm or less, preferably 100 ppm or less, preferably 50 ppm or less, preferably 25 ppm or less, preferably 10 ppm or less, preferably 5 ppm or less.

Preferred reactors range in size from 2 ml and up. Usually, it is preferable to use reactors larger than one liter in volume for commercial production. The production facility may have one single reactor or several reactors arranged in series or in parallel or in both to maximize productivity, product properties and general process efficiency. The reactors and associated equipments are usually pre-treated to ensure proper reaction rates and catalyst performance. The reaction is usually conducted under inert atmosphere, where the catalyst system and feed components will not be in contact with any catalyst deactivator or poison which is usually polar oxygen, nitrogen, sulfur or acetylenic compounds.

One or more reactors in series or in parallel may be used in the present invention. The transition metal compound, activator and when required, co-activator, may be delivered as a solution or slurry in a solvent or in the alpha-olefin feed stream, either separately to the reactor, activated in-line just prior to the reactor, or preactivated and pumped as an activated solution or slurry to the reactor. Polymerizations/oligomerizations are carried out in either single reactor operation, in which monomer, or several monomers, catalyst/activator/co-activator, optional scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors. In one preferred embodiment, the precatalyst is activated in the reactor in the presence of olefin. In another embodiment, the precatalyst such as the dichloride form of the metallocenes is pre-treated with alkylalumum reagents, especially, triisobutylaluminum, tri-n-hexylaluminum and/or tri-n-octylaluminum, followed by charging into the reactor containing other catalyst component and the feed olefins, or followed by pre-activation with the other catalyst component to give the fully activated catalyst, which is then fed into the reactor containing feed olefins. In another alternative, the pre-catalyst metallocene is mixed with the activator and/or the co-activator and this activated catalyst is then charged into reactor, together with feed olefin stream containing some scanvenger or co-activator. In another alternative, the whole or part of the co-activator is pre-mixed with the feed olefins and charged into the reactor at the same time as the other catalyst solution containing metallocene and activators and/or co-activator.

In some embodiments, a small amount of poison scavenger, such as trialkylaluminum (trimethylaluminum, triethylaluminum, triisopropylaluminum, triisobutylaluminum, tri-n-hexylaluminum, tri-n-octylaluminum) or methylalumoxane is added to the feed olefin stream to further improve catalyst activity. In a preferred embodiment, the monomers are contacted with an alkylaluminum compound, preferably a trialkylaluminum compound, prior to being introduced into the reactor. In another preferred embodiment, the metallocene and or activator are combined with an alkylaluminum compound, preferably a trialkylaluminum compound, prior to entering the reactor. Preferably the alkylaluminum compound is represented by the formula: $R_3Al$, where each R is independently a C1 to C20 alkyl group, preferably the R groups are independently selected from the group consisting of methyl, ethyl, propyl, isopropyl, butyl, isobutyl, n-butyl, pentyl, isopentyl, n-pentyl, hexyl, isohexyl, n-hexyl, heptyl, octyl, isocotyl, n-octyl, nonyl, isononyl, n-nonyl, decyl, isodecyl, n-cecyl, undecyl, isoundecyl, n-undecyl, dodecyl, isododecyl, and n-dodecyl, preferably isobutyl, n-octyl, n-hexyl, and n-dodecyl. Preferably the alkylaluminum compound is selected from tri-isobutylaluminum, tri n-octylaluminum, tri-n-hexylaluminum, and tri-n-dodecylaluminum.

In one embodiment of any of the process described herein the feed olefins and or solvents are treated to remove catalyst poisons, such as peroxides, oxygen or nitrogen-containing organic compounds or acetylenic compounds. The treatment of the linear alpha-olefin with an activated 13X molecular sieve and a de-oxygenate catalyst, i.e., a reduced copper catalyst, increased catalyst productivity more than 10-fold. Alternatively, the feed olefins and or solvents are treated with an activated molecular sieve, such as 3A, 4A, 8A or 13X molecular sieve, and/or in combination with an activated alumina or an activated de-oxygenated catalyst. Such treatment will increase catalyst productivity 2- to 10-fold or more. The improved process also includes special treatment of the feed olefins to remove catalyst poisons, such as peroxides, oxygen, sulfur or nitrogen-containing organic compounds or other trace impurities. This treatment can increase catalyst productivity substantially (typically more than 10-fold). Preferably the feed olefins are contacted with a molecular sieve, activated alumina, silica gel, oxygen removing catalyst, and or purifying clays to reduce the heteroatom-containing compounds in the feed, preferably th below 50 ppm, preferably below 10 ppm.

The catalyst compositions can be used individually or can be mixed with other known polymerization catalysts to prepare polymer or oligomer blends. Monomer and catalyst selection allows polymer or oligomer blend preparation under conditions analogous to those using individual catalysts. Polymers having increased MWD are available from polymers made with mixed catalyst systems and can thus be achieved. Mixed Catalyst can comprise two or more catalyst precursors and or two or more activators.

Generally, when using metallocene catalysts, after pretreatment of feed olefins, solvents, diluents and after precautions to keep the catalyst component stream(s) and reactor free of impurities, the reaction should proceed well. In some embodiments, when using metallocene catalysts, particularly when they are immobilized on a support, the complete catalyst system will additionally comprise one or more scavenging compounds. Here, the term scavenging compound means a compound that removes polar impurities from the reaction environment. These impurities adversely affect catalyst activity and stability. Typically, purifying steps are usually used before introducing reaction components to a reaction vessel. But such steps will rarely allow polymerization or oligomerization without using some scavenging compounds. Normally, the polymerization process will still use at least small amounts of scavenging compounds.

Typically, the scavenging compound will be an organometallic compound such as the Group-13 organometallic compounds of U.S. Pat. Nos. 5,153,157, 5,241,025 and WO-A-91/09882, WO-A-94/03506, WO-A-93/14132, and that of WO 95/07941. Exemplary compounds include triethylaluminum, triethylborane, tri-iso-butylaluminum, diisobutylaluminum hydride, methylalumoxane, iso-butylalumoxane, and tri-n-octylaluminum. Those scavenging compounds having bulky or $C_6$-$C_{20}$ linear hydrocarbyl substituents connected to the metal or metalloid center usually minimize adverse interaction with the active catalyst. Examples include triethylaluminum, but more preferably, bulky compounds such as tri-iso-butyl aluminum, tri-iso-prenyl aluminum, and long-chain linear alkyl-substituted aluminum compounds, such as tri-n-hexyl aluminum, tri-n-octyl aluminum, or tri-n-dodecyl aluminum. When alumoxane is used as the activator, any excess over that needed for activation will scavenge impurities and additional scavenging compounds may be unnecessary. Alumoxanes also may be added in scavenging quantities with other activators, e.g., methylalumoxane, $[Me_2HNPh]^+[B(pfp)_4]^-$ or $B(pfp)_3$, where pfp is perfluorophenyl ($C_6F_5$), Me is methyl and Ph is phenyl.

In a preferred embodiment ethylene is present in the feed at 10 mole % or less, preferably 0.5 to 8 moles %, preferably 0.5 to 5 mole %, preferably from 1 to 3 mole %

The PAO's described herein can also be produced in homogeneous solution processes. Generally this involves polymerization or oligomerization in a continuous reactor in which the polymer formed and the starting monomer and catalyst materials supplied, are agitated to reduce or avoid concentration or temperature gradients. Temperature control in the reactor is generally obtained by balancing the heat of polymerization and with reactor cooling by reactor jackets or cooling coils or a cooled side-stream of reactant to cool the contents of the reactor, auto refrigeration, pre-chilled feeds, vaporization of liquid medium (diluent, monomers or solvent) or combinations of the above. Adiabatic reactors with pre-chilled feeds may also be used. The reactor temperature depends on the catalyst used and the product desired. Higher temperatures tend to give lower molecular weights and lower temperatures tend to give higher molecular weights, however this is not a hard and fast rule. In general, the reactor temperature preferably can vary between about 0° C. and about 300° C., more preferably from about 10° C. to about 230° C., and most preferably from about 25° C. to about 200° C. Usually, it is important to control the reaction temperature as pre-determined. In order to produce fluids with narrow molecular distribution, such as to promote the highest possible shear stability, it is useful to control the reaction temperature to obtain minimum of temperature fluctuation in the reactor or over the course of the reaction time. If multiple reactors are used in series or in parallel, it is useful to keep the temperature constant in a pre-determined value to minimize any broadening of molecular weight distribution. In order to produce fluids with broad molecular weight distribution, one can adjust the reaction temperature swing or fluctuation, or as in series operation, the second reactor temperature is preferably higher than the first reactor temperature. In parallel reactor operation, the temperatures of the two reactors are independent. Or one can use two types of metallocene catalysts.

The pressure in any reactor used herein can vary from about 0.1 atmosphere to 100 atmosphere (1.5 psi to 1500 psi), preferably from 0.5 bar to 75 atm (8 psi-1125 psi), most preferably from 1.0 to 50 atm (15 psi to 750 psi). The reaction can be carried out under the atmosphere of nitrogen or with some hydrogen. Sometimes a small amount of hydrogen is added to the reactor to improve the catalyst. The amount of hydrogen is preferred to keep at such a level to improve catalyst productivity, but not induce any hydrogenation of olefins, especially the feed alpha-olefins because the conversion of alpha-olefins into saturated paraffins is very detrimental to the efficiency of the process. The amount of hydrogen partial pressure is preferred to be kept low, less than 100 psi, prefer less than 50 psi, preferably less than 25 psi, preferably less than 10 psi, preferably less than 5 psi, preferably less than 1 psi. In a particularly preferred embodiment in any of the process described herein the concentration of hydrogen in the reactant phase is less than 100 ppm, preferably less than 50 ppm, preferably less than 10 ppm, preferably less than 1 ppm. In a particularly preferred embodiment in any of the process described herein the concentration of hydrogen in the reactor is kept at a partial pressure of 200 psi (1379 kPa) or less, based upon the total pressure of the reactor, preferably 150 psi (1034 kPa) or less, preferably 100 psi (690 kPa) or less, preferably 50 psi (345 kPa) or less, preferably 10 psi (69 kPa) or less. Alternately, in any process described herein hydrogen, if present, is present in the reactor and or feed at 1000 ppm or less by weight, preferably 750 ppm or less, preferably 500 ppm or less, preferably 250 ppm or less, preferably 100 ppm or less, preferably 50 ppm or less, preferably 25 ppm or less, preferably 10 ppm or less, preferably 5 ppm or less.

The reaction time or reactor residence time is usually dependent on the type of catalyst, the amount of catalyst used, and the desired conversion level. Different metallocenes have different activities. Usually, a higher degree of alkyl substitution on the cyclopentadienyl ring, or bridging improves catalyst productivity. Catalysts such as bis(1,2,3,4-tetramethylcyclopentadienyl)zirconium dichloride or bis(1, 2,4-trimethylcyclopentadienyl)zirconium dichloride, (1,2,3, 4-tetramethylcyclopentadienyl) (1,3-di methylcyclopentadienyl)zirconium dichloride or (1,2,4-trimethylcyclopentadienyl) (1,3-di methylcyclopentadienyl)zirconium dichloride or their dialkyl analogs have desirable high productivity and stability than unsubstituted metallocenes. Certain bridged and bridged with substitution catalysts, such as the di-halides or dialkyls of dimethylsilylbis[indenyl]zirconium or dimethylsilylbis[tetrahydro-indenyl]zirconium dimethylsilylbis[1-methylindenyl]zirconium or their hafnium analogs, etc. Usually the amount of catalyst components used is determinative. High amount of catalyst loading tends to gives high conversion at short reaction time. However, high amount of catalyst usage make the production process uneconomical and difficult to manage the reaction heat or to control the reaction temperature. Therefore, it is useful to choose a catalyst with maximum catalyst productivity to minimize the amount of metallocene and the amount of activators needed. When the catalyst system is metallocene plus methylalumoxane, the range of methylalumoxane used is typically in the range of 0.1 milligram (mg) to 500 mg/g of alpha-olefin feed. A more preferred range is from 0.05 mg to 10 mg/g of alpha-olefin feed. Furthermore, the molar ratios of the aluminum to metallocene (Al/M molar ration) range from 2 to 4000, preferably 10 to 2000, more preferably 50 to 1000, preferably 100 to 500. When the catalyst system is metallocene plus a Lewis Acid or an ionic promoter with NCA component, the metallocene use is typically in the range of 0.01 microgram to 500 micrograms of metallocene component/gram of alpha-olefin feed. Usually the preferred range is from. 1 microgram to 100 microgram of metallocene component per gram of alpha-olefin feed. Furthermore, the molar ratio of the NCA activator to metallocene is in the range from 0.1 to 10, preferably 0.5 to 5, preferably 0.5 to 3. If a coactivator of alkylaluminum compound is used, the molar ratio of the Al to metallocene is in the range from 1 to 1000, preferably 2 to 500, preferably 4 to 400.

Typically one prefers to have the highest possible conversion (close to 100%) of feed alpha-olefin in shortest possible reaction time. However, in CSTR operation, sometimes it is beneficial to run the reaction at an optimum conversion, which is slightly less than 100% conversion. There are also occasions, when partial conversion is more desirable when the narrowest possible MWD of the product is desirable because partial conversion can avoid a MWD broadening effect. If the reaction is conducted to less than 100% conversion of the alpha-olefin, the unreacted starting material after separation from other product and solvents/diluents can be recycled to increase the total process efficiency.

Desirable residence times for any process described herein are in the range from 1 minutes to 20 hours, typically 5 minutes to 10 hours. Each of these processes may also be employed in single reactor, parallel or series reactor configurations. The liquid processes comprise contacting olefin monomers with the above described catalyst system in a suitable diluent or solvent and allowing said monomers to react for a sufficient time to produce the desired polymers or oligomers. Hydrocarbon solvents both aliphatic and aromatic are suitable. Aromatics such as toluene, xylenes, ethylbenzene, propylbenzene, cumene, t-butylbenzene are suitable. Alkanes, such as hexane, heptane, pentane, isopentane, and octane, Norpar or Isopar solvents from ExxonMobil Chemial Company in Houston, Tex. are also suitable. Generally, toluene is most suitable to dissolve catalyst components. Norpar, Isopar solvent or hexanes are preferred as reaction diluents. Oftentimes, a mixture of toluene and Norpar or Isopar is used as diluent or solvent.

The process can be carried out in a continuous stirred tank reactor, batch reactor, or plug flow reactor, or more than one reactor operated in series or parallel. These reactors may have or may not have internal cooling and the monomer feed may or may not be refrigerated. See the general disclosure of U.S. Pat. No. 5,705,577 for general process conditions.

When a solid supported catalyst is used for the conversion, a slurry polymerization/oligomerization process generally operates in the similar temperature, pressure and residence time range as described previously. In a slurry polymerization or oligomerization, a suspension of solid catalyst, promoters, monomer and comonomers are added. The suspension including diluent is intermittently or continuously removed from the reactor. The catalyst is then separated from the product by filtration, centrifuge or settlement. The fluid is then distilled to remove solvent, any unreacted components and light product. A portion or all of the solvent and unreacted component or light components can be recycled for reuse.

If the catalyst used is un-supported, is a solution catalyst, when the reaction is complete (such as in a batch mode), or when the product is withdrawn from the reactor (such as in a CSTR), the product may still contain soluble, suspended or mixed catalyst components. These components are preferably deactivated or removed. Any of the usual catalyst deactivation methods or aqueous wash methods can be used to remove the catalyst component. Typically, the reaction is deactivated by addition of stoichiometric amount or excess of air, moisture, alcohol, isopropanol, etc. The mixture is then washed with dilute sodium hydroxide or with water to remove catalyst components. The residual organic layer is then subjected to distillation to remove solvent, which can be recycled for reuse. The distillation can further remove any light reaction product from C18 and less. These light components can be used as diluent for further reaction. Or they can be used as olefinic raw material for other chemical synthesis, as these light olefin product have vinylidene unsaturation, most suitable for further functionalization to convert in high performance fluids. Or these light olefin products can be hydrogenated to be used as high quality paraffinic solvents.

Polymerization or oligomerization in absence of hydrogen is also advantageous to provide polymers or oligomers with high degree of unsaturated double bonds. These double bonds can be easily converted into functionalized fluids with multiple performance features. Examples for converting these polymers with MW greater than 300 can be found in preparation of ashless dispersants, by reacting the polymers with maleic anhydride to give PAO-succinic anhydride which can then reacted with amines, alcohols, polyether alcohols to convert into dispersants. Examples for such conversion can be found in the book "Lubricant Additives: Chemistry and Application," ed. By Leslie R. Rudnick, p. 143-170.

In another embodiment, any of polyalphaolefins produced herein is hydrogenated. In particular the polyalpha-olefin is preferably treated to reduce heteroatom containing compounds to less than 600 ppm, and then contacted with hydrogen and a hydrogenation catalyst to produce a polyalphaolefin having a bromine number less than 1.8. In a preferred embodiment, the treated polyalpha-olefin comprises 100 ppm of heteroatom containing compounds or less, preferably 10 ppm of heteroatom containing compounds or less. (A heteroatom containing compound is a compound containing at least one atom other than carbon and hydrogen.) Preferably the hydrogenation catalyst is selected from the group consisting of supported Group 7, 8, 9, and 10 metals, preferably the hydrogenation catalyst selected from the group consisting of one or more of Ni, Pd, Pt, Co, Rh, Fe, Ru, Os, Cr, Mo, and W, supported on silica, alumina, clay, titania, zirconia, or mixed metal oxide supports. A preferred hydrogenation catalyst is nickel supported on kieselguhr, or platinum or palladium supported on alumina, or cobalt-molydenum supported on alumina. Usually, a high nickel content catalyst, such as 60% Ni on Keiselguhr catalyst is used, or a supported catalyst with high amount of Co—Mo loading. Alternately, the hydrogenation catalyst is nickel supported on keisleghur, silica, alumina, clay or silica-alumina.

In a preferred embodiment the polyalpha-olefin is contacted with hydrogen and a hydrogenation catalyst at a temperature from 25 to 350° C., preferably 100 to 300° C. In another preferred embodiment the polyalpha-olefin is contacted with hydrogen and a hydrogenation catalyst for a time period from 5 minutes to 100 hours, preferably from 5 minutes to 24 hours. In another preferred embodiment the poly-alpha-olefin is contacted with hydrogen and a hydrogenation catalyst at a hydrogen pressure of from 25 psi to 2500 psi, preferably from 100 to 2000 psi. In another preferred embodiment the hydrogenation process reduces the number of mm triad groups in a polyalpha-olefin by 1 to 80%. Preferably the PAO has 10 to 80% less mm triad groups than the polyalpha-olefin prior to contact with the hydrogen and hydrogenation catalyst. For further information on hydrogenation of PAO's please see U.S. Pat. No. 5,573,657 and "Lubricant Base Oil Hydrogen Refining Processes" (page 119 to 152 of Lubricant Base Oil and Wax Processing, by Avilino Sequeira, Jr., Marcel Dekker, Inc., NY, 1994.

This hydrogenation process can be accomplished in a slurry reactor in a batch operation or in a continuous stirred tank reactor (CSTR), where the catalyst in 0.001 wt % to 20 wt % of the PAO feed or preferably 0.01 to 10 wt %, hydrogen and the polyalpha-olefins are continuously added to the reactor to allow for certain residence time, usually 5 minutes to 10 hours to allow complete hydrogenation of the unsaturated olefins and to allow proper conversion of the mm diads. The amount of catalyst added is usually very small just to compensate for the catalyst deactivation. The catalyst and hydrogenated PAO are continuously withdrawn from the reactor. The product mixture was then filtered, centrifuged or settled to remove the solid hydrogenation catalyst. The catalyst can be regenerated and reused. The hydrogenated PAO can be used as is or further distilled or fractionated to the right component if necessary. In some cases, when the hydrogenation catalyst show no catalyst deactivation over long term operation, the stir tank hydrogenation process can be carried out in a manner where a fixed amount of catalyst is maintained in the reactor, usually 0.1 wt % to 10% of the total reactant, and only hydrogen and PAO feed are continuously added at certain feed rate and only hydrogenated PAO was withdrawn from the reactor.

The hydrogenation process can also be accomplished by a fixed bed process, in which the solid catalyst is packed inside a tubular reactor and heated to reactor temperature. Hydrogen and PAO feed can be fed through the reactor simultaneously from the top or bottom or countercurrently to maximize the contact between hydrogen, PAO and catalyst and to allow best heat management. The feed rate of the PAO and hydrogen are adjusted to give proper residence to allow complete hydrogenation of the unsaturated olefins in the feed and to allow desirable conversion of mm triads in the process. The hydrogenated PAO fluid can be used as is or further distilled or fractionated to give the right component, if necessary. Usually, the finished hydrocarbon PAO fluids have bromine number less than 2 and have reduced amount of mm triads than the unhydrogenated PAO.

The new poly-alpha-olefins when used alone or blended with other fluid has unique lubrication properties.

In another embodiment, a novel lubricant of the present invention comprises the PAO's produced in this invention, together with one or more other base stocks, including Group I to Group V base stocks with viscosity range from 1.5 to 100 cSt at 100° C. to formulate suitable viscosity grades. In addition, additives of one or more of: thickeners, VI improvers, antioxidants, anti-wear additives, detergent/dispersant/inhibitor (DDI) packages, and/or anti-rust additives may be added. In a preferred embodiment the PAO's produced herein are combined with one or more of dispersants, detergents, friction modifiers, traction improving additives, demulsifiers, defoamants, chromophores (dyes), and/or haze inhibitors. These fully formulated lubricants can be used in automotive crank case oil (engine oil), industrial oil, grease, or gas turbine engine oil. These are examples of additives used in finished lubricant formulations. Additional information on the use of PAO's in the formulations of full synthetic, semi-synthetic or part synthetic lubricant or functional fluids can be found in "Synthetic Lubricants and High-Performance Functional Fluids", 2nd Ed. L. Rudnick, etc. Marcel Dekker, Inc., N.Y. (1999). Additional information on additives used in product formulation can be found in "Lubricants and Lubrications, Ed. By T. Mang and W. Dresel, by Wiley-VCH GmbH, Weinheim 2001.

EXAMPLES

The following examples are for purposes of illustration only and are non-limiting examples.

The 1-decene used for all of the experiments was purified by mixing 1 liter of untreated raw material with 20 grams of activated 13× molecular sieve, (which was activated by calcining at 200° C. for at least four hours under a stream of purging dry nitrogen gas), and 10 grams of Oxi-Clear catalyst (purchased from Altech Associates, Inc of Deerfield, Ill. 60115) for at least two days inside a glove box under a dry, inert atmosphere of nitrogen. The molecular sieve and de-oxygenation catalyst were then removed by filtration in the glove box to provide purified 1-decene. Alternatively, the feeds were purified by passing through a bed of activated 13X molecular sieve alone under nitrogen atmosphere.

The polymerization/oligomerization reaction was carried out under nitrogen ($N_2$) inert atmosphere or argon inert atmosphere. In a small scale screening experiment, 2.2 grams of purified 1-decene was added into a small stainless steel reactor fitted with glass liner with a total reactor volume of 5.5 ml, an agitator and a temperature controller, followed by addition of 0.668 ml of methylalumoxane (MAO) in toluene solution which was prepared by diluting 10 wt % MAO in toluene solution to a dilute solution containing 8.68 mg methylauminoxane per ml of solution volume. The reactor was then heated to the desired reaction temperature and the desired amount of metallocene catalyst in toluene was added to initiate the polymerization reaction. After 3 hours, the reaction was quenched by addition of carbon dioxide ($CO_2$) gas of equal moles as the metallocene catalyst. The polymerization/oligomerization product was isolated by stripping the reactor contents, from about room temperature to 50° C., under high vacuum for at least 2 hours to remove solvent, unreacted starting material and dimer, i.e., any component having less than thirty carbon atoms. The product properties, including molecular weight and Mw/Mn, were analyzed by gel permeation chromatography using tetrahydrofuran as the solvent and polystyrene as the calibration standard. The residual fluid viscosity was calculated by a correlation equation, which correlated the Mw by GPC to fluid viscosity. The correlation equation used was:

$$Kv@100° C. \text{ in } cSt = 0.13 + 0.005578 * Mw + 1.37 * 10^{-6} * (Mw)^2$$

Catalyst productivity was calculated as grams of product, which is usually the C30 and higher component when 1-decene is used as feed, per gram of MAO. In the case when an NCA was used as co-catalyst, the catalyst productivity was calculated in gram of product (C30 and higher) per gram of metallocene catalyst (not including the NCA or co-activator).

Examples 1 through 10 were conducted generally as described above, with additional experimental details provided in Table 1 below.

TABLE 1

Reactions were carried out using 0.1 micromole metallocene catalyst, Al/Zr molar ratio = 1000

| | Example number | | | | | | | | | |
|---|---|---|---|---|---|---|---|---|---|---|
| | 1 | 2 | 3 | 4 | 5 | 6 | 7 | 8 | 9 | 10 |
| catalyst type* | A | B | C | D | E | F | G | E | F | G |
| reaction temperature, ° C. | 100 | 100 | 100 | 100 | 100 | 100 | 100 | 50 | 50 | 50 |
| product yield, wt % | 65 | 65 | 71 | 29 | 88 | 76 | 29 | 88 | 41 | 94 |
| g product/g MAO | 190 | 190 | 207 | 86 | 259 | 224 | 86 | 259 | 121 | 276 |
| Mw g/mol | 507 | 514 | 791 | 493 | 5860 | 1436 | 23935 | 12300 | 8280 | 27560 |
| Mw/Mn | 1.1 | 1.1 | 1.2 | 1.1 | 1.8 | 1.4 | 1.5 | 1.8 | 2 | 2 |
| estimated 100° C. vis, cSt** | 3.3 | 3.4 | 5.4 | 3.2 | 80 | 11 | 918 | 276 | 140 | 1194 |

Reactions were carried out using 0.1 micromole catalyst, Al/Zr molar ratio = 1000.
*Catalyst type
A biscyclopentadienylzirconium dichloride
B dimethylsilylbis(cyclopentadienyl)zirconium dichloride
C bis(1,3-dimethylcyclopentadienyl)zirconium dichloride
D iso-propylidenebis(cyclopentadienyl)zirconium dichloride
E rac-ethylenebis(1-indenyl)zirconium dichloride
F rac-dimethylsilylbis(tetrahydroindenyl)zirconium dichloride
G diphenylmethylidene(cylcopentadienyl)(9-fluorenyl)zirconium dichloride
**Viscosity was calculated based on Mw determined by GPC using the formula: $Kv@100° C. \text{ in } cSt = 0.13 + 0.005578 * Mw + 1.37 *^{10-6} * (Mw)^2$ Examples 11 through 17 were conducted generally as described above, with additional experimental details provided in Table 2 below.

TABLE 2

Reactions were carried out at 100° C., using 0.1 micromole metallocene catalyst, Al/Zr molar ratio = 250

| | Example number | | | | | | |
|---|---|---|---|---|---|---|---|
| | 11 | 12 | 13 | 14 | 15 | 16 | 17 |
| Catalyst type* | H | I | J | K | C | L | B |
| product yield, wt %*** | 21.7 | 28.3 | 15.9 | 17.3 | 38.1 | 23.2 | 27.6 |
| g product/g MAO | 329 | 430 | 241 | 262 | 578 | 352 | 419 |
| Mw (g/mol) | 1715 | 1674 | 1807 | 1862 | 2305 | 2333 | 2331 |
| Mw/Mn | 1.1 | 1.1 | 1.1 | 1.1 | 1.2 | 1.2 | 1.2 |
| Estimated 100° C. vis, cSt** | 4.0 | 3.8 | 4.4 | 4.7 | 6.7 | 6.9 | 6.9 |

Catalyst type
H bis(methylcyclopentadienyl)zirconium dichloride
I bis(ethylcyclopentadienyl)zirconium dichloride
J bis(n-butylcyclopentadienyl)zirconium dichloride
K bis(n-dodecylcyclopentadienyl)zirconium dichloride
L (methylcyclopentadienyl)(propylcyclopentadienyl)zirconium dichloride
**Viscosity was calculated based on Mw determined by GPC using the formula: $Kv@100° C. \text{ in } cSt = 0.13 + 0.005578 * Mw + 1.37 *^{10-6} * (Mw)^2$
***product yield weight % = 100 (residual weight/feed 1-decene weight)

Examples 18 through 26 were conducted generally as described above, with additional experimental details provided in Table 3 below.

TABLE 3

Reactions were carried out at 100° C., using 0.1 micromole metallocene catalyst, Al/Zr molar ratio = 250

| | Sample number. | | | | | | | | |
|---|---|---|---|---|---|---|---|---|---|
| | 18 | 19 | 20 | 21 | 22 | 23 | 24 | 25 | 26 |
| Catalyst type* | M | N | O | P | F | G | Q | R | S |
| product yield, wt % | 28.5 | 20.6 | 52.3 | 5.5 | 61.9 | 11.3 | 27.4 | 3.2 | 5.1 |
| g polymer/g MAO | 433 | 313 | 793 | 83 | 939 | 172 | 415 | 48 | 77 |
| Mw | 11287 | 11259 | 19822 | 10214 | 24369 | 298921 | 15278 | 14431 | 37372 |
| Mw/Mn | 1.1 | 1.1 | 1.3 | 1.1 | 1.3 | 1.8 | 1.2 | 1.2 | 1.9 |
| Estimated 100° C. viscosity, cSt** | 90 | 90 | 243 | 76 | 353 | 44524 | 153 | 138 | 781 |

Catalyst type:
M bis(indenyl)zirconium dichloride
N cyclopentadienyl(indenyl)zirconium dichloride
O bis(1,2,4-trimethylcyclopentadienyl)zirconium dichloride
P bis(pentamethylcyclopentadienyl)zirconium dichloride
Q bis(1-methyl-3-n-propylcyclopentadienyl)zirconium dichloride
R bis(cyclopentadienyl)hafnium dichloride
S bis(indenyl)hafnium dichloride
**Viscosity was calculated based on Mw determined by GPC using the formula: Kv@100° C. in cSt = 0.13 + 0.005578 * Mw + 1.37 *$10^{-6}$ * $(Mw)^2$
***product yield weight % = 100 (residual weight/feed 1-decene weight)

Figure 4:
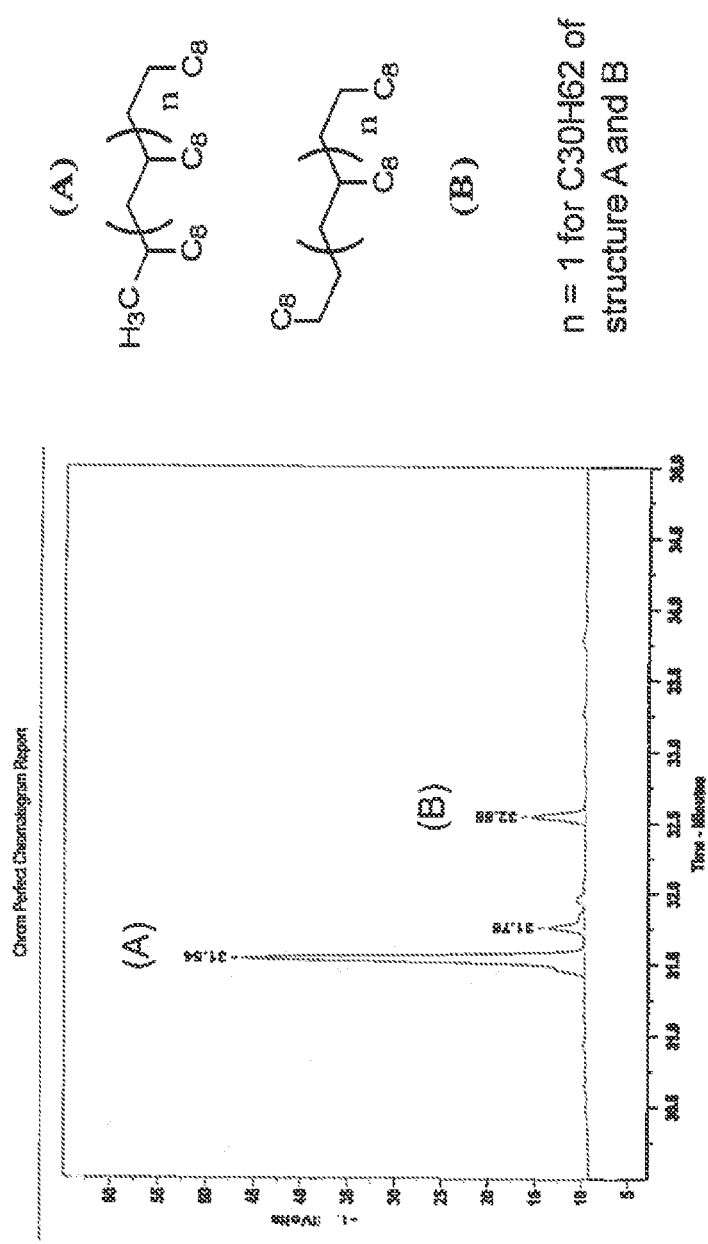
FIG. 4 is a gas chromatograph for the C30H62 fraction of example 31.

Example 27 to 32. In this set of experiments, the reaction was carried out by adding 180 gram of purified 1-decene and a catalyst solution, prepared by dissolving 2.017 millimole methylalumoxane (1.17 gram of a 10 wt % in toluene solution) and 8.07 micromole of metallocene catalyst in 58 gram of toluene solvent, into a 500 ml round bottom flask containing 180 gram purified 1-decene heated to reaction temperature and equipped with stirrer and temperature controller. The reaction mixture was maintained at proper reaction temperature. After 4-10 hours, the reaction was quenched by addition of 3-ml isopropanol, dilute HCl solution and washed with 5% NaOH solution. The organic layer was separated and distilled under full vacuum to remove any C20 and lower components. The C30 and higher components were then hydrogenated under typical hydrogenation conditions using Nickel on Kieselguhr catalyst at 200° C., 800 psi hydrogen for 4-8 hours. After hydrogenation, the bromine number of the samples were below 1. The composition of the product was then analyzed by gas chromatograph equipped with a 60 meter DB1 column (initial temperature, 70° C./0 minute, 10° C./minute to 320° C.). A typical gas chromatograph for the $C_{30}H_{62}$ component of example 31 is shown in FIG. 4. The major components A and B were determined by comparison of the GC retention time to the known compounds. Component A is believed to be produced by hydrogenation of the olefin A" produced from simple 1,2-connections of each 1-decene molecule. Component B is believed to be produced by hydrogenation of olefin B" produced from a 1,1-connection during the chain termination process. The presence of component B is unexpected from this type of chemistry.

Figure 5:
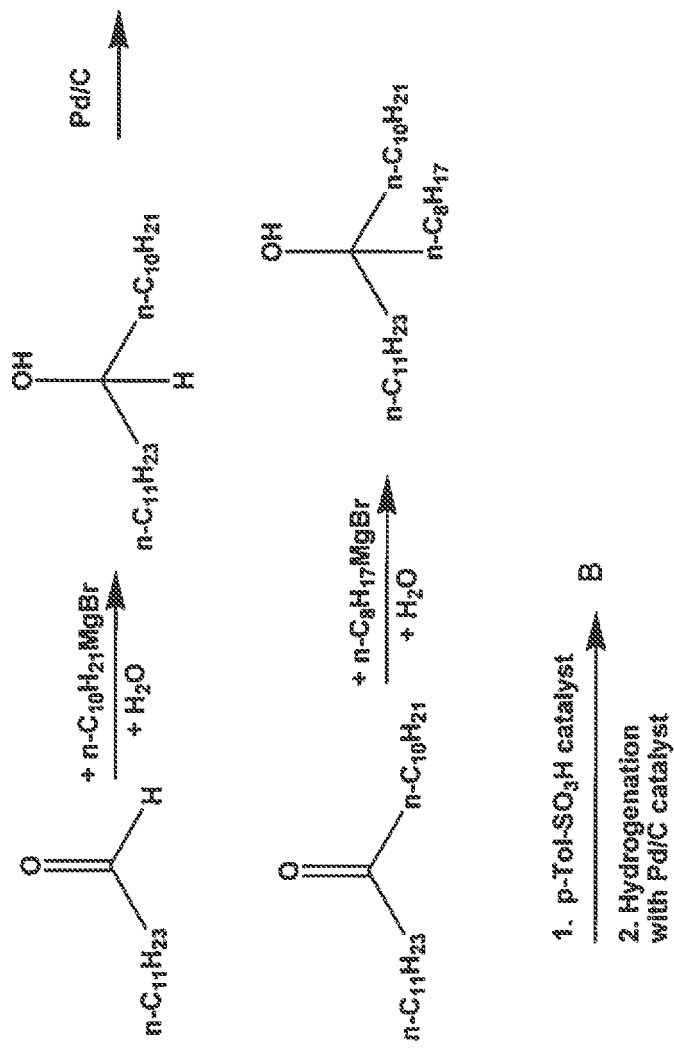
FIG. 5 is a possible reaction scheme for the independent synthesis of C30H62B.

The amount of Component B, 1,1-octyldocosane, is related to product viscosity, as demonstrated in Table 4. In Table 4, the higher the lube viscosity, the higher the amount of component B is in the 1-decene-trimer fraction. This is quite unexpected from previously known chemistry. The presence of B is beneficial for fluid property. For example, a $C_{30}H_{62}B$ compound, synthesized independently from n-dodecyl aldehyde following a well-defined chemical reaction path as shown in FIG. 5 (final product B $C_{30}H_{62}$, 11-octyldocosane), has superior viscometrics and VI (Kv at 100° C.=3.38 cSt, VI=149), as compared to the current low vis PAO of Kv at 100° C.=4.1 cSt and VI=126 or the synthesized $C_{30}$ A with Kv at 100° C. of 3.67 and VI=130.

TABLE 4 lube properties and amount of compound B in C30 component

| | Example no | | | | | |
|---|---|---|---|---|---|---|
| | 27 | 28 | 29 | 30 | 31 | 32 |
| catalyst type | A | B | I | F | F | F |
| Reaction temp., ° C. | 50 | 100 | 70 | 126 | 100 | 70 |
| Lube properties | | | | | | |
| KV100° C., cSt | 8.14 | 10.29 | 13.81 | 15.86 | 37.56 | 126.27 |
| KV40° C., cSt | 43.8 | 56.73 | 85.04 | 100.57 | 284.04 | 1132.63 |
| Viscosity Index | 162 | 172 | 167 | 169 | 183 | 218 |
| pour point, ° C. | <−55 | <−50 | <−52 | <−55 | −48 | −33 |
| Bromine number before hydrogenation | 27.0 | 21.5 | 20.2 | 17.5 | 11.1 | 5.6 |
| Bromine number after hydrogenation | 0 | 0 | 0 | 0.5 | 0 | 0 |
| Wt % B component in $C_{30}H_{62}$ fraction | 3.6 | 4.9 | 4.9 | 8.4 | 11.3 | 14.6 |

Figure 6:
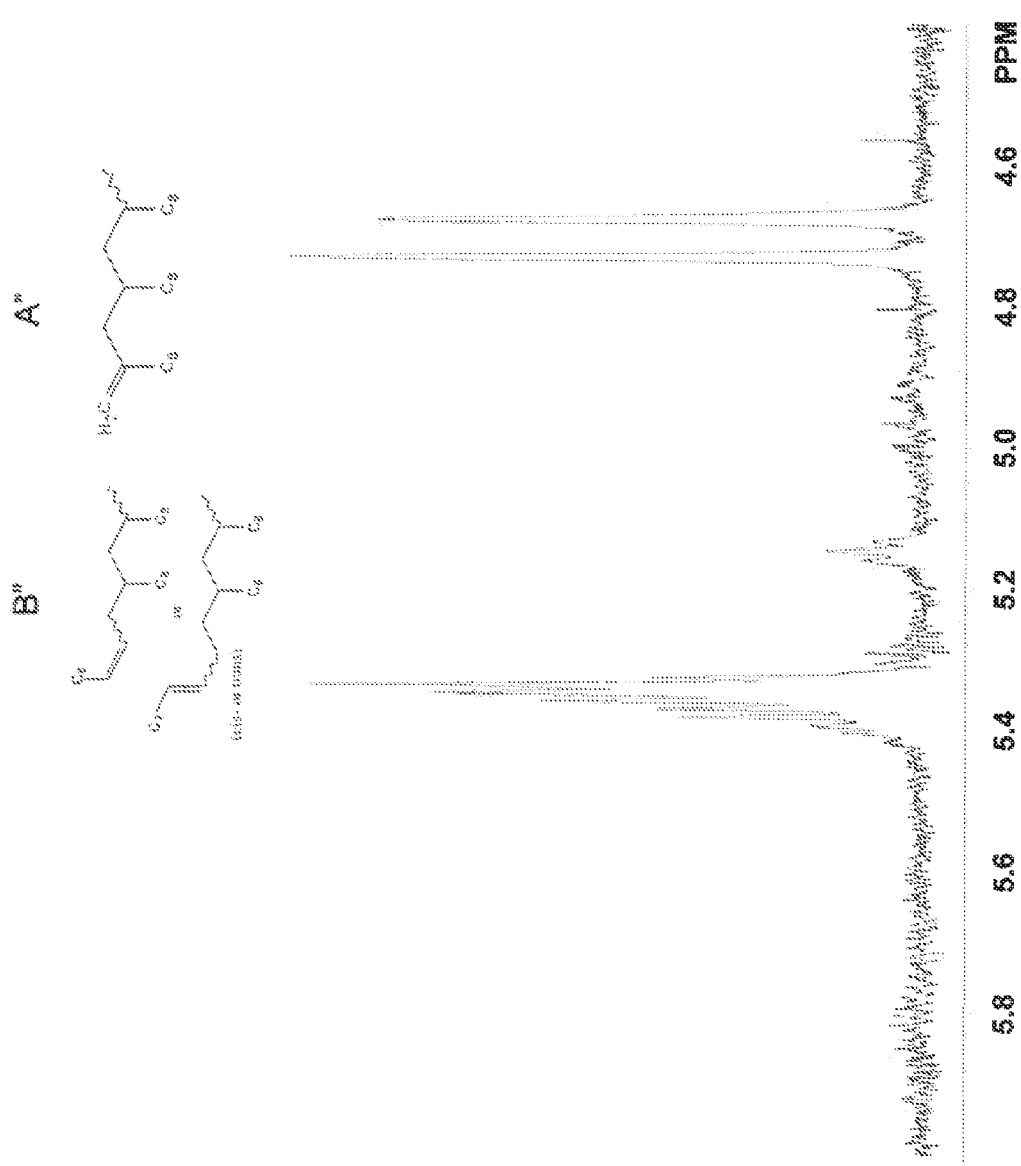
FIG. 6 is a proton-NMR of the olefinic region of the Example 35 PAO.

Catalsyt type:
A biscyclopentadienylzirconium dichloride
B dimethylsilylbis(cyclopentadienyl)zirconium dichloride
I bis(ethylcyclopentadienyl)zirconium dichloride
F rac-dimethylsilylbis(tetrahydroindenyl)zirconium dichloride For high viscosity fluids, the quantitative presence of the 1,1-connection can be determined by the proton NMR of the olefinic region before hydrogenation. The olefinic carbons in component A" and B" have very different chemical shifts (FIG. 6). In the olefinic region, each olefin class resonates in a characteristic region assigned according to the table below:

| Olefin type | Chemical shift range (ppm) | Number of protons |
|---|---|---|
| Vinyl | 5.7-5.9 | 1 |
|  | 4.8-5.3 | 2 |
| 1,2-disubstituted | 5.3-5.6 | 2 |
| Trisubstituted | 4.8-5.3 | 1 |
| Vinylidene (1,1-disubstituted) | 4.6-4.8 | 2 |

The total olefinic integral can be subdivided as described, and gives quantitative concentrations for each olefin type.

Examples 33 to 35. Three poly-1-decene samples were prepared using similar procedures as Example 31, except at different temperatures and the products were analyzed by proton NMR before hydrogenation. The olefin distribution was determined as described above, and a typical olefinic region of a proton NMR spectrum is shown in FIG. 6. From this proton NMR analysis, we calculated the mole % unhydrogenated B in total PAO product. After hydrogenation, the B" will be converted to B component. The B component varied with the product viscosities and higher viscosity fluid had higher amount of component B in the end group (Table 5).

TABLE 5

Amount of structure B" in poly-1-decene lube fluid by H-NMR

|  | Example no. | | |
|---|---|---|---|
|  | 33 | 34 | 35 |
| Catalyst | F | F | F |
| Reaction temp., ° C. | 100 | 70 | 45 |
| KV100° C., cSt | 35.13 | 150.39 | 497.01 |
| KV40° C., cSt | 254.27 | 1374.27 | 5174.28 |
| Viscosity Index | 187 | 224 | 278 |
| Pour point, ° C. | −44 | −30 | −22 |
| Bromine No. before hydrogenation | 11.1 | 4.8 | 2.3 |
| Mole % of component by H-NMR | | | |
| A" | 78.9 | 66.2 | 41.2 |
| B" | 15.9 | 30.0 | 53.9 |
| Others* | 5.2 | 3.8 | 4.9 |

The product made in Example 32 was evaluated for EHL (elastohydrodynamic lubrication) traction performance using a Mini-Traction Machine (MTM) from PCS Instruments Ltd. This device uses a ball-on-plate configuration in which each is driven independently in order to vary sliding and rolling speeds. Under the varied sliding and rolling speeds, an EHL contact is formed between the ball and plate thereby separating the surfaces. The separated surfaces allow the lubricant shear effects to be measured, while temperature and contact pressure are varied to produce a comprehensive map of the fluid's behavior. As referenced in FIG. 7, the traction coefficient is a ratio of the EHL traction force measured to the normal force applied (Ft/Fe). The results are presented in Table I.

TABLE I

|  | Pressure (GPa) | | |
|---|---|---|---|
|  | 0.75 | 1 | 1.25 |
| At 80° C. | | | |
| SpectraSyn 100 | 0.0151 | 0.0246 | 0.0308 |
| SpectraSyn Ultra 150 | 0.013 | 0.0227 | 0.0299 |

TABLE I-continued

|  | Pressure (GPa) | | |
|---|---|---|---|
|  | 0.75 | 1 | 1.25 |
| Hydrogenated Example 32 PAO at 100° C. | 0.0123 | 0.0222 | 0.0291 |
| SpectraSyn 100 | 0.0118 | 0.0201 | 0.0263 |
| SpectraSyn Ultra 150 | 0.0111 | 0.0191 | 0.0256 |
| Hydrogenated Example 32 PAO At 120° C. | 0.0106 | 0.0187 | 0.025 |
| SpectraSyn 100 | 0.0088 | 0.0149 | 0.0205 |
| SpectraSyn Ultra 150 | 0.0084 | 0.0143 | 0.02 |
| Hydrogenated Example 32 PAO | 0.0072 | 0.0129 | 0.0186 |

Figure 7:
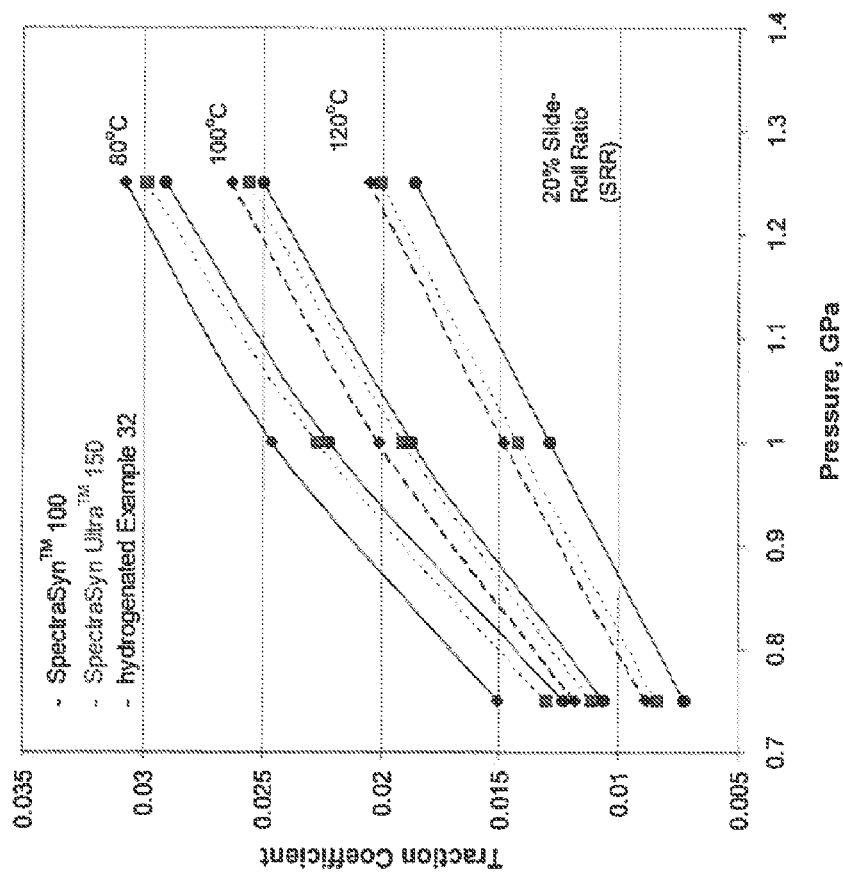
FIG. 7 is a graph of traction results for the Example 32 hydrogenated PAO compared to SpectraSyn 100 and SpectraSyn Ultra 150.

FIG. 7 compares the traction coefficients of conventional PAO with 100 cSt viscosity (at 100° C.), SpectraSyn™ 100, a SpectraSyn Ultra™ 150 and hydrogenated polyolefin of Example 32. As the data show, hydrogenated Example 32 lube has a consistently lower traction coefficient over a wide range of test pressure and temperature Lower traction coefficient is more desirable and is advantageous for energy efficiency (Reference—Synthetic Basics, Benefits of Synthetic Lubricants in Industrial Applications, W. R. Murphy, D. A. Blain, A. S. Galiano-Roth, J. Synthetic Lubrication, January 2002 (18) p. 301).

Examples 36 to 41. This set of experiments was carried out in a continuous reactor. These runs demonstrated the use of non-cordinating anion (NCA) as activiator, high lube yields and or narrow molecular weight distribution. 1-Decene and toluene used in the runs were purified through a 5 Angstrom molecular sieve. The metallocene catalyst used was dimethylsilylbis[tetrahydroindenyl]zircomium dimethyl. The activator used was N,N-dimethylanilinium tetra(pentafluorophenyl)borate (labled as activator-A or NCA-A). A catalyst solution was prepared by pre-mixing equal molar of metallocene with the activator in toluene solution to give 0.8 micromole catalyst per ml of solution. The experiments were conducted in a series dual-reactor continuous solution process. Both of the reactors were 1-liter autoclave reactors. All feeds were introduced into the first reactor. Both of the reactors were controlled at the same reaction temperature. The catalyst solution of 0.8 micromole/ml, a scanveger tri-n-octylaluminum (TNOA) solution, and purified 1-decene were continuously pumped into an one-liter stainless autoclave heated to reaction temperature. Reaction product was continuously withdrawn from the autoclave, quenched, and washed with water. The organic layer was further distilled at high temperature to remove any C20 and lighter components. These data demonstrated that the NCA activator gave excellent catalyst productivities, conversions and or lube yields. The residual oil was then hydrogenated using 1 wt % Ni-on-Kieselguhr catalyst at 200° C., 800 psi (5.5 MPa) hydrogen pressure for 4 hours. The bromine numbers for all samples after hydrogenation were much below 1. The reaction conditions and the hydrogenated finished lube properties are summarized in the following Table 6. This set of data demonstrates that a wide range of viscosities can be produced at high productivities. Also, these data show that a wide range of mm contents, ranging from 86% to 51%, can be produced.

Carbon-13 NMR was used to determine the tacticity of the polyalphaolefins of the present invention. Carbon-13 NMR can determine the presence and quantity of triads present, denoted mm (meso, meson, mr (meso, racemic) and rr (racemic, racemic). Extensive runs of mm or rr triads correspond to isotactic and syndiotactic polyalphaolefins, respectively. The tacticity of the polydecene was examined by carbon-13

Figure 3:
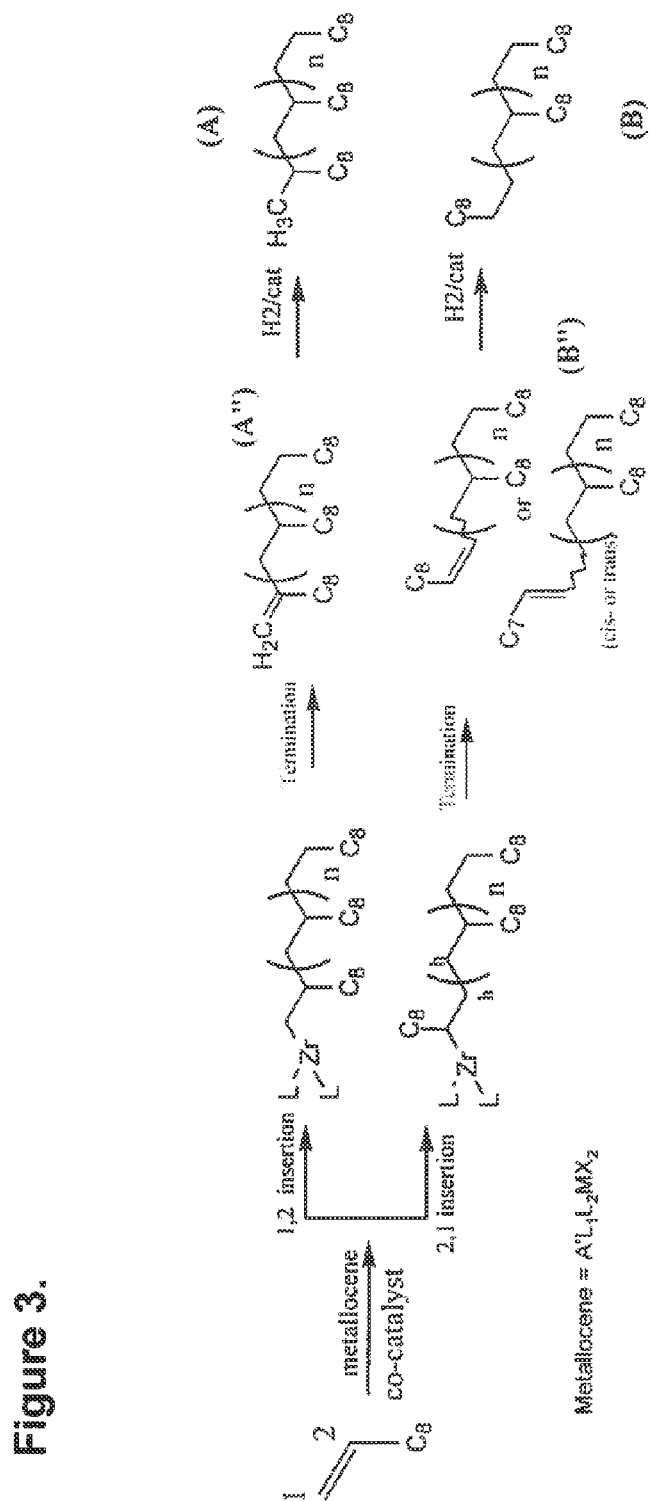
FIG. 3 is a possible reaction scheme for the formation of A", B", A and B components, including head to head connection.
Figure 8:
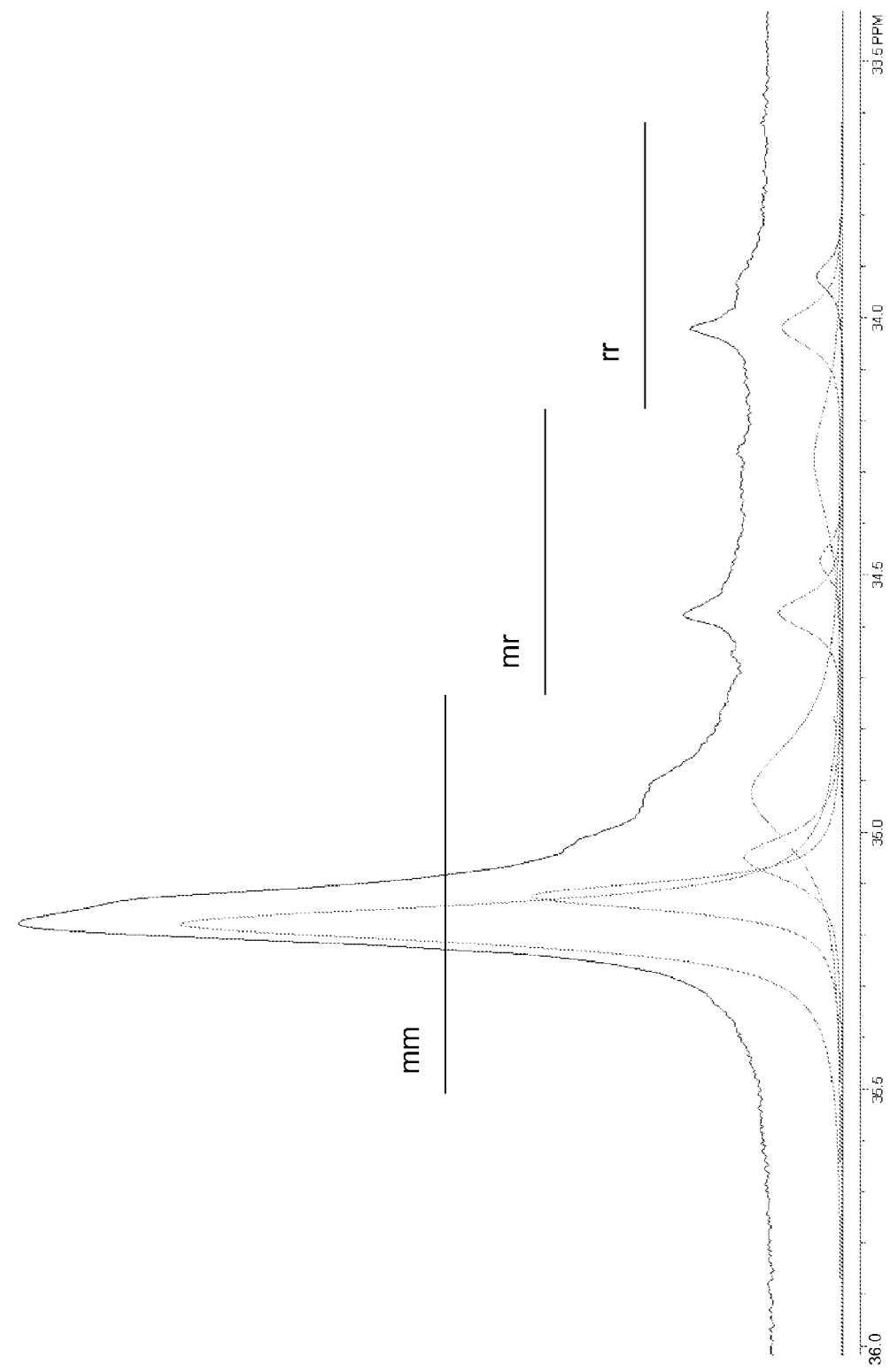
FIG. 8 is a carbon 13 NMRs pectra of $8B_8$ region of Example 36.

NMR. Spectra for these samples were acquired in the following manner. The polymer samples were dissolved in chloroform-d for carbon analysis. Approximately 10-15 mg/ml of chromium acetylacetonate relaxation agent, $Cr(acac)_3$, was added to the carbon samples to enhance the data acquisition rate. Spectra were acquired using the 10 mm broadband probe on either the Varian INOVA 300 or the Varian UnityPlus 500, with 8000-12000 scans acquired for each spectrum. Three carbon chemical shifts in polydecene and polydodecene evidence tacticity dependence: the $S_{\alpha\alpha}$ backbone methylene, and the $8B_8$ and $7B_8$ methylenes (for decene) and the $10B_{10}$ and $9B_{10}$ methylenes (for dodecene) on the short chain branches (SCBs). A peak deconvolution was performed on the $8B_8$ or $10B_{10}$ peaks, and assigned to monomer stereochemical triads according to the paper by I. Kim, J.-M. Zhou, and H. Chung, *Journal of polymer Science: Part A: Polymer Chemistry* 38 (2000) 1687-1697. FIG. 3 in the paper by Kim, et al. shows how the chemical shift offset of the relevant branch methylene varies with branch length. Based on the trends shown, we assumed that the dodecene- and decene-based SCBs were both of sufficient length that the chemical shift assignments for the $8B_8$ and $10B_{10}$ methylenes would be interchangeable. It also follows from this figure, that copolymers of different alphaolefins will have spectra complicated by monomer sequence effects. Furthermore, several of the samples are low $M_n$ materials, and contributions from chain end carbons overlap the region of interest. Where possible, the end group resonances were identified, integrated. Their contribution to the peaks were removed from the analysis. The deconvolutions were executed with Acorn NMR Inc.'s NutsPro NMR data analysis software, using an 85/15 Lorentzian/Gaussian lineshape. The component peaks were lumped together into clusters according to the mm (~34.65-35.4 ppm), mr (~34.2-34.65 ppm), and rr (33.8-34.2 ppm) triad assignments, and fit by least-squares minimization to a Bernoullian distribution. The probability of racemic addition, $P_r$, is the adjustable parameter. The exact chemical shift offset cut points for the stereo triad regions may vary somewhat as a function of solvent type, temperature, sample concentration, and relaxation agent concentration. A typical spectrum of this region was shown in FIG. 8.

End group-related resonances appear in the 42-45 ppm and 35-36.5 ppm regions. Visual inspection of low-Mn materials suggests that there are three endgroup carbons contributing to the $8B_8$ or $10B_{10}$ region, with one carbon in each of the mm, mr, and rr triad regions. As a first-order approximation to end group correction, the end group resonances (where detected) in the 42-45 and 35-36.5 ppm regions were integrated by deconvolution. The integral values so obtained were averaged and subtracted from each of the mm, mr, and rr triad areas. In general, the quality of fit improves upon such correction. The carbon-13 data is reported in Table 6 and is reported in mole %.

Figure 9:
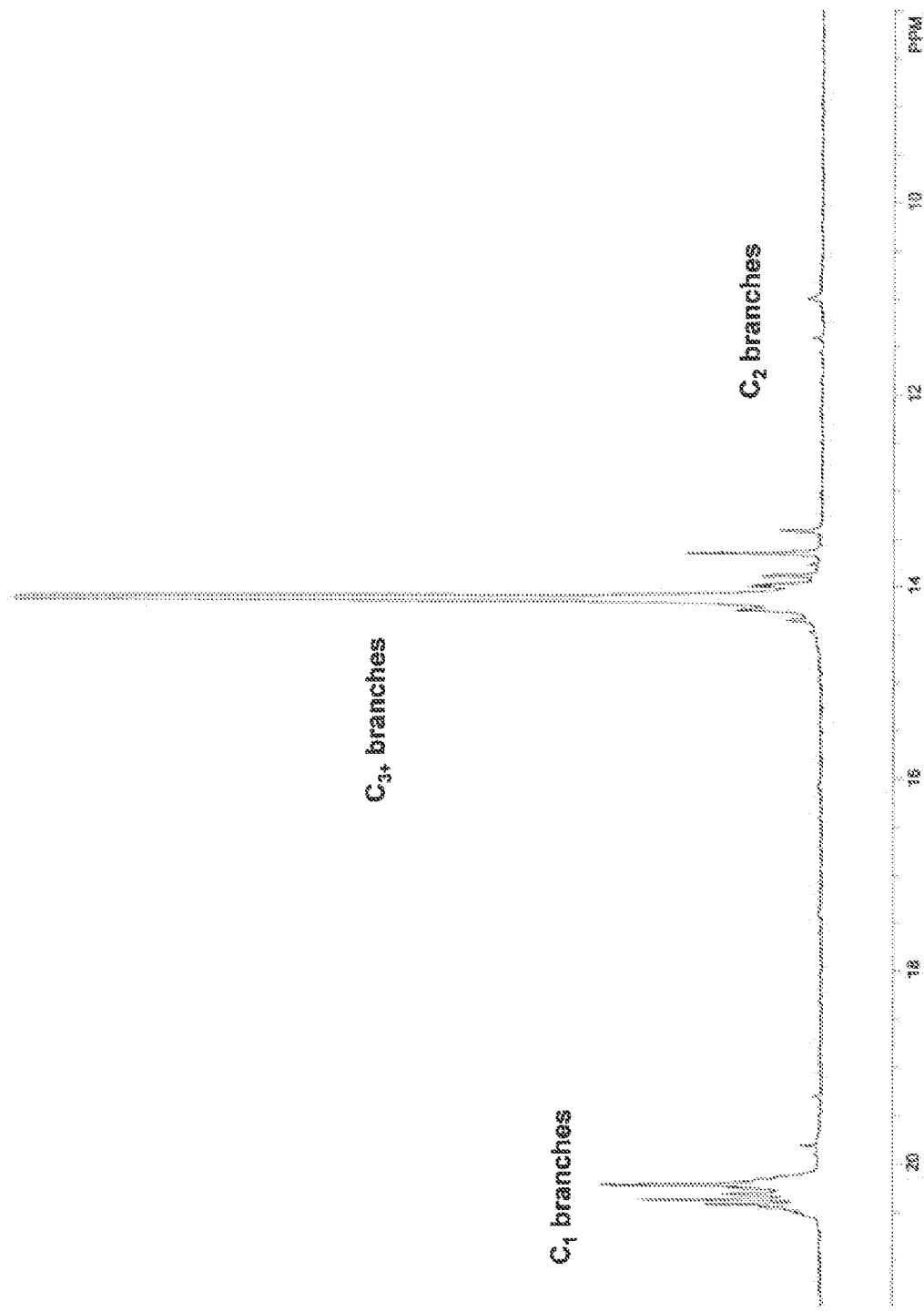
FIG. 9 is a methyl branch and $C_{3+}$ branch region of the carbon 13 NMR spectrum for Example 56.

Branch concentrations were also determined by NMR spectroscopy. The characteristic shift ranges for the carbon spectra are methyl branch: 20-15 ppm, propyl branch: 15-14.2 ppm, butyl and longer branches: 14.2-13 ppm, ethyl branches: 12-8 ppm. In the proton spectra, the methyl protons resonate upfield of 1 ppm, and signals from different branch lengths can often be resolved sufficiently to allow quantification by branch length. A typical spectrum of this region was shown in FIG. 9. In the carbon spectra, the integrals of the branch methyl signals can be divided by the total spectral integral, and the result expressed in terms of branches per 1000 carbons. The same holds true for the proton spectrum, although the integrals need to be corrected for the proton multiplicity of the relevant carbon (e.g. $CH$, $CH_2$, or $CH_3$). FIG. 9 shows the methyl region of a decene carbon spectrum.

TABLE 6

| | Reaction Conditions for Ex 36 to 41 | | | | | |
|---|---|---|---|---|---|---|
| | Ex. No | | | | | |
| | 36 | 37 | 38 | 39 | 40 | 41 |
| Rxr Tem. (° C.) | 50 | 60 | 70 | 80 | 90 | 100 |
| 1-decene (ml/min) | 40 | 40 | 40 | 40 | 40 | 40 |
| Cat rate (mol/min) | 2.39E−06 | 2.39E−06 | 3.73E−06 | 3.73E−06 | 3.73E−06 | 3.73E−06 |
| TNOA (mol/min) | 7.57E−10 | 7.57E−10 | 9.10E−10 | 9.10E−10 | 9.10E−10 | 9.10E−10 |
| Yield (g/min) | 21.9 | 24.14 | 25.43 | 28.04 | 29.19 | na |
| Conversion, wt % | 73.27 | 80.76 | 85.08 | 93.84 | 97.67 | na |
| Productivity g-lube/g cat. | 2.19E+04 | 2.41E+04 | 1.63E+04 | 1.80E+04 | 1.87E+04 | na |
| KV at 100° C., cSt | 295.21 | 169.07 | 79.49 | 26.54 | 14.89 | 11.2 |
| KV at 40° C., cSt | 3002.3 | 1618 | 696.8 | 197.2 | 99.7 | 70.4 |
| Viscosity Index | 249 | 225 | 197 | 169 | 155 | 150 |
| Pour point, ° C. | −30 | −30 | −33 | −48 | −52 | −57 |
| Bromine number after hydrogenation | 0.09 | 0.05 | 0.00 | 0.00 | 0.05 | 0.22 |
| Mw | 10732 | 7579 | 4823 | 2586 | 1760 | 1493 |
| Mw/Mn | 1.758 | 1.671 | 1.516 | 1.317 | 1.161 | 1.14 |
| Tacticity by C13 NMR, in mole % | | | | | | |
| mm | 86 | 86 | 76 | 69 | 62 | 51 |
| mr | 13 | 14 | 22 | 28 | 33 | 41 |
| rr | 1 | 0.1 | 2 | 3 | 1 | 8 |
| Pr | 0.07 | 0.07 | 0.13 | 0.17 | 0.21 | 0.29 |
| Ratio of mm/mr | 6.6 | 6.1 | 3.5 | 2.5 | 1.9 | 1.2 |
| CH3 per 1000 Carbons Measured by C13-NMR | | | | | | |
| | 1.9 | 2.7 | 3.9 | 8.1 | 13.0 | 16.2 |

The Example 36 and Example 37 products were subjected to a tapered roller bearing shear test (CEC L-45-T/C), a severe viscosity shear stability test, for 20 hours. At the end of the test, the Example 36 fluid lost only 0.77% of its original viscosity. The Example 37 fluid lost −0.20% of its original viscosity. This viscosity change is well within the experimental error of viscosity measurement. Such outstanding shear is not known for other fluids of similar viscosity range. This property can be significant for many high performance application, such as in the formulation of automotive engine, industrial, gear oils and grease formulation, etc.

Example 42 demonstrates the use of the dihalide form of a metallocene catalyst with an NCA activator. The metallocene used was catalyst F. A reaction flask containing 50 gram purified 1-decene and 31.74 mg tri-siobutylaluminum (TIBA) was heated to 30° C. To this flask a catalyst solution containing 0.912 mg F catalyst and 0.801 mg activator-A in 20 ml toluene was added. After 20 hours of reaction at this temperature, 2 ml isopropanol was added. The reaction mixture was worked up by water wash. The product was distilled at 160° C./1 mm-Hg vacuum to remove any light ends. The residual lube oil properties are summarized in Table 7. Examples 43 to 46 are similar to Example 42 except at different reaction temperature. Example 47 is similar to Examples 42, except catalyst I was the metallocene used.

TABLE 7

1-Decene polymerization by metallocene and NCA activator-A

| | Example No. | | | | | |
|---|---|---|---|---|---|---|
| | 42 | 43 | 44 | 45 | 46 | 47 |
| Reaction Temp, C. | 30-40 | 30-65 | 70 | 120 | 140 | 70 |
| Solution weight in reactor | | | | | | |
| 1-decene, grams | 50 | 50 | 50 | 50 | 50 | 50 |
| TIBA, mg | 31.74 | 63.6 | 63.6 | 63.6 | 63.6 | 63.6 |
| Toluene, grams | 0 | 0 | 20 | 20 | 20 | 20 |
| Metallocene, mg | 0.912 | 0.912 | 0.954 | 0.918 | 0.912 | 0.697 |
| NCA-A activator, mg | 0.801 | 3.205 | 3.205 | 3.205 | 3.205 | 3.205 |
| wt % Selectivity to Lube | 95.7 | 97.0 | 96.2 | 80.6 | 73.0 | 94.0 |
| KV at 100° C., cSt | 1095.2 | 194.61 | 72.53 | 8.43 | 6.2 | 40.08 |
| Viscosity Index | 310 | 226 | 191 | 151 | 145 | 167 |
| Pour Point, ° C. | | −28 | −38 | <−56 | | |
| Mw | 25151 | 9094 | 4718 | 1358 | | |
| Mw/Mn | 2.05 | 2.04 | 1.62 | 1.22 | | |

These Examples 42 to 46 demonstrate that high quality lube can be produced in high yields. The lubes have high VI and very narrow Mw/Mn. Also, high selectivity to lube can be obtained with these catalysts.

For Example 48 and 49 in Table 8, the metallocene was catalyst F. For Example 50 in Table 8 the metallocene was catalyst I.

TABLE 8

1-Decene reaction over metallocene and activator-B as activator

| | Example No. | | |
|---|---|---|---|
| | 48 | 49 | 50 |
| Reaction Temp, C. | 70 | 140 | 70 |
| Solution weight in reactor | | | |
| 1-decene, grams | 50 | 50 | 50 |
| TIBA, mg | 65 | 65 | 65 |

TABLE 8-continued

1-Decene reaction over metallocene and activator-B as activator

| | Example No. | | |
|---|---|---|---|
| | 48 | 49 | 50 |
| Toluene, grams | 20 | 20 | 20 |
| Metallocene, mg | 0.456 | 0.456 | 0.348 |
| NCA activator, mg | 0.922 | 0.922 | 0.922 |
| wt % Selectivity to Lube | 99.4 | 69.1 | 93.6 |
| Kinematic Viscosity at 100° C., cSt | 83.71 | 6.76 | 39.03 |
| Viscosity Index | 194 | 162 | 170 |

Examples 51 to 63 in Table 9 demonstrate that other metallocene catalysts activated with MAO or NCA activators can produce high quality fluids in high yields. The procedures for these examples were similar to Examples 27 to 32 when MAO was the activator or similar to Example 42 when NCA was used as activator. [Note—these samples were not hydrogenated.] Examples 51 to 56 demonstrate that a wide range of catalysts can be used to produce polymers with high degree of mm triads. These catalysts include the racemic catalysts including Catalysts F, E, and T; and highly substituted catalyst U. Examples 59 to 62 demonstrate that using meso type catalysts with no hydrogen produces fluids with lower degree of mm triads (e.g. less than 40%) and bromine number of up to 6 before hydrogenation. This is unexpected when compared to U.S. Pat. No. 6,706,828.

TABLE 9

Polymer fluids from 1-decene by different metallocene catalysts -
reaction conditions, results, product properties and tacticity analysis.

| Ex. no. | Catalyst* | Reaction temp. ° C. | % Selectivity to lube | KV@ 100° C., cS | VI | Pour point, ° C. | Br. No**. | Mole % analyzed by C13-NMR | | | | mm/mr ratio |
|---|---|---|---|---|---|---|---|---|---|---|---|---|
| | | | | | | | | mm | mr | rr | Pr | |
| 51 | F | 50 | 96 | 295.2 | 249 | −30 | 2.8 | 87 | 5 | 9 | 0.05 | 17.4 |
| 52 | E | 50 | 100 | 1028.96 | 306 | −19 | 0.8 | 98 | 2 | 0 | 0.01 | |
| 53 | E | 75 | 94 | 368.05 | 252 | na | 0.5 | 83 | 16 | 1 | 0.09 | |
| 54 | E | 100 | 74 | 92.61 | 200 | −39 | 4.3 | 65 | 31 | 4 | 0.2 | |
| 55 | E | 125 | 48 | 41.94 | 187 | −50 | 10.5 | 64 | 32 | 4 | 0.2 | |
| 56 | M | 70 | 95 | 32.05 | 170 | na | 10.2 | 42 | 46 | 13 | 0.36 | |
| 57 | T | 70 | 88 | 3044.88 | 165 | na | na | 88 | 12 | 4 | 0.06 | |
| 58 | U | 70 | 99 | 101.67 | 193 | −38 | 3.9 | 31 | 49 | 2 | 0.44 | 15.6 |
| 59 | V | 70 | 99 | 2339.93 | 354 | na | na | 34 | 49 | 17 | 0.41 | |
| 60 | W*** | 50 | 99 | 3758.42 | 380 | na | na | 34 | 49 | 17 | 0.41 | |
| 61 | W | 50 | 99 | 1383.62 | 323 | −27 | na | 34 | 49 | 17 | 0.42 | |
| 62 | W | 70 | 98 | 861.34 | 296 | −30 | na | 33 | 49 | 18 | 0.43 | |
| 63 | W | 125 | 76 | 117.72 | 206 | −41 | 5.7 | 34 | 49 | 17 | 0.42 | |

*Catalyst type
T Rac-dimethylsilylbis(2-methylindenyl)ZrCl2
U Bis(tetramethylcyclopentadienyl)ZrCl2
V meso-dimethylsilylbis(2-methylindenyl)ZrCl2
W meso-ethylenebis(indenyl)ZrCl2
**The samples in this Table were not hydrogenated and the Bromine numbers were measured before hydrogenation.
***NCA activator A was used.

Examples 64 to 69 demonstrate the advantages of hydrogenation of the polyalpha-olefins produced from the polymerization step. In this hydrogenation reaction, the Example 52 polyalpha-olefin was charged into an autoclave together with 3 wt % of a Ni (~60%) on Kieselguhr hydrogenation catalyst, purged with hydrogen to remove air and pressurized with hydrogen to 800 psi (5.5 MPa) and heated to 250° C. with agitation. The sample was allowed to hydrogenated for different period of reaction time. All the hydrogenated samples have bromine number less than 0.5. Other properties of the fluids are summarized in Table 10. These data demonstrate that post-polymerization hydrogenation not only reduces the bromine number to below 1, but also we can produce polyalpha-olefins with 26 to 95 mole % of mm triads. Furthermore, comparing the DSC of the hydrogenated samples versus the unhydrogenated sample, the hydrogenated samples had reduced heat of melting (ΔHm, j/g) and heat of crystallization (ΔHc, j/g). Hydrogenation of the sample can reduce the heat of melting and crystallization as shown in Table 10.

TABLE 10

| | Example No. | | | | | | |
|---|---|---|---|---|---|---|---|
| | 52 | 64 | 65 | 66 | 67 | 68 | 69 |
| time, hrs | Starting PAO | 1 | 2 | 4 | 7 | 12 | 24 |
| Mole % diads by C13-NMR | | | | | | | |
| mm | 98 | 95 | 72 | 57 | 45 | 36 | 26 |
| mr | 2 | 3 | 15 | 20 | 41 | 38 | 47 |
| rr | 0 | 3 | 13 | 22 | 14 | 27 | 26 |
| Pr | 0.01 | 0.02 | 0.13 | 0.21 | 0.33 | 0.43 | 0.5 |
| Mole % mm change | 0 | 3 | 26 | 41 | 53 | 62 | 72 |
| DSC | | | | | | | |
| ΔHm, j/g | 25.01 | 22.69 | 21.58 | 13.98 | 2.051 | 0 | 0 |
| ΔHc, j/g | 19.94 | 21.38 | 15.68 | 18.13 | 1.683 | 0 | 0 |
| % Hm decrease | 0.0 | 9.3 | 13.7 | 44.1 | 91.8 | 100 | 100 |

DSC (Differential scanning calorimetry) was measured using a Perkin Elmer DSC. 10 mg samples was heated at 10° C./minutes to 150° C. and then cooled down to −100° C. at 10° C. per minute. The total heat of melting and crystallization during cooling was measured by integrating the heat corresponding to the melting and crystallization peak using the standard software provided by Perkin Elmer.

Example 70 to 74 were carried out similarly to Ex. 31, except 1-hexene was used in each experiment. The amounts of catalyst and activators used, together with product properties are summarized in Table 11. This set of examples demonstrated that other alpha-olefins can be used to produce high quality fluids.

TABLE 11

| | Example | | | | |
|---|---|---|---|---|---|
| | 70 | 71 | 72 | 73 | 74 |
| temperature, ° C. | 45 | 70 | 100 | 125 | 170 |
| reaction time, hr | 22 | 20 | 21 | 21 | 24 |
| grams hexene feed | 91 | 90 | 90 | 90 | 90 |
| grams of MAO solution | 0.117 | 0.0585 | 0.0585 | 0.0585 | 0.0585 |

TABLE 11-continued

| | Example | | | | |
|---|---|---|---|---|---|
| | 70 | 71 | 72 | 73 | 74 |
| molar ratio Al/Zr | 300 | 250 | 250 | 250 | 250 |
| KV100° C., cSt | 1535.53 | 564.63 | 75.09 | 24.3 | 8.64 |
| KV40° C., cSt | 42368.3 | 12822.88 | 1086.46 | 253.28 | 59.27 |
| Viscosity Index | 239 | 198 | 132 | 112 | 108 |
| pour point, ° C. | | | | | |
| Wt % Conversion | 93 | 92 | 88 | 87 | na |

Examples 75 to 78 in Table 12 are similar to Example 42 to 46, except 1-hexene was used as starting material. These experiments demonstrated that 1-hexene can be polymerized into high quality fluids using metallocene and NCA activators and trialkylaluminum compounds as co-activator.

| | Example | | | |
|---|---|---|---|---|
| | 75 | 76 | 77 | 78 |
| Reaction Temperature, ° C. | 31 | 80 | 100 | 120 |
| Conversion, wt % | 89.4 | 93.5 | 86.5 | 49.1 |
| Lube Properties | | | | |
| KV100° C., cSt | 269.21 | 53.57 | 25.78 | 12.02 |
| KV40° C., cSt | 4900.26 | 661.38 | 269.58 | 96.66 |
| Viscosity Index | 176 | 132 | 115 | 105 |
| Pour Point, ° C. | −24 | −40 | −32 | −43 |
| Mn | 2519 | 1613 | 1211 | 912 |
| Mw/Mn | 3.025 | 1.667 | 1.315 | 1.287 |
| Mole % Olefin Types in Unhydrogenated Polyalpha-Olefins | | | | |
| Vinyledene | 67.4 | 71.4 | 72.3 | 72.2 |
| 1,2-disubstituted | 15.7 | 11.6 | 8.8 | 5 |
| tri-substituted | 16.9 | 17 | 18.9 | 22.8 |
| vinyl | 0 | 0 | 0 | 0 |

Using catalyst E (rac-ethylenebis(indenyl) ZrCl2) at different reaction temperature and similar reaction procedures, we obtained products with useful 100° C. viscosities ranging from 42 cSt to 1029 cSt (Examples 79 to 82 of Table 13) without any hydrogen.

TABLE 13

| Example no | Reaction Temp., ° C. | Kv@ 100° C., cS | Kv@ 40° C., cS | VI | Pour point, ° C. | mm | mr | rr | Pr |
|---|---|---|---|---|---|---|---|---|---|
| 79 | 50 | 1028.96 | 12399 | 306 | −19 | 0.98 | 0.02 | 0 | 0.01 |
| 80 | 75 | 368.05 | 4009.3 | 252 | na | 0.83 | 0.16 | 0.01 | 0.09 |
| 81 | 100 | 92.61 | 842.29 | 200 | −39 | 0.65 | 0.31 | 0.04 | 0.2 |
| 82 | 125 | 41.94 | 316.73 | 187 | −50 | 0.64 | 0.32 | 0.04 | 0.2 |

The product composition produced in this invention is different from the compositions produced in U.S. Pat. No. 6,706,828 and WO 02/14384. Our invention using metallocene catalysts with MAO or NCA activator optionally with co-activators in low or no hydrogen (usually less than 200 psi hydrogen preferably less than 50 psi or no hydrogen) during the polymerization step. In contrast, U.S. Pat. No. 6,706,828 and WO 02/14384 produced products from meso catalysts in the presence of hydrogen, as reported in Example D of U.S. Pat. No. 6,706,828 or Example J and K in WO 021484. FIG. 1 compares the bromine number of polymers produced in our invention vs Examples 1, 2, 8, 9, 10, 11, and 12 of U.S. Pat. No. 6,706,828.

In Comparative example 1, the reaction was conducted in the presence of 200 psi hydrogen and catalyst T (rac-dimethylsilylbis(2-methyl-1-lindenyl)zirconium dichloride, similar to Example D of U.S. Pat. No. 6,706,828. The results are summarized in Table 12. The polyalpha-olefin sample was analyzed for the Z mole % of B components in C30 fraction. The amount of this Z mole % was plotted in FIG. 2.

Comparative Examples 2 and 3 were similar to Comparative Example 1, except the reaction hydrogen pressure was 100 and 50 psi. The polyalpha-olefin sample was then analyzed for the mole % of B components in C30 fraction. Comparative Example 4 was similar to Comparative Example 1, except the reaction was carried out at 110° C.

TABLE 12

| Comparative Examples using rac-dimethylsilyl-bis(2-methylindenyl)zirconiumdichloride | | | | |
|---|---|---|---|---|
| | Comparative Example 1 | Comparative Example 2 | Comparative Example 3 | Comparative Example 4 |
| Temperature, ° C. | 100 | 100 | 100 | 110 |
| Hydrogen pressure, psi | 200 | 100 | 50 | 200 |
| KV@100 C., cSt | 89.5 | 466.2 | 598.01 | 59.10 |
| % B in C30 fraction | 5.7 | 4.3 | 2.2 | 7.5 |
| CH3 per 1000 C by C13 NMR | 14.2 | 2.7 | 2.5 | na |

TABLE 12-continued

| Comparative Examples using rac-dimethylsilyl-bis(2-methylindenyl)zirconiumdichloride | | | | |
|---|---|---|---|---|
| | Comparative Example 1 | Comparative Example 2 | Comparative Example 3 | Comparative Example 4 |
| Viscosity Index | 194 | 266 | 281 | |
| Pour Point, ° C. | −36 | −21 | −21 | |

Figure 2:
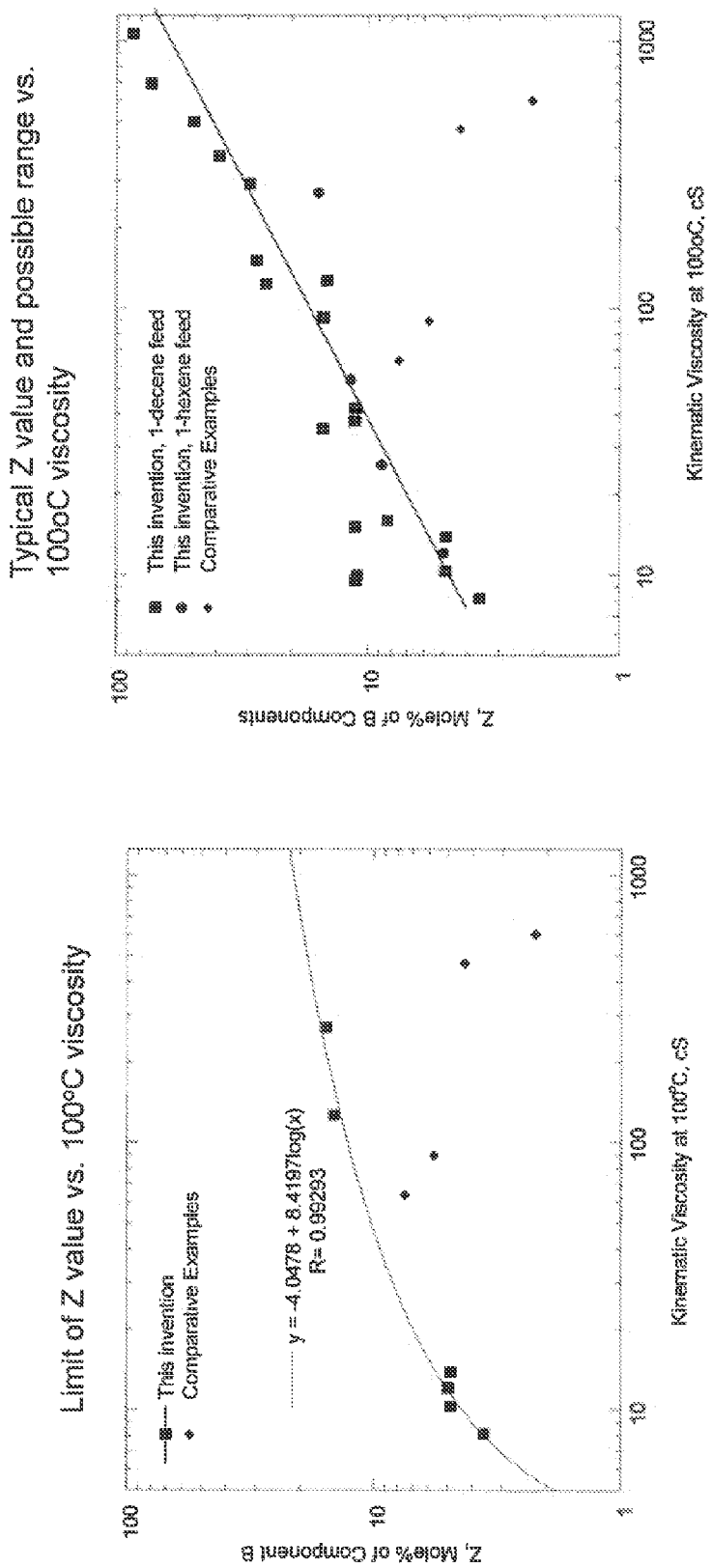
FIG. 2 is a graph of mole % B components (by GC or Proton NMR) versus KV100 for certain PAO's from the examples and comparative examples 1-4.

The amount of B mole % for the Comparative Examples 1-4 versus the amount of B mole % by Examples 27 to 35 is plotted in FIG. 2.

Figure 10:
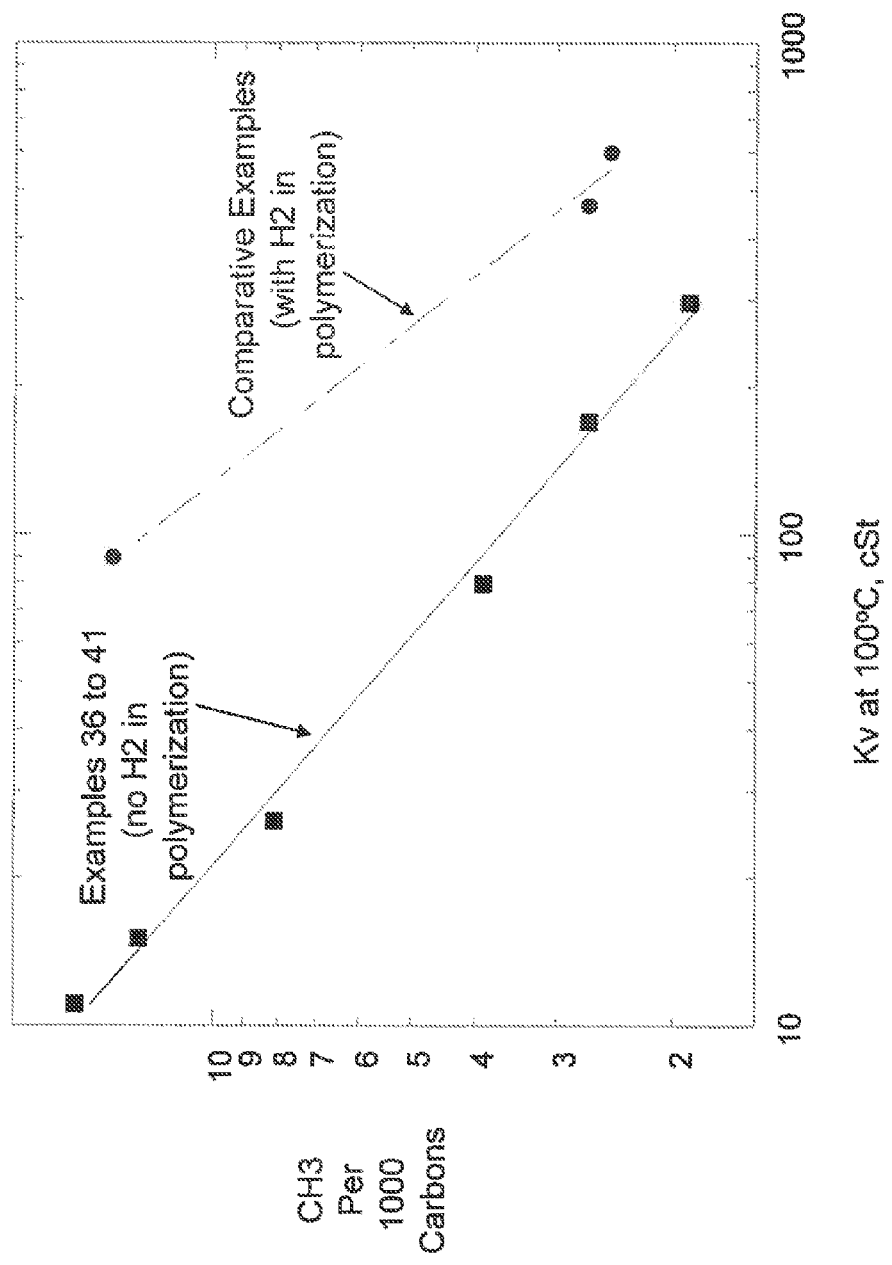
FIG. 10 is a graph of methyls per 1000 carbons versus KV100 for Examples 36, 37; 38, 39, 40, 41 and Comparative examples 1 to 4

Also, the amount of isolated $CH_3$ attached to a tertiary CH was analyzed by Carbon 13 NMR method and are summarized in Table 12. FIG. 10 compares the amount of $CH_3$ per 1000 Carbons of the Comparative Examples 1 to 3 produced in the presence of hydrogen during polymerization to the $CH_3$ per 1000 Carbons of Examples 36 to 41 produced without hydrogen during polymerization. This graph clearly shows that the compositions of Examples 36 to 41 have much lower methyl groups per 1000 Carbons. A lower amount of methyl groups is advantageous to the lube properties, as we have shown earlier that the trimer C30H62 without extra methyl group (Compound B) has better viscometrics, especially VI, than trimers in current PAO which has extra short chain branches. Furthermore, less $CH_3$ branches imply less tertiary hydrogen in the hydrocarbon structure. This tertiary hydrogen is more susceptible toward oxidative degration. This implies that compositions with less $CH_3$ branches and less tertiary hydrogen are less susceptible to oxidative degradation.

Table 13 shows that the types of unsaturation from Comparative Example 4 are very different from the types of unsaturations produced from Example 33 or 76. In Comparative Example 4 which used 200 psi hydrogen, 52% of the unsaturated double bonds were tri-substituted olefins. In contrast, in Example 33 or 76, where no hydrogen was added to the reactor, only 10 to 17% of the unsaturation double bonds are tri-substituted olefins by either MAO or NCA as co-activator.

TABLE 13

Comparison of unsaturation types.

| | Comparative Example 4 | Example 33 | Example 76 |
|---|---|---|---|
| KV at 100° C., cSt | 59.10 | 35.1 | 53.57 |
| Mole % trisubstittued olefins | 52 | 10 | 17.0 |
| Mole % vinylidene | 41 | 71 | 71.4 |
| Mole % 1,2-disubstituted olefins | 7 | 19 | 11.6 |

In preferred embodiments, the polyalpha-olefins produced herein have higher bromine numbers, the amount of tri-substituted olefins are significantly lower than prior art, and/or the amount of vinylidene+1,2-disubstituted olefins are higher. In further preferred embodiments the PAO's produced herein have higher amounts of B" structures believed to be formed from head-to-head connection in the polymer product. 3. In further preferred embodiments the PAO's produced herein have high mole% of mm content (>40%). In further preferred embodiments the PAO's produced herein have higher mole% of B"formed by head—to—head connection. This is indicated by the higher C30-B component by GC or the un-expected higher mole% of the di-substituded olefins of the B"structure.

These structural differences for the polyalpha-olefins persist after hydrogenation step(s) to remove the double bond, as is usually practiced to further improve lube base stock property. After hydrogenation, the examples above had lower amount of isolated $CH_3$ per 1000 carbons in the polymers than the Comparative Examples, even when the same polymerization catalysts were used. In our examples, we preferred to hydrogenate the sample after the polymerization. During this hydrogenation step, a we can tailor the mole% of mm content in the polymer. By selection of hydrogenation condition, we can maintain the same mole% of mm content or we can reduce the mole% mm content to significantly below 40

Examples 90, 91 and 92 illustrate the presence of aminor amount of ethylene in the polymerization. The procedure, catalyst, activator, and reaction condition were the same as for Example 46, except that ethylene was present.

| | Ex. No. | | |
|---|---|---|---|
| | 90 | 91 | 92 |
| Polymerization temperature (° C.) | 80 | 80 | 80 |
| 1-decene feed rate (ml/min) | 40.00 | 40.00 | 40.00 |
| Ethylene feed rate (standard liter per minute) | 0.18 | 0.01 | 0.35 |
| Catalyst/activator combination feed rate (mol/min) | 3.73E−06 | 2.39E−06 | 2.39E−06 |
| TNOA feed rate (mol/min) | 9.10E−10 | 9.10E−10 | 9.10E−10 |
| Yield (g/min) | 29.5 | 29.0 | 30.5 |
| Conversion (%) | 98 | 97 | 100 |
| Productivity (g lube/g catalyst) | 1.89E+04 | 2.90E+04 | 3.05E+04 |
| Mn (kg/mol) | 1.15 | 1.52 | 1.57 |
| Mw (kg/mol) | 1.31 | 2.00 | 1.70 |
| Mw/Mn | 1.14 | 1.32 | 1.09 |
| Wt % C2 in feed | 3.63 | 0.21 | 6.87 |
| Kv at 100° C., cSt | 11.67 | 22.81 | 15.58 |
| Kv at 40° C., cSt | 69.94 | 150.44 | 101.19 |
| viscosity index | 151 | 166 | 153 |

All documents described herein are incorporated by reference herein, including any priority documents and/or testing procedures, except to the extent they are inconsistent with this specification. As is apparent from the foregoing general description and the specific embodiments, while forms of the invention have been illustrated and described, various modifications can be made without departing from the spirit and scope of the invention. Accordingly, if is not intended that the invention be limited thereby.

The invention claimed is:

1. A polyalpha-olefin comprising more than 50 mole % of one or more C5 to C24 oligomer units where the polyalpha-olefin has:
   a) 40 mole % or more of mm triads,
   b) a Bromine number of Y or greater, where Y is equal to $89.92*(V)^{-0.5863}$, where V is the Kinematic Viscosity of the polyalpha-olefin measured at 100° C. in cSt, and
   c) 1,2 disubstituted olefins present if Z is less than 7, then the range if Z or more, and if Z is more than 7, the range is 7 or more, where $Z=8.420*Log(V)-4.048$ and V is the kinematic viscosity of the polyalpha-olefin measured at 100 ° C. in cSt.

2. A polyalpha-olefin comprising more than 50 mole % of one or more C5 to C24 oligomer units where the polyalpha-olefin if Z is less than 7, then the range is Z or more, and if Z is more than 7, the range is 7 or more of units represented by the formula:

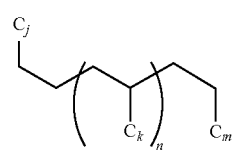

where j, k and m are each, independently, 3, 4, 5, 6, 7, 8, 9, 10, 11, 12, 13, 14, 15, 16, 17, 18, 19, 20, 21, or 22, n is an integer from 1 to 350, and where Z=8.420*Log(V)−4.048, where V is the kinematic viscosity of the polyalpha-olefin measured at 100° C. in cSt.

3. A polyalpha-olefin as set forth in claim 2 where the polyalpha-olefin has:
a) less than 40 mole % of mm triads, and
b) a Bromine number of 1.8 or less.

4. A polyalpha-olefin as set forth in claim 2 where the polyalpha-olefin has:
a) less than 40 mole % of mm triads, and
b) a Bromine number of Y or greater, where $Y=89.92 \times (V)^{-0.5363}$, where V is the kinematic viscosity in cSt measured at 100° C.

5. A polyalpha-olefin as set forth in claim 2, where the polyalpha-olefin has:
a) 40 mole % or more of mm triads, and
b) a Bromine number of 1.8 or less.

6. A polyalpha-olefin comprising more than 50 mole % of one or more C5 to C24 oligomer units where the polyalpha-olefin has 40 mole % or more of mm triads and less than 300 ppm of a Group 4 metal.

7. A polyalpha-olefin comprising more than 50 mole % of one or more C5 to C24 oligomer units where the polyalpha-olefin has 40 mole % or more of mm triads and less than 100 ppm of a Group 13 metal.

8. A polyalpha-olefin comprising more than 50 mole % of one or more C5 to C24 oligomer units where the polyalpha-olefin has 40 mole % or more of mm triads and less than 600 ppm of aluminum.

9. A polyalpha-olefin comprising more than 50 mole % C5 to C24 oligomer units and having an Mw of 100,000 or less and an Mw/Mn of greater than 1 and less than 2.5.

10. The polyalpha-olefin of claim 2 wherein the polyalpha-olefin is polydecene having an Mw/Mn of between 1 and 2.5.

11. The polyalpha-olefin of claim 2 wherein the polyalpha-olefin has a Bromine number of 1.8 or more.

12. The polyalpha-olefin of claim 2 wherein the polyalpha-olefin has an Mw/Mn of greater than 1 to 3.5.

13. The polyalpha-olefin of claim 2, wherein the polyalpha-olefin has an Mw/Mn of greater than 1 to 2.5.

14. The polyalpha-olefin of any of claim 2 wherein the polyalpha-olefin has a Kinematic viscosity at 100° C. of from 1.5 to 5000 cSt.

15. The polyalpha-olefin of claim 2 wherein the polyalpha-olefin has a Kinematic viscosity at 100° C. of from 2 to 3000 cSt.

16. The polyalpha-olefin of claim 2 wherein the polyalpha-olefin has a Kinematic viscosity at 100° C. of from 3 to 1000 cSt.

17. The polyalpha-olefin of claim 2 wherein the polyalpha-olefin has a Kinematic viscosity at 40° C. of from 4 to 100,000 cSt.

18. The polyalpha-olefin of any of claim 2 wherein the polyalpha-olefin has a Kinematic viscosity at 40° C. of from 6 to 50,000 cSt.

19. The polyalpha-olefin of claim 2 wherein the polyalpha-olefin has a Kinematic viscosity at 40° C. of from 10 to 30,000 cSt.

20. The polyalpha-olefin of claim 2 wherein the polyalpha-olefin has a Viscosity Index of 100 or more.

21. The polyalpha-olefin of claim 2 wherein the polyalpha-olefin has a Viscosity Index of 120 or more.

22. The polyalpha-olefin of claim 2 wherein the polyalpha-olefin has a Viscosity Index of 130 or more.

23. The polyalpha-olefin of claim 2 wherein the polyalpha-olefin has a Viscosity Index between 120 and 450.

24. The polyalpha-olefin of claim 2 wherein the polyalpha-olefin has a pour point of 0° C. or less.

25. The polyalpha-olefin of claim 2 wherein the polyalpha-olefin has a pour point of −30° C. or less.

26. The polyalpha-olefin of claim 2 wherein the polyalpha-olefin has a pour point between −10° C. and −80° C.

27. The polyalpha-olefin of claim 2 wherein the polyalpha-olefin has a pour point between −15° C. and −70° C.

28. The polyalpha-olefin of claim 2 wherein the polyalpha-olefin has a weight average molecular weight of 100,000 g/mol or less.

29. The polyalpha-olefin of claim 2 wherein the polyalpha-olefin has a weight average molecular weight of 100 to 100,000 g/mol.

30. The polyalpha-olefin of claim 2 wherein the polyalpha-olefin has a weight average molecular weight of 280 to 50,000 g/mol.

31. The polyalpha-olefin of claim 2 wherein the polyalpha-olefin has a weight average molecular weight of 336 to 40,000 g/mol.

32. The polyalpha-olefin of claim 5 wherein the polyalpha-olefin has a $KV_{100}$ of less than 200 cSt.

33. The polyalpha-olefin of claim 2 where the oligomer units having 5 to 24 carbon atoms are present at 55 mole % or more.

34. The polyalpha-olefin of claim 2 produced from a feed of one or more alpha-olefin monomers wherein the alpha-olefin monomer(s) are selected from the group consisting of 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 1-uneicosene, 1-docosene, 1-tricosene, 1-tetracosene, 1-pentacosene, 1-hexacosene, 4-methyl-1-pentene, 4-phenyl-1-butene, and 5-phenyl-1-pentene.

35. The polyalpha-olefin of claim 2 wherein the alpha-olefin monomer(s) are selected from the group consisting of 1-pentene, 1-hexene, 1-heptene, 1-octene, 1-nonene, 1-decene, 1-undecene, 1-dodecene, 1-tridecene, 1-tetradecene, 1-pentadecene and 1-hexadecene.

36. The polyalpha-olefin of claim 2 wherein the polyalpha-olefin monomer(s) are selected from the group consisting of 1-hexene, 1-octene, 1-decene, 1-dodecene, 1-tetradecene and 1-hexadecene.

37. The polyalpha-olefin of claim 2 wherein the polyalpha-olefin comprises octene, decene, and dodecene oligomer units.

38. The polyalpha-olefin of claim 2 wherein the polyalpha-olefin has a dielectric constant of 2.5 or less (1 kHz at 23° C.).

39. The polyalpha-olefin of claim 2 wherein the polyalpha-olefin has:
a) a kinematic viscosity of from 3 to 3000 cSt at 100° C., and
b) a viscosity index of from 110 to 400, and
c) a pour point below −10° C., and
d) a flash point of 150° C. or more, and
e) less than 6% viscosity loss in a tapered roller bearing shear stability test.

40. The polyalpha-olefin of claim 2 wherein the polyalpha-olefin has
a) a kinematic viscosity of from 3 to 3000 cSt at 100° C., and
b) a viscosity index of from 135 to 400, and
c) a pour point below −10° C., and d) a flash point of 200° C. or more, and
e) less than 3% viscosity loss in a tapered roller bearing shear stability test.

41. The polyalpha-olefin of claim 2 wherein the polyalpha-olefin has a specific gravity of 0.75 to 0.96 g/cm$^3$.

42. The polyalpha-olefin of claim 2 where ethylene, propylene and butene oligomer units are present at less than 1 weight %.

43. The polyalpha-olefin of claim 2 where the oligomer units having 5 to 24 carbon atoms are present at 60 mole % or more.

44. The polyalpha-olefin of claim 2 where the oligomer units having 5 to 24 carbon atoms are present at 70 mole % or more.

45. The polyalpha-olefin of claim 2 where the oligomer units having 5 to 24 carbon atoms are present at 80 mole % or more.

46. The polyalpha-olefin of claim 2 where the oligomer units having 5 to 24 carbon atoms are present at 90 mole % or more.

47. The polyalpha-olefin of claim 2 wherein the polyalpha-olefin has a Bromine number of 3 or more.

48. The polyalpha-olefin of claim 2 wherein the polyalpha-olefin has a Bromine number of 5 or more.

49. A polyalpha-olefin comprising at least 50 mole % oligomer units having 5 to 24 carbon atoms and from 0.5 to 20 mole % ethylene oligomer units, where at least 80% of the ethylene oligomer units are present in the polyalpha-olefin are present in runs of 1 to 35 carbons or less as measured by Carbon 13 NMR.

\* \* \* \* \*